(12) United States Patent
Han et al.

(10) Patent No.: US 10,934,268 B2
(45) Date of Patent: Mar. 2, 2021

(54) COMPOUND AND ORGANIC ELECTRONIC DEVICE COMPRISING SAME

(71) Applicant: LG Chem, Ltd., Seoul (KR)

(72) Inventors: Miyeon Han, Daejeon (KR); Dong Hoon Lee, Daejeon (KR); Jungoh Huh, Daejeon (KR); Boonjae Jang, Daejeon (KR); Minyoung Kang, Daejeon (KR); Dong Uk Heo, Daejeon (KR); Min Woo Jung, Daejeon (KR)

(73) Assignee: LG Chem, Ltd.

( * ) Notice: Subject to any disclaimer, the term of this patent is extended or adjusted under 35 U.S.C. 154(b) by 214 days.

(21) Appl. No.: 15/577,543

(22) PCT Filed: Dec. 20, 2016

(86) PCT No.: PCT/KR2016/014918
§ 371 (c)(1),
(2) Date: Nov. 28, 2017

(87) PCT Pub. No.: WO2017/111420
PCT Pub. Date: Jun. 29, 2017

(65) Prior Publication Data
US 2018/0170902 A1 Jun. 21, 2018

(30) Foreign Application Priority Data
Dec. 23, 2015 (KR) .................... 10-2015-0184799

(51) Int. Cl.
*H01L 51/50* (2006.01)
*C07D 401/04* (2006.01)
(Continued)

(52) U.S. Cl.
CPC ......... *C07D 401/04* (2013.01); *C07D 215/04* (2013.01); *C07D 215/06* (2013.01); *C07D 471/04* (2013.01); *C07D 487/04* (2013.01); *C09K 11/06* (2013.01); *H01L 51/0052* (2013.01); *H01L 51/0058* (2013.01); *H01L 51/0067* (2013.01); *H01L 51/0072* (2013.01);
(Continued)

(58) Field of Classification Search
None
See application file for complete search history.

(56) References Cited

U.S. PATENT DOCUMENTS

2003/0137239 A1  7/2003  Matsuura et al.
2004/0251816 A1  12/2004  Leo et al.
(Continued)

FOREIGN PATENT DOCUMENTS

CN  103797605 A  5/2014
EP  2055709 A2   5/2009
(Continued)

OTHER PUBLICATIONS

European Search Report including Written Opinion for Application No. EP16879287.7 dated May 24, 2019.
(Continued)

*Primary Examiner* — Gregory D Clark
(74) *Attorney, Agent, or Firm* — Lerner, David, Littenberg, Krumholz & Mentlik, LLP

(57) ABSTRACT

The present specification relates to a compound and an organic electronic device including the same.

19 Claims, 1 Drawing Sheet

(51) Int. Cl.
  *C09K 11/06* (2006.01)
  *H01L 51/00* (2006.01)
  *C07D 215/04* (2006.01)
  *C07D 487/04* (2006.01)
  *C07D 471/04* (2006.01)
  *C07D 215/06* (2006.01)
  *H01L 51/52* (2006.01)
  *H01M 4/02* (2006.01)

(52) U.S. Cl.
  CPC ........ *H01L 51/506* (2013.01); *H01L 51/5203* (2013.01); *C09K 2211/1029* (2013.01); *H01L 51/5076* (2013.01); *H01M 2004/027* (2013.01); *H01M 2004/028* (2013.01); *Y02E 10/549* (2013.01)

(56) References Cited

U.S. PATENT DOCUMENTS

| | | | | |
|---|---|---|---|---|
| 2007/0018569 A1* | 1/2007 | Kawamura | ............ | H05B 33/14 313/504 |
| 2009/0053557 A1* | 2/2009 | Spindler | ............ | H01L 51/0058 428/690 |
| 2014/0183517 A1 | 7/2014 | Huh et al. | | |
| 2015/0236273 A1 | 8/2015 | Jang et al. | | |
| 2017/0279055 A1 | 9/2017 | Jang et al. | | |

FOREIGN PATENT DOCUMENTS

| | | |
|---|---|---|
| EP | 2924020 A1 | 9/2015 |
| JP | 2003105332 A | 4/2003 |
| JP | 2008222589 A | 9/2008 |
| JP | 2014508130 A | 4/2014 |
| KR | 20110081698 A | 7/2011 |
| KR | 20130023071 A | 3/2013 |
| KR | 10-2013-0128322 * | 11/2013 ........... C07D 401/14 |
| KR | 20130128322 A | 11/2013 |
| KR | 2014020942 * | 2/2014 ............. C09K 11/06 |
| KR | 20140065342 A | 5/2014 |
| KR | 101429035 B1 | 8/2014 |
| KR | 20150135626 A | 12/2015 |
| WO | 2003012890 A2 | 2/2003 |
| WO | 2012157537 A1 | 11/2012 |
| WO | 2014185751 A1 | 11/2014 |
| WO | 2016068585 A1 | 5/2016 |

OTHER PUBLICATIONS

F-I Wu et. al.: "Tuning the emission and morphology of cyclometalated iridium complexes and their applications to organic light-emitting diodes.", Journal of Materials Chemistry, vol. 15, Jan. 10, 2005, pp. 1035-1042, XP002790718.

J. Park et. al.: "Synthesis, characterization of the phenylquinoline-based on iridium (III) complexes for solution processable phosphorescent organic light-emitting diodes.", Organic Eectronics, vol. 14, May 23, 2013, pp. 2114-2123, XP002790720.

L. Chen et. al.: "Tuning the saturated red emission: synthesis, electrochemistry and photophysics of 2-arylquinoline based iridium (III) complexes and their application in OLEDs.", Journal of Materials Chemistry, vol. 16, Jul. 14, 2006, pp. 3332-3339, XP002790721.

Q. Zhang et. al.: "The synthesis, crystal structures and photophysical properties of series of novel 4,6-diphenyl-1,9-anthrazolines.", Dyes and Pigments, vol. 91, Mar. 9, 2011, pp. 89-97, XP002790719.

Search report from International Application No. PCT/KR2016/014918, dated Apr. 5, 2017.

Chinese Search Report for Application No. 201680034119.8 dated Jun. 24, 2020, 1 page.

\* cited by examiner

[Figure 1]
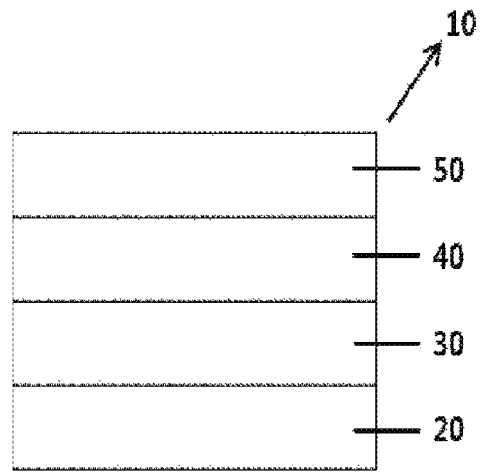
[Figure 2]
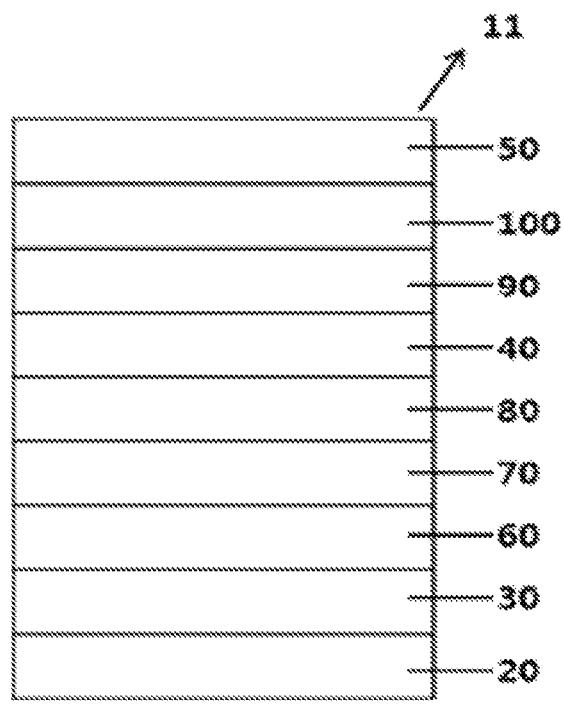

COMPOUND AND ORGANIC ELECTRONIC DEVICE COMPRISING SAME

CROSS-REFERENCE TO RELATED APPLICATIONS

The present application is a national phase entry under 35 U.S.C. § 371 of International Application No. PCT/KR2016/014918 filed Dec. 20, 2016, which claims priority from Korean Patent Application No. 10-2015-0184799 filed Dec. 23, 2015, all of which are incorporated herein by reference.

TECHNICAL FIELD

The present specification relates to a compound and an organic electronic device including the same.

BACKGROUND ART

Representative examples of an organic electronic device include an organic light emitting device. In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

International Publication No. 2003-012890

DETAILED DESCRIPTION OF THE INVENTION

Technical Problem

The present specification has been made in an effort to provide a compound and an organic electronic device including the same.

Technical Solution

The present specification provides a compound represented by the following Chemical Formula 1.

[Chemical Formula 1]

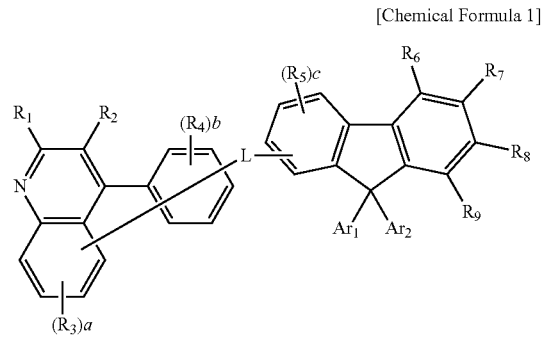

In Chemical Formula 1,

L is a direct bond; or a substituted or unsubstituted arylene group, $Ar_1$ and $Ar_2$ are the same as or different from each other, and are each independently hydrogen; deuterium; a substituted or unsubstituted alkyl group; a substituted or unsubstituted cycloalkyl group; a substituted or unsubstituted aryl group; or a substituted or unsubstituted heteroaryl group, or may be bonded to an adjacent group to form a ring, $R_1$ to $R_9$ are the same as or different from each other, and are each independently hydrogen; deuterium; a substituted or unsubstituted alkyl group; a substituted or unsubstituted cycloalkyl group; a substituted or unsubstituted aryl group; or a substituted or unsubstituted heteroaryl group, or may be bonded to an adjacent group to form a ring, a is an integer from 1 to 4, b is an integer from 1 to 5, c is an integer from 1 to 3, a+b is an integer from 2 to 8, and when a to c are each 2 or more, structures in the parenthesis are the same as or different from each other.

Further, the present specification provides an organic electronic device including: a first electrode; a second electrode disposed to face the first electrode; and an organic material layer having one or more layers disposed between the first electrode and the second electrode, in which one or more layers of the organic material layer include the above-described compound.

Advantageous Effects

The compound according to an exemplary embodiment of the present specification is used for an organic electronic device including an organic light emitting device, and thus may lower the driving voltage of the organic electronic device and improve the light efficiency, and enhance service life characteristics of the device due to thermal stability of the compound.

DESCRIPTION OF DRAWINGS

FIG. 1 illustrates an organic light emitting device 10 according to an exemplary embodiment of the present specification.

FIG. 2 illustrates an organic light emitting device 11 according to another exemplary embodiment of the present specification.

EXPLANATION OF REFERENCE NUMERALS AND SYMBOLS 10, 11: Organic light emitting device
20: Substrate
30: First electrode
40: Light emitting layer
50: Second electrode
60: Hole injection layer
70: Hole transporting layer
80: Electron blocking layer
90: Electron transporting layer
100: Electron injection layer

MODE FOR INVENTION

Hereinafter, the present specification will be described in more detail.

The present specification provides the compound represented by Chemical Formula 1.

The compound of Chemical Formula 1 may have characteristics suitable for use in an organic material layer used in an organic light emitting device by introducing various substituents into a core structure.

A conjugation length and an energy band gap of a compound are closely associated with each other. Specifically, the longer a conjugation length of a compound is, the smaller a band gap is. As described above, the core of the compound represented by Chemical Formula 1 includes a limited conjugation and thus has a property of a large energy band gap.

Usually, a substituent is introduced into a core structure having a large energy band gap to easily adjust the energy band gap, but when the core structure has a small energy band gap, it is difficult to significantly adjust the energy band gap by introducing a substituent. However, in the present specification, various substituents may be introduced into $R_1$ to $R_9$ of Chemical Formula 1 in the core structure having a large energy band gap as described above to synthesize compounds having various energy band gaps. However, in the present specification, various substituents may be introduced into the $R_1$ to $R_9$ positions of the core structure of the compound represented by Chemical Formula 1 to adjust the HOMO and LUMO energy levels of the compound, and characteristics at the interface between organic materials may also be improved, thereby diversifying the use of the material.

In addition, various substituents may be introduced into the core structure having the structure as described above to synthesize a compound having inherent characteristics of the introduced substituent. For example, a substituent usually used for a hole injection layer material, a hole transporting layer material, a light emitting layer material, and an electron transporting layer material, which are used for manufacturing an organic light emitting device, may be introduced into the core structure to synthesize a material which satisfies conditions required for each organic material layer.

In the present specification, among the compounds represented by Chemical Formula 1, a compound having an appropriate energy level may be selected according to the substituent and used for an organic light emitting device, thereby implementing a device having a low driving voltage and high light efficiency. In addition, it is possible to finely adjust an energy band gap by introducing various substituents into the core structure, and meanwhile, it is possible to improve characteristics at the interface between organic materials and diversify the use of material.

Furthermore, the compound represented by Chemical Formula 1 has a high glass transition temperature (Tg) and thus has excellent thermal stability. The increase in thermal stability becomes an important factor for providing driving stability to a device.

Examples of the substituents in the present specification will be described below, but are not limited thereto.

In the present specification,

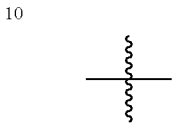

means a moiety to be linked.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; an amino group; an alkyl group; a cycloalkyl group; an alkenyl group; an amine group; a phosphine oxide group; an aryl group; a silyl group; and a heterocyclic group including one or more of N, O, S, Se, and Si atoms, being substituted with a substituent to which two or more substituents among the substituents exemplified are linked, or having no substituent.

In the present specification, an alkyl group may be straight or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, when an aryl group is a monocyclic aryl group, the number of carbon atoms thereof is not particularly limited, but is preferably 6 to 50. Specific examples of the monocyclic aryl group include a phenyl group, a biphenyl group, a terphenyl group, a quarterphenyl group, and the like, but are not limited thereto.

When the aryl group is a polycyclic aryl group, the number of carbon atoms thereof is not particularly limited, but is preferably 6 to 30. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the group may be

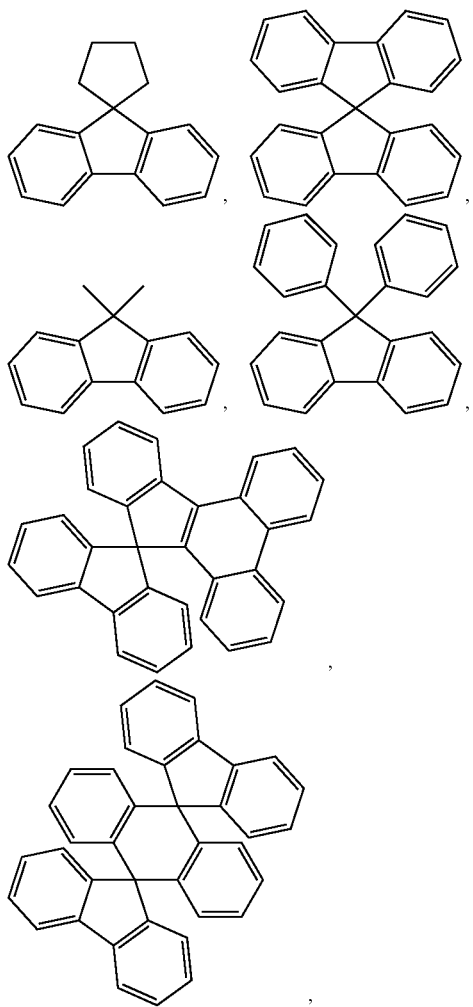

and the like, but is not limited thereto.

In the present specification, a heteroaryl group is a heterocyclic group including one or more of N, O, S, Si, and Se as a heteroatom, and the number of carbon atoms thereof is not particularly limited, but is preferably 2 to 50. Examples of the heteroaryl group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, an oxadiazolyl group, a thiadiazolyl group, a dibenzofuranyl group, and the like, but are not limited thereto.

In the present specification, the fused structure may be a structure in which an aromatic hydrocarbon ring is fused with the corresponding substituent. Examples of a fused ring of benzimidazole includes

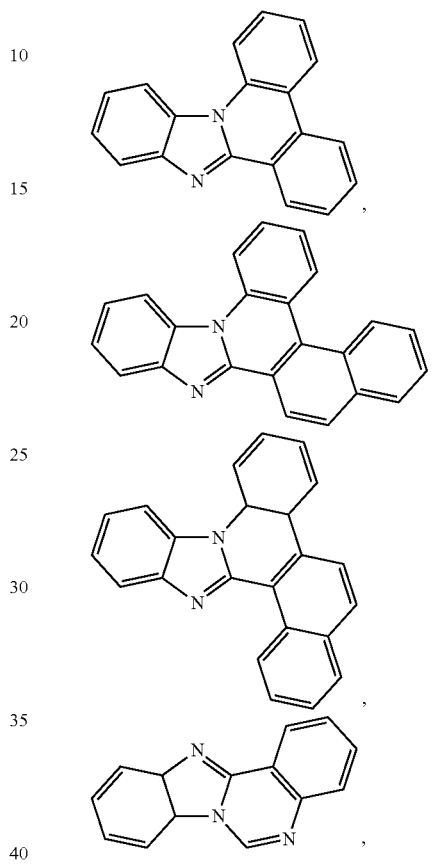

and the like, but are not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the case where adjacent groups are bonded to each other to form a ring means that adjacent groups are bonded to each other to form a 5-membered to 8-membered hydrocarbon ring or a 5-membered to 8-membered hetero ring as described above, and the ring may be monocyclic or polycyclic, may be an aliphatic ring, an aromatic ring, or a fused form thereof, and is not limited thereto.

In the present specification, a hydrocarbon ring or a hetero ring may be selected among the above-described examples of the cycloalkyl group, the aryl group, or the heteroaryl group, except for being a monovalent group, and the hydrocarbon ring or the hetero ring may be monocyclic or polycyclic, an aliphatic ring or an aromatic ring or a fused form thereof, but is not limited thereto.

In the present specification, an aromatic ring group may be monocyclic or polycyclic, and may be selected from the examples of the aryl group, except for the aromatic ring group which is not monovalent.

In the present specification, a divalent to tetravalent aromatic ring group may be monocyclic or polycyclic, and means a group having 2 to 4 bonding positions in the aryl group, that is, a divalent to tetravalent group. The above-described description on the aryl group may be applied to the aromatic ring group, except for a divalent to tetravalent aromatic ring group In the present specification, an arylene group means a group having two bonding positions in an aryl group, that is, a divalent group. The above-described description on the aryl group may be applied to the arylene group, except for a divalent arylene group.

In an exemplary embodiment of the present specification, Chemical Formula 1 may be represented by the following Chemical Formula 2 or 3.

[Chemical Formula 2]

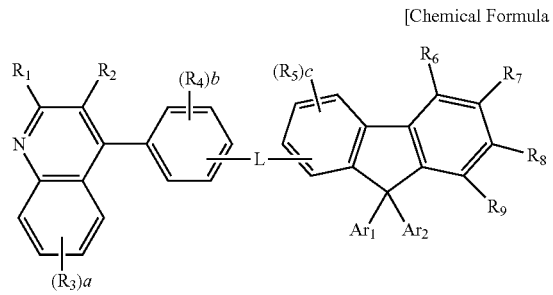

[Chemical Formula 3]

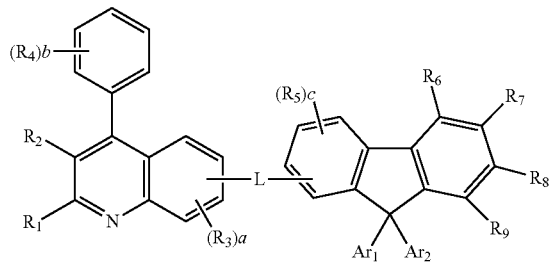

In Chemical Formulae 2 and 3,

L, $Ar_1$, $Ar_2$, $R_1$ to $R_9$, and a to c are the same as those defined in Chemical Formula 1.

In an exemplary embodiment of the present specification, Chemical Formula 1 may be represented by any one of the following Chemical Formulae 4 to 9.

[Chemical Formula 4]

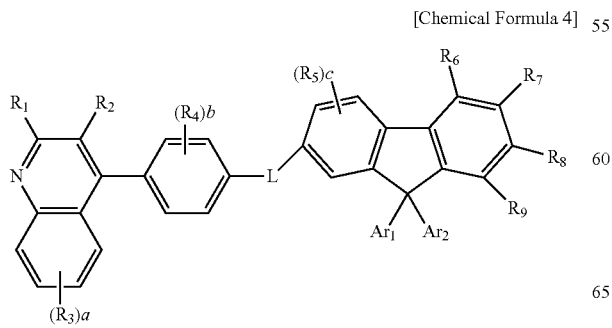

[Chemical Formula 5]

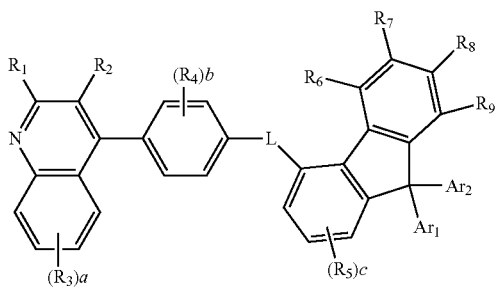

[Chemical Formula 6]

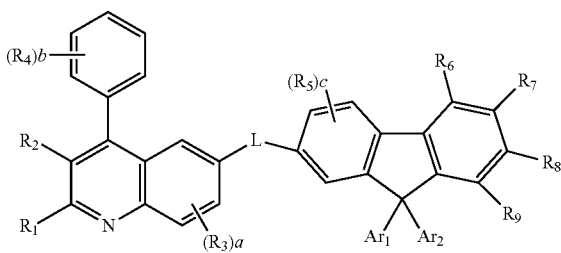

[Chemical Formula 7]

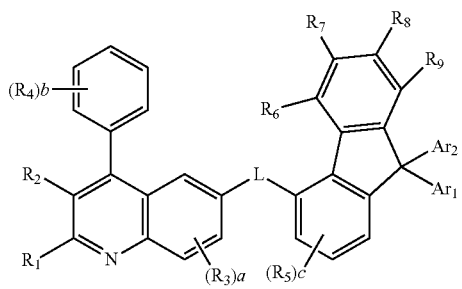

[Chemical Formula 8]

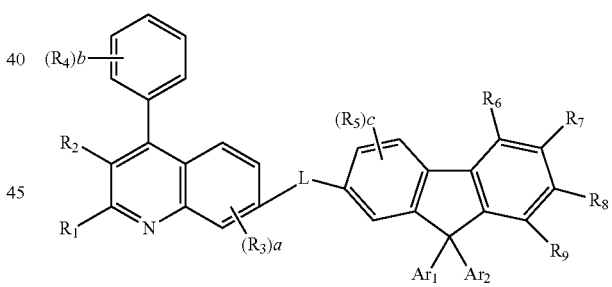

[Chemical Formula 9]

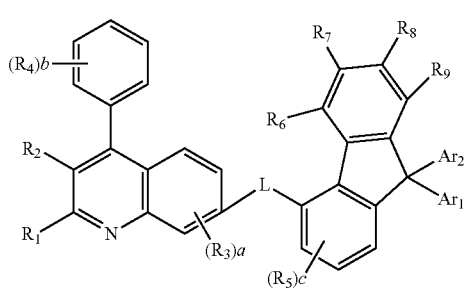

In Chemical Formulae 4 to 9,

L, $Ar_1$, $Ar_2$, $R_1$ to $R_9$, and a to c are the same as those defined in Chemical Formula 1.

In an exemplary embodiment of the present specification, L is a direct bond; a substituted or unsubstituted phenylene group; a substituted or unsubstituted biphenylylene group; a substituted or unsubstituted naphthylene group; a substituted or unsubstituted divalent phenanthrene group; or a substituted or unsubstituted divalent fluorene group.

In an exemplary embodiment of the present specification, L is a direct bond, or a phenylene group, a biphenylylene group, a naphthylene group, a divalent phenanthrene group, or a divalent fluorene group.

In an exemplary embodiment of the present specification, L is a phenylene group.

In an exemplary embodiment of the present specification, L is a biphenylylene group.

In an exemplary embodiment of the present specification, L is a naphthylene group.

In an exemplary embodiment of the present specification, L is a divalent phenanthrene group.

In an exemplary embodiment of the present specification, L is a divalent fluorene group.

In an exemplary embodiment of the present specification, $Ar_1$ and $Ar_2$ are the same as or different from each other, and are each independently hydrogen; deuterium; a substituted or unsubstituted alkyl group; a substituted or unsubstituted cycloalkyl group; a substituted or unsubstituted aryl group; or a substituted or unsubstituted heteroaryl group, or may be bonded to an adjacent group to form a ring.

In an exemplary embodiment of the present specification, $Ar_1$ and $Ar_2$ are the same as or different from each other, and are each independently a substituted or unsubstituted aryl group having 2 to 30 carbon atoms.

In an exemplary embodiment of the present specification, $Ar_1$ and $Ar_2$ are the same as or different from each other, and are each independently a substituted or unsubstituted phenyl group, a substituted or unsubstituted biphenyl group, a substituted or unsubstituted terphenyl group, a substituted or unsubstituted naphthyl group, a substituted or unsubstituted triphenyl group, a substituted or unsubstituted phenanthryl group, or a substituted or unsubstituted fluorenyl group.

In an exemplary embodiment of the present specification, $Ar_1$ and $Ar_2$ are the same as or different from each other, and are each independently a substituted or unsubstituted phenyl group, or may be bonded to an adjacent group to form a ring.

In an exemplary embodiment of the present specification, $Ar_1$ and $Ar_2$ are a phenyl group.

In an exemplary embodiment of the present specification, $Ar_1$ and $Ar_2$ may be bonded to an adjacent group to form a ring.

In an exemplary embodiment of the present specification, $R_1$ to $R_9$ are the same as or different from each other, and are each independently hydrogen; deuterium; a substituted or unsubstituted alkyl group; a substituted or unsubstituted cycloalkyl group; a substituted or unsubstituted aryl group; or a substituted or unsubstituted heteroaryl group, or may be bonded to an adjacent group to form a ring.

In an exemplary embodiment of the present specification, $R_1$ to $R_9$ are the same as or different from each other, and are each independently a substituted or unsubstituted aryl group having 2 to 30 carbon atoms.

In an exemplary embodiment of the present specification, $R_1$ to $R_9$ are the same as or different from each other, and are each independently a substituted or unsubstituted phenyl group, a substituted or unsubstituted biphenyl group, a substituted or unsubstituted terphenyl group, a substituted or unsubstituted naphthyl group, a substituted or unsubstituted triphenyl group, a substituted or unsubstituted phenanthryl group, or a substituted or unsubstituted fluorenyl group.

In an exemplary embodiment of the present specification, $R_1$ to $R_9$ are the same as or different from each other, and are each independently a phenyl group. In an exemplary embodiment of the present specification, $R_1$ to $R_9$ are the same as or different from each other, and are each independently a biphenyl group.

In an exemplary embodiment of the present specification, $R_1$ to $R_9$ are the same as or different from each other, and are each independently a terphenyl group.

In an exemplary embodiment of the present specification, $R_1$ to $R_9$ are the same as or different from each other, and are each independently a naphthyl group.

In an exemplary embodiment of the present specification, $R_1$ to $R_9$ are the same as or different from each other, and are each independently a triphenyl group.

In an exemplary embodiment of the present specification, $R_1$ to $R_9$ are the same as or different from each other, and are each independently a phenanthryl group.

In an exemplary embodiment of the present specification, $R_1$ to $R_9$ are the same as or different from each other, and are each independently a fluorenyl group.

In an exemplary embodiment of the present specification, $R_1$ to $R_9$ are the same as or different from each other, and are each independently a substituted or unsubstituted heteroaryl group having 6 to 30 carbon atoms.

In an exemplary embodiment of the present specification, $R_1$ to $R_9$ are the same as or different from each other, and are each independently a substituted or unsubstituted pyridine group, a substituted or unsubstituted pyrimidine group, or a substituted or unsubstituted triazine group.

In an exemplary embodiment of the present specification, $R_1$ to $R_9$ are the same as or different from each other, and are each independently a pyridine group.

In an exemplary embodiment of the present specification, $R_1$ to $R_9$ are the same as or different from each other, and are each independently a pyrimidine group.

In an exemplary embodiment of the present specification, $R_1$ to $R_9$ are the same as or different from each other, and are each independently a triazine group.

In an exemplary embodiment of the present specification, $R_1$ is a phenyl group.

In an exemplary embodiment of the present specification, $R_1$ is a biphenyl group.

In an exemplary embodiment of the present specification, $R_1$ is a terphenyl group.

In an exemplary embodiment of the present specification, $R_1$ is a naphthyl group.

In an exemplary embodiment of the present specification, $R_1$ is a triphenyl group.

In an exemplary embodiment of the present specification, $R_1$ is a phenanthryl group.

In an exemplary embodiment of the present specification, $R_1$ is a fluorenyl group.

In an exemplary embodiment of the present specification, $R_1$ is a pyridine group.

In an exemplary embodiment of the present specification, $R_1$ is a pyrimidine group.

In an exemplary embodiment of the present specification, $R_1$ is a triazine group.

In an exemplary embodiment of the present specification, $R_2$ to $R_9$ are hydrogen.

According to an exemplary embodiment of the present specification, the compound may be any one selected among the following structural formulae.

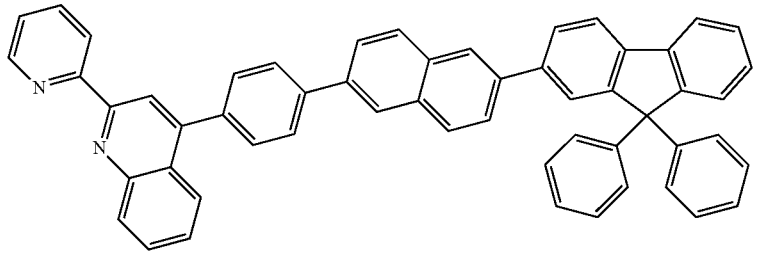
Compound 1
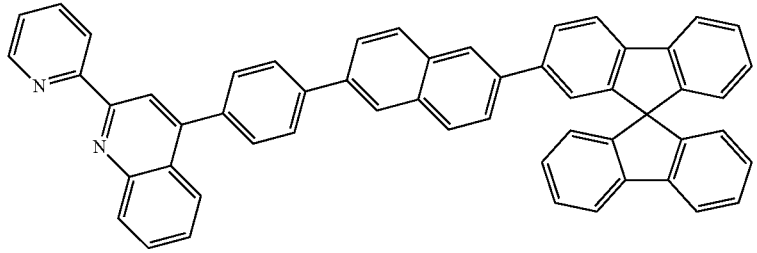
Compound 2
Compound 3
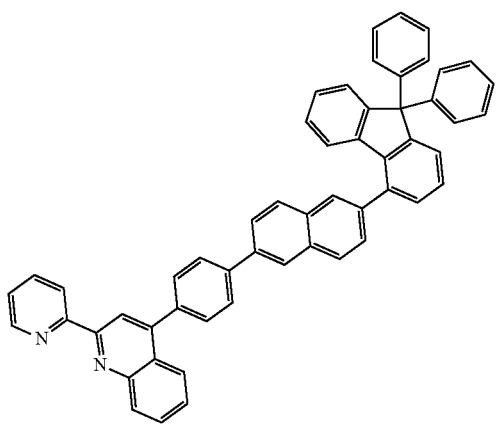
Compound 4
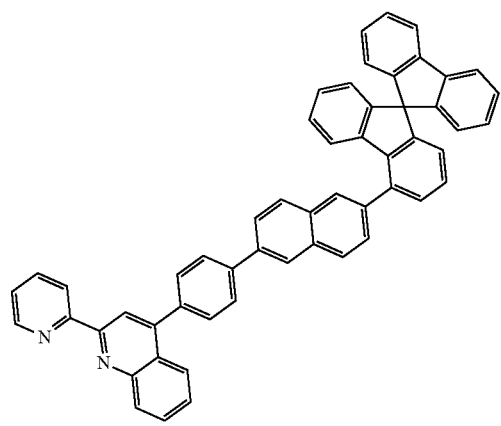
Compound 5
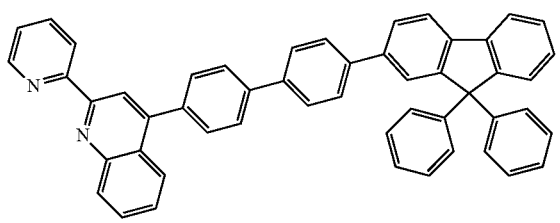
Compound 6
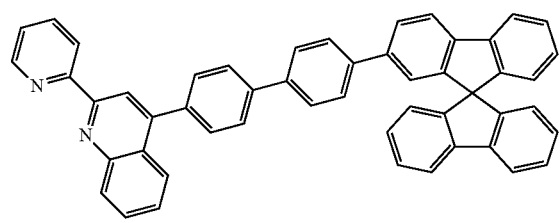

-continued
Compound 7
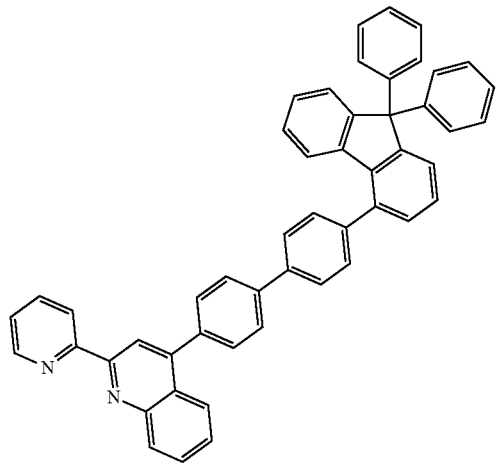
Compound 8
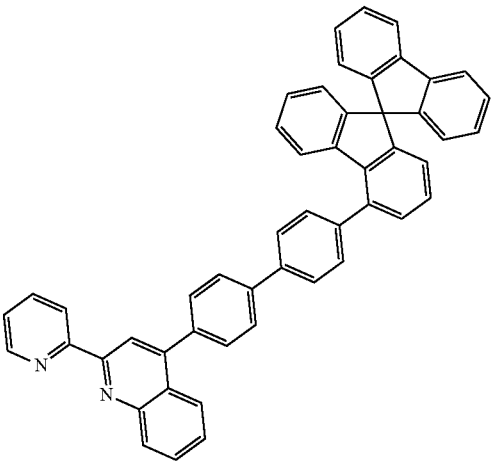
Compound 9
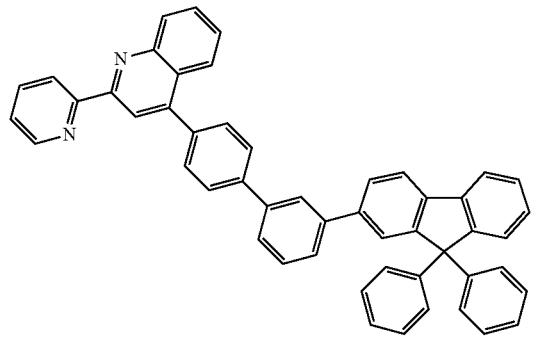
Compound 10
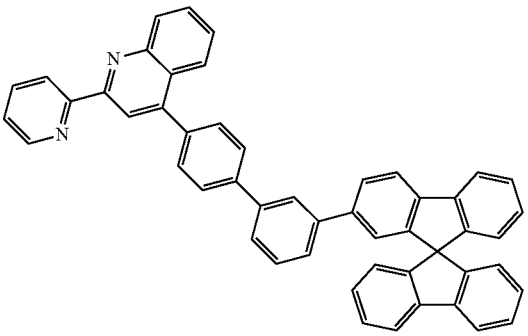
Compound 11
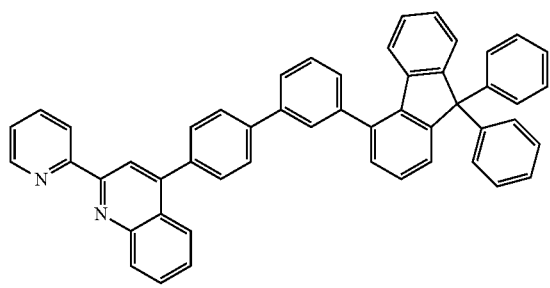
Compound 12
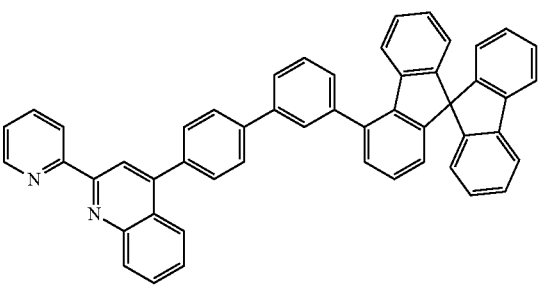
Compound 13
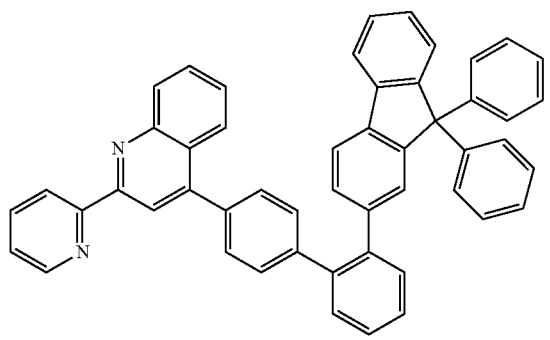
Compound 14
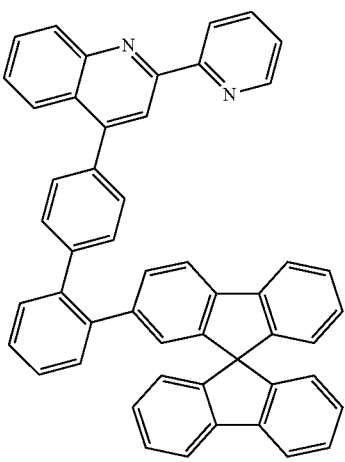

-continued
Compound 15
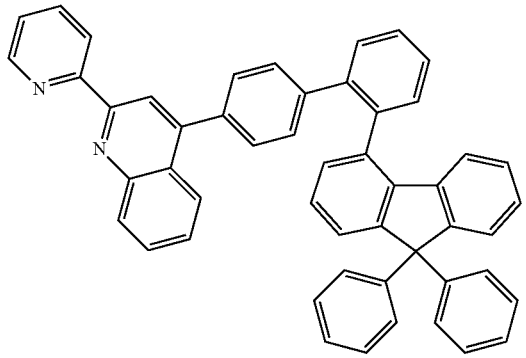
Compound 16
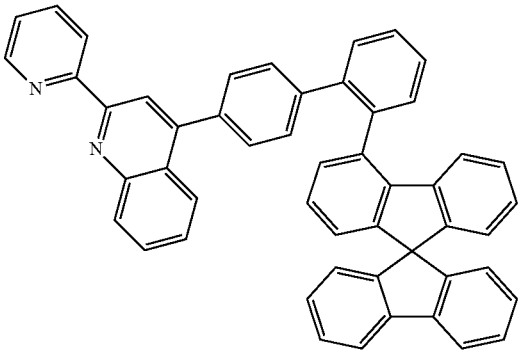
Compound 17
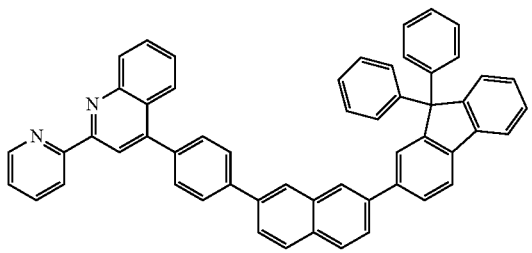
Compound 18
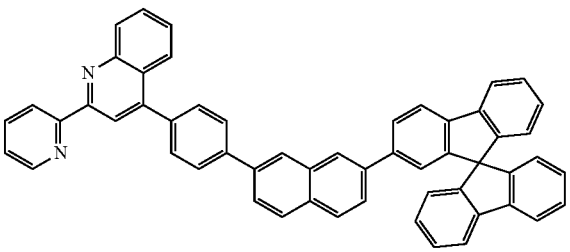
Compound 19
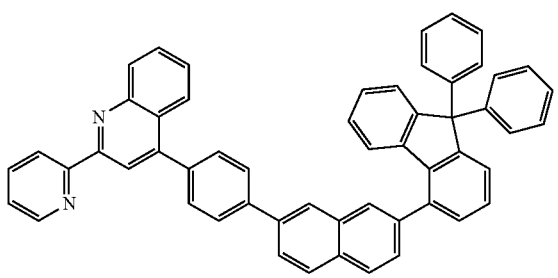
Compound 20
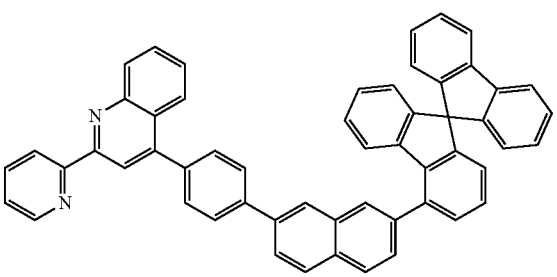
Compound 21
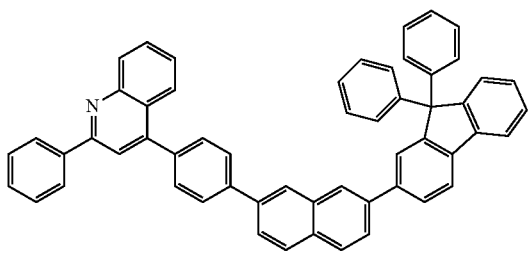
Compound 22
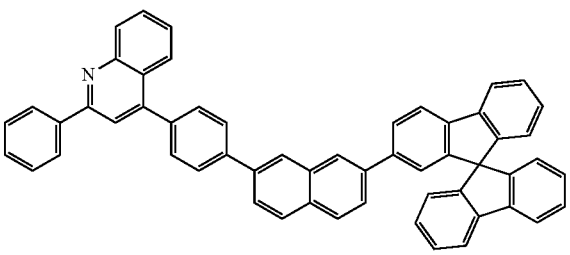
Compound 23
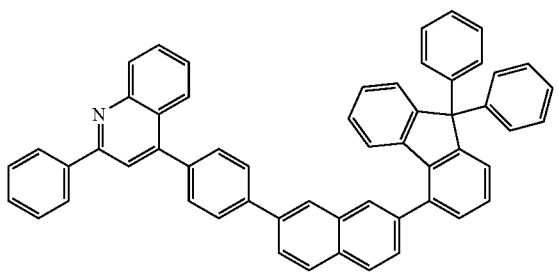
Compound 24
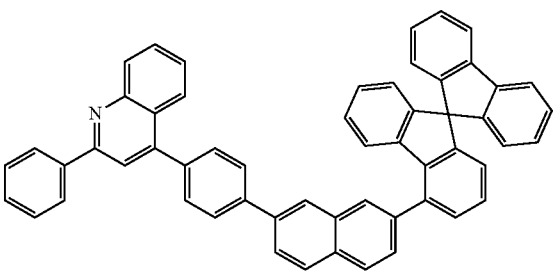

-continued
Compound 25
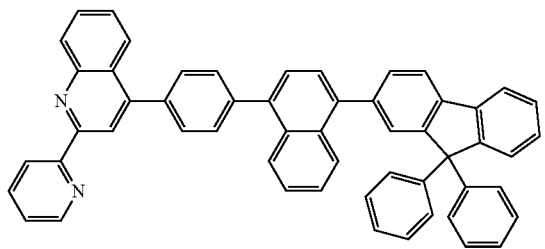
Compound 26
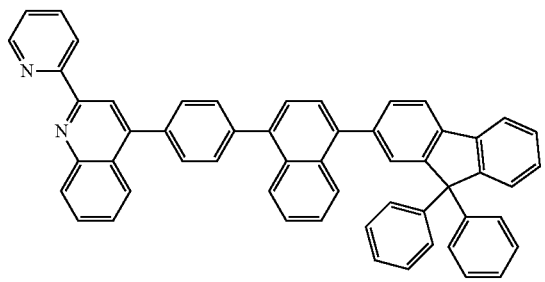
Compound 27
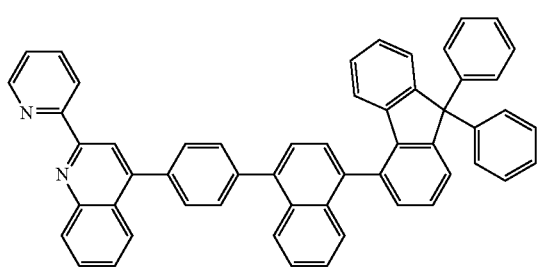
Compound 28
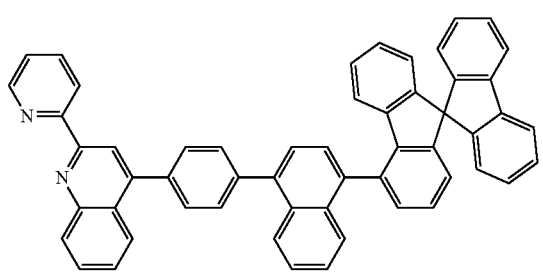
Compound 29
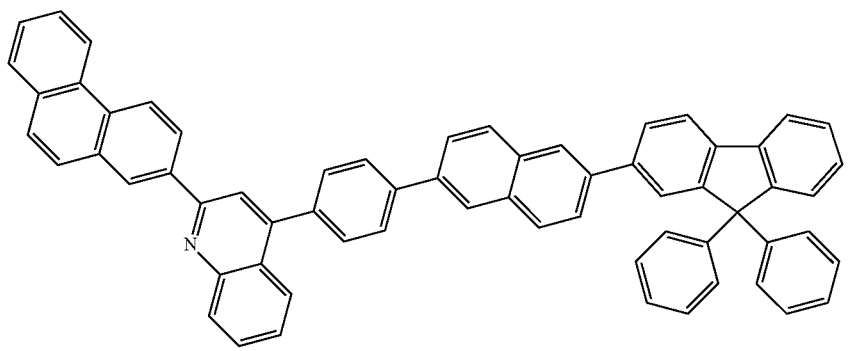
Compound 30
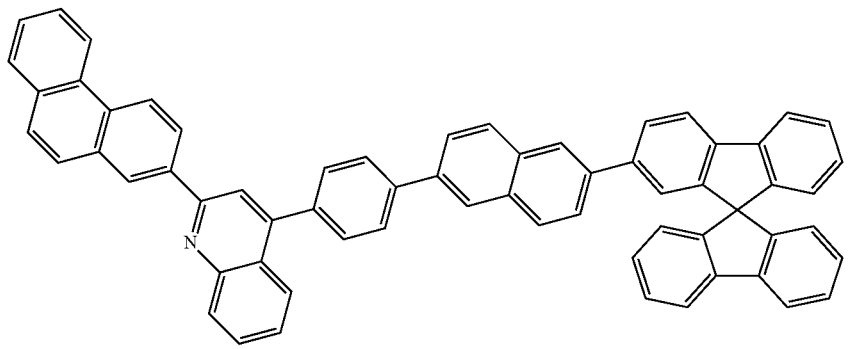

-continued
Compound 31
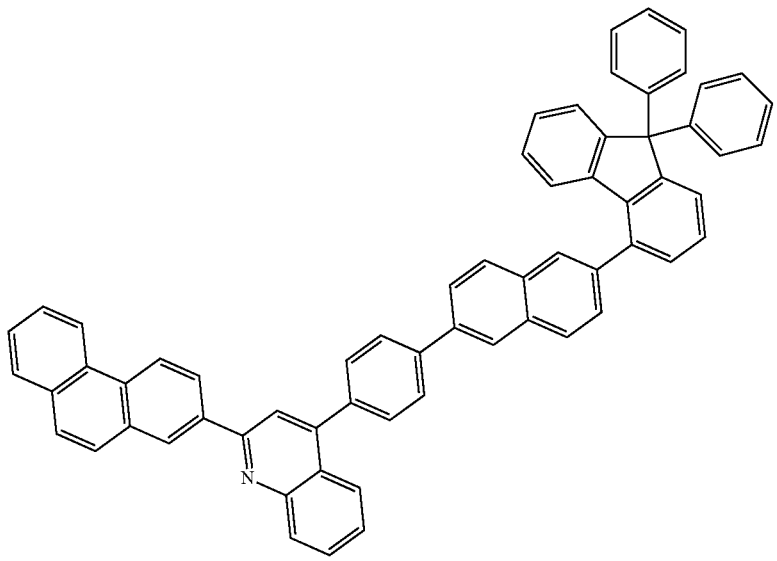
Compound 32
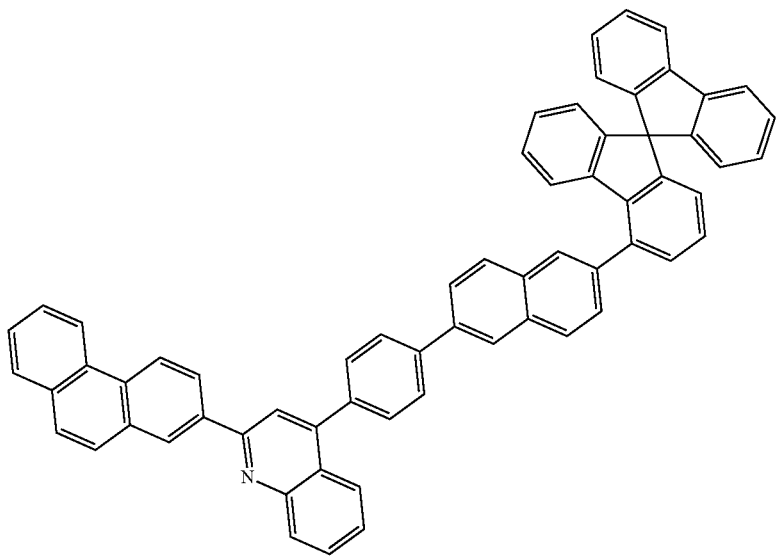
Compound 33
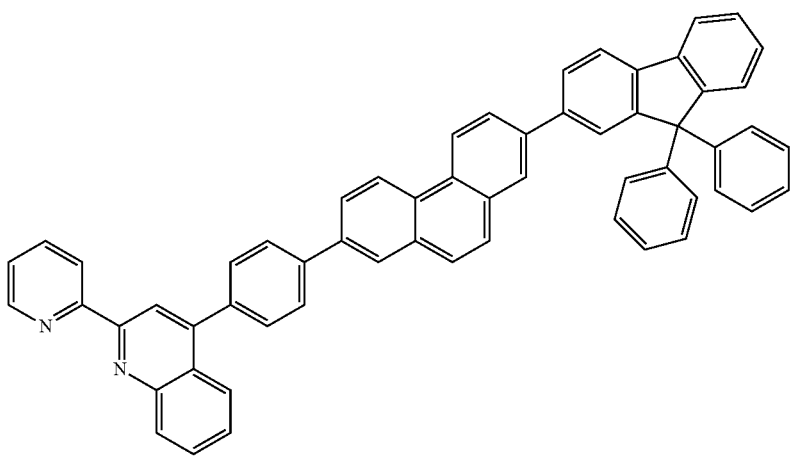

Compound 34
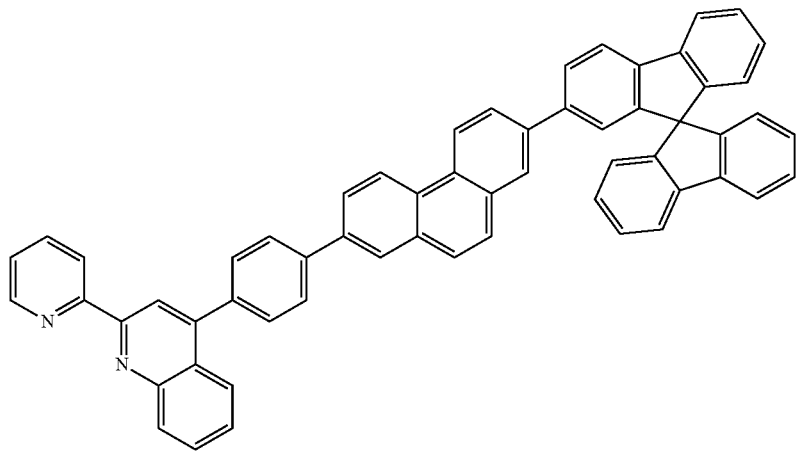
Compound 35
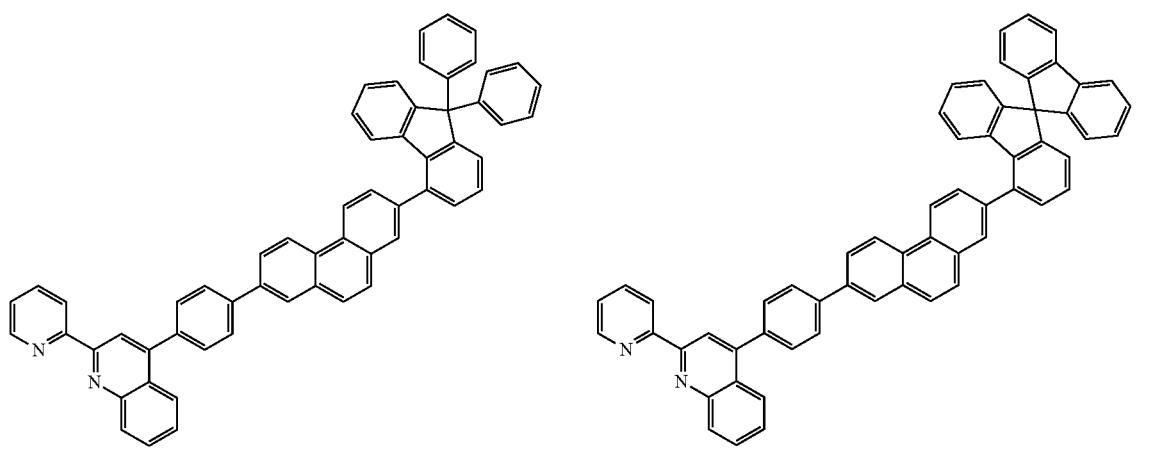
Compound 36
Compound 37
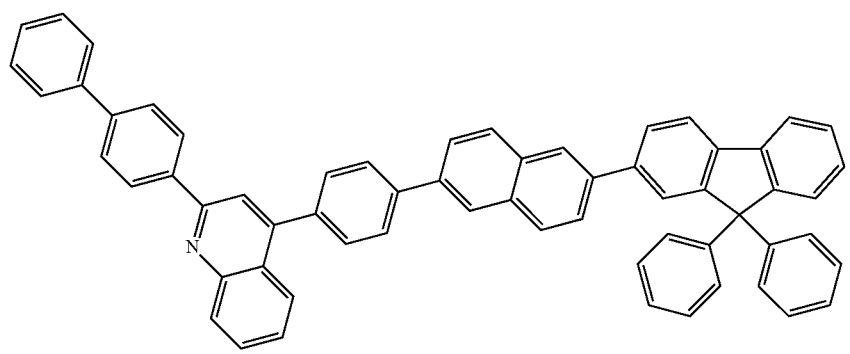
Compound 38
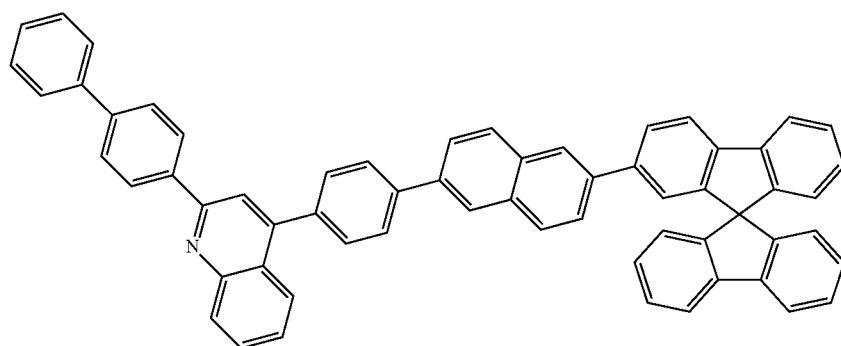

-continued
Compound 39
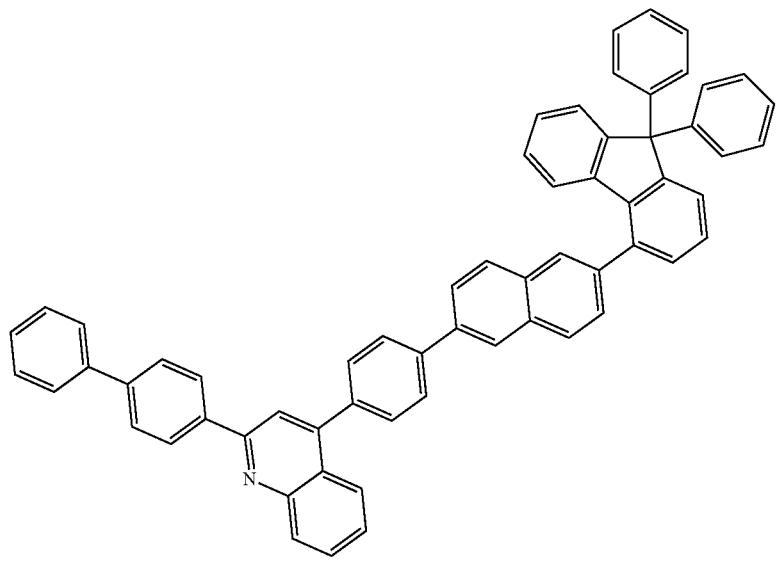
Compound 40
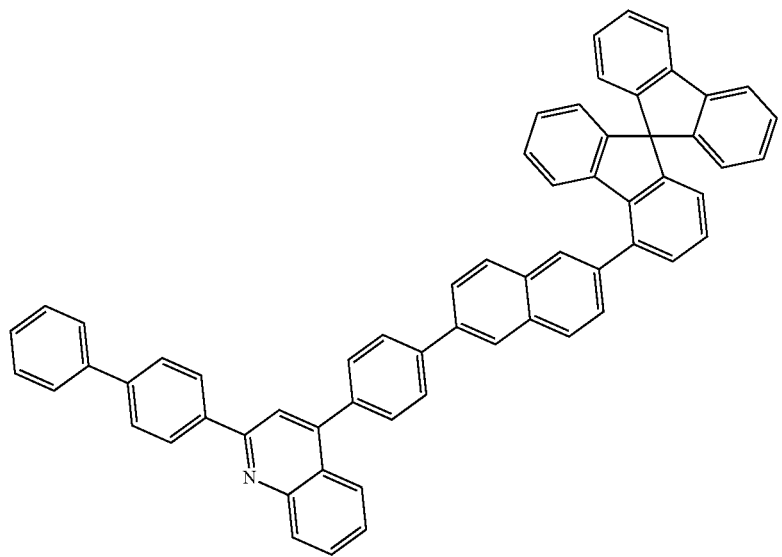
Compound 41
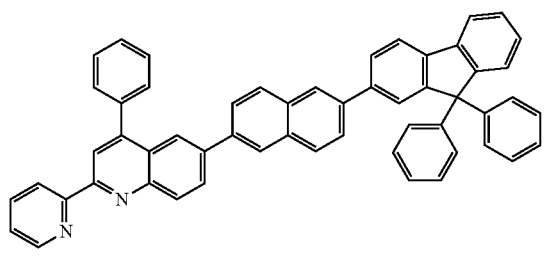
Compound 42
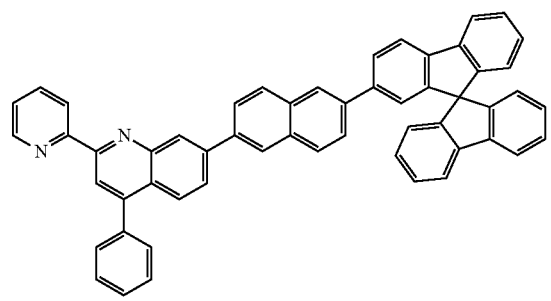

-continued
Compound 43
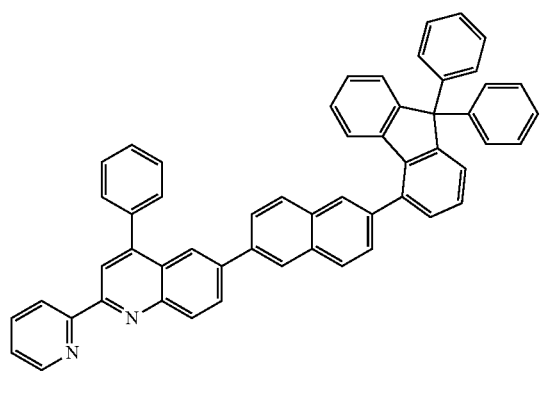
Compound 44
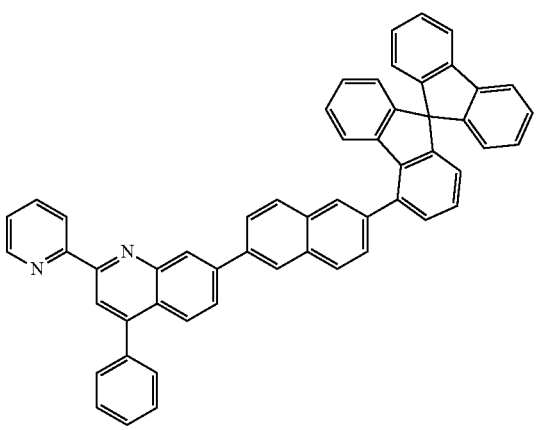
Compound 45
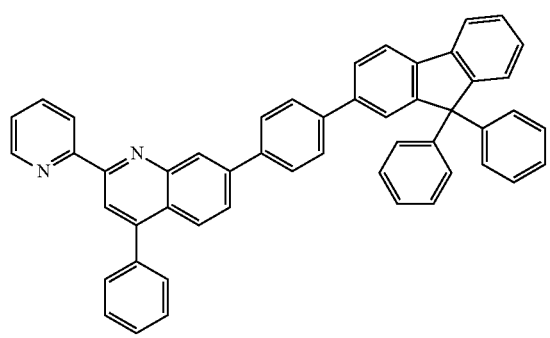
Compound 46
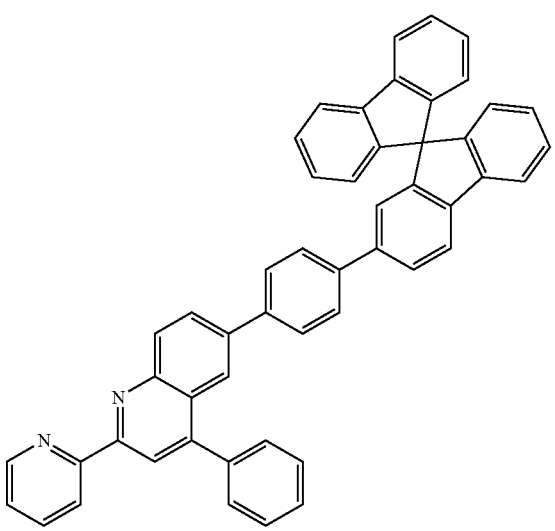
Compound 47
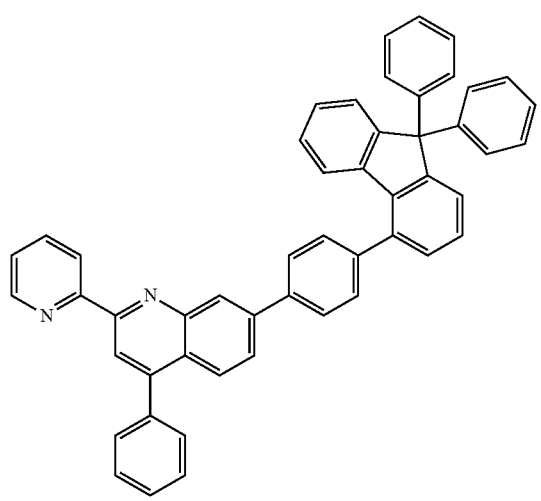
Compound 48
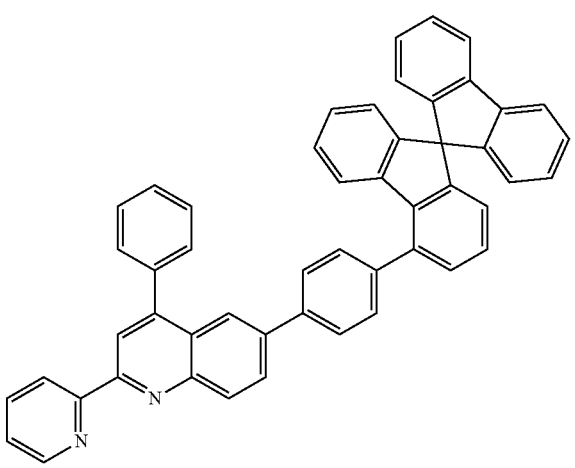

-continued
Compound 49
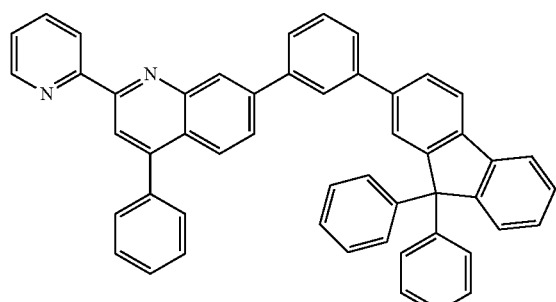
Compound 50
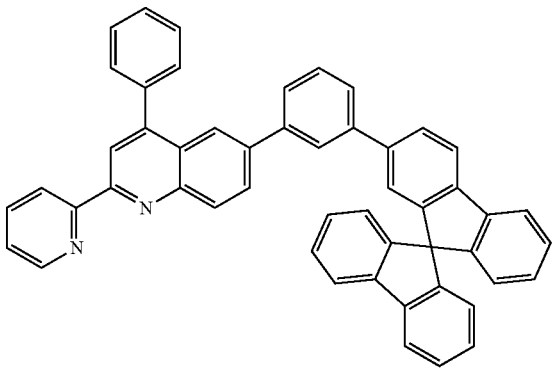
Compound 51
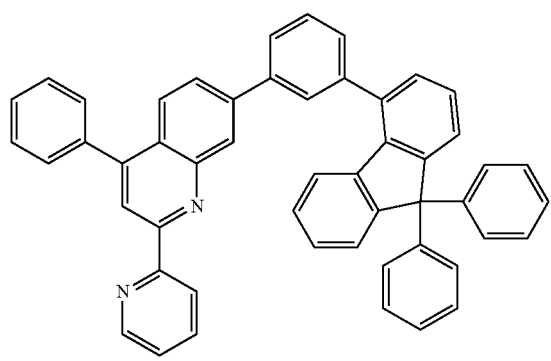
Compound 52
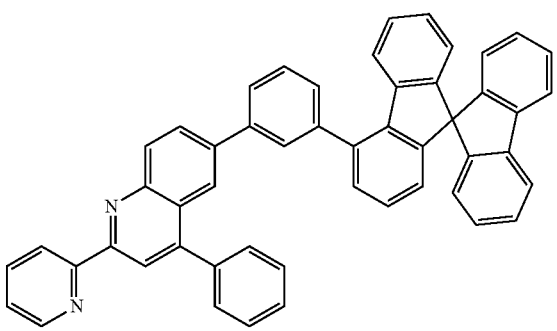
Compound 53
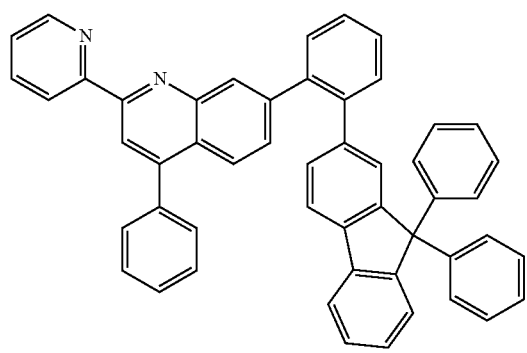
Compound 54
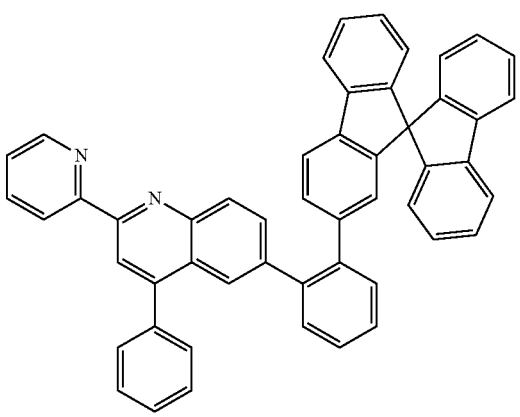

-continued
Compound 55
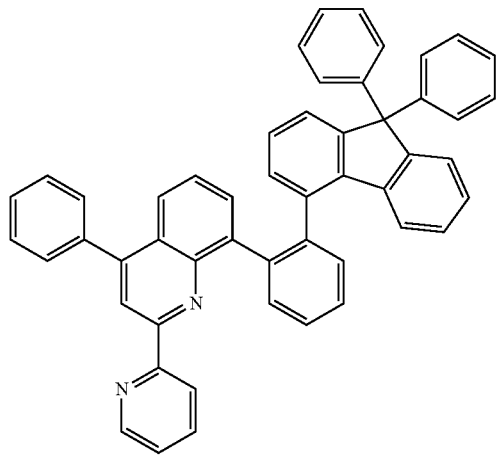
Compound 56
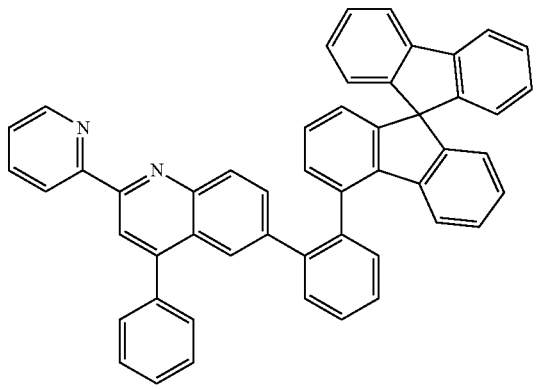
Compound 57
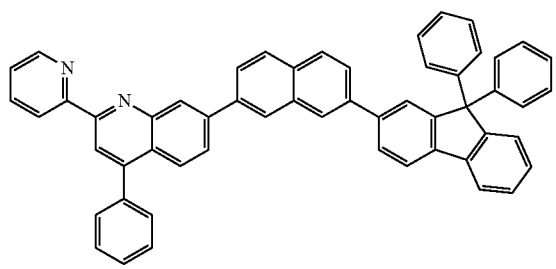
Compound 58
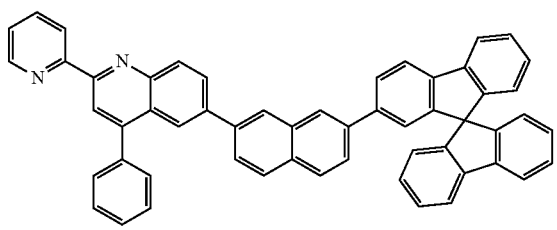
Compound 59
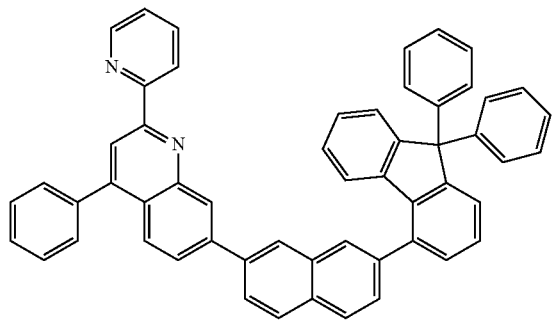
Compound 60
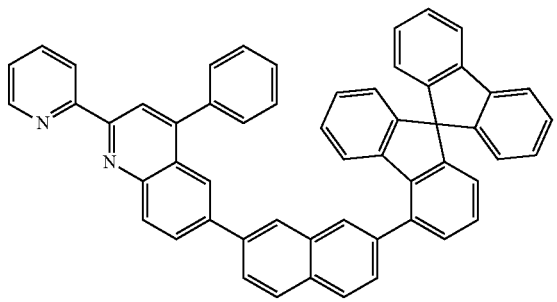
Compound 61
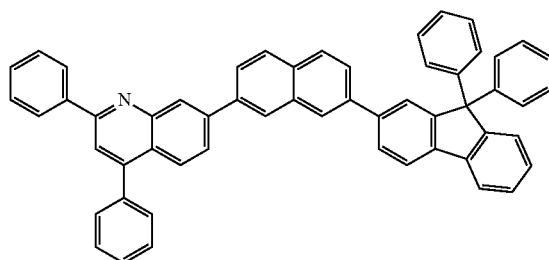
Compound 62
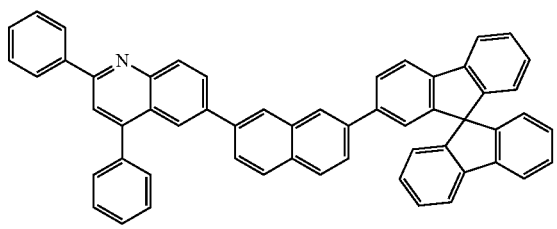

-continued
Compound 63
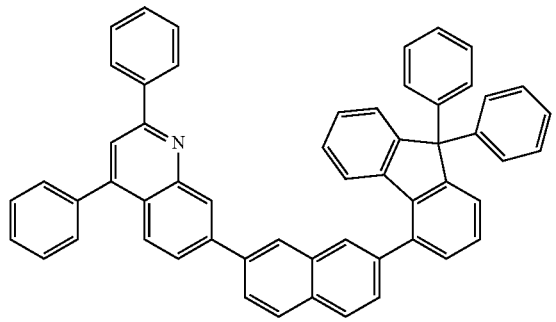
Compound 64
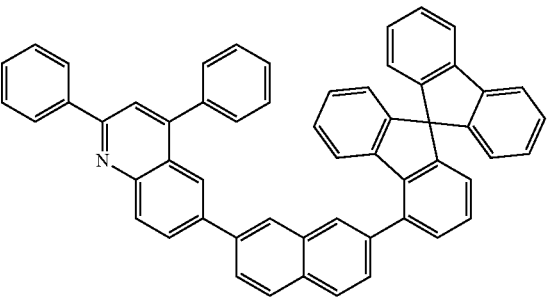
Compound 65
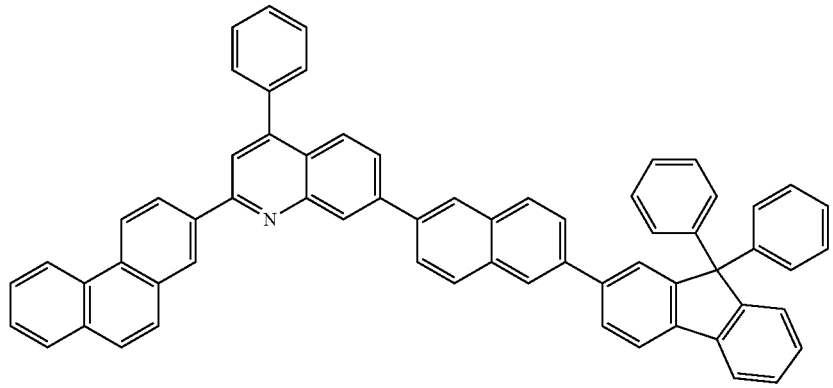
Compound 66
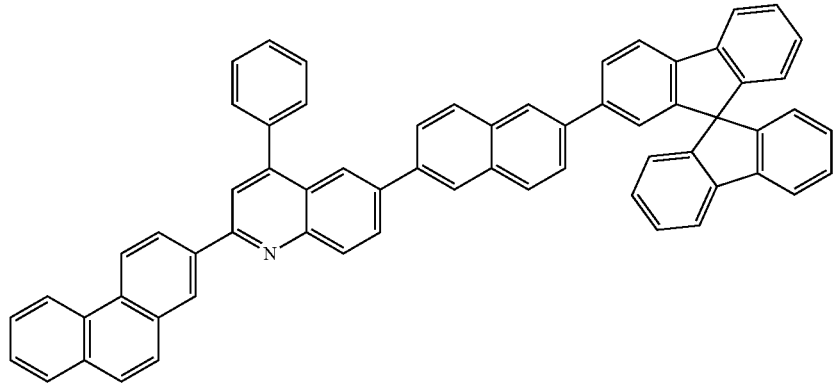
Compound 67
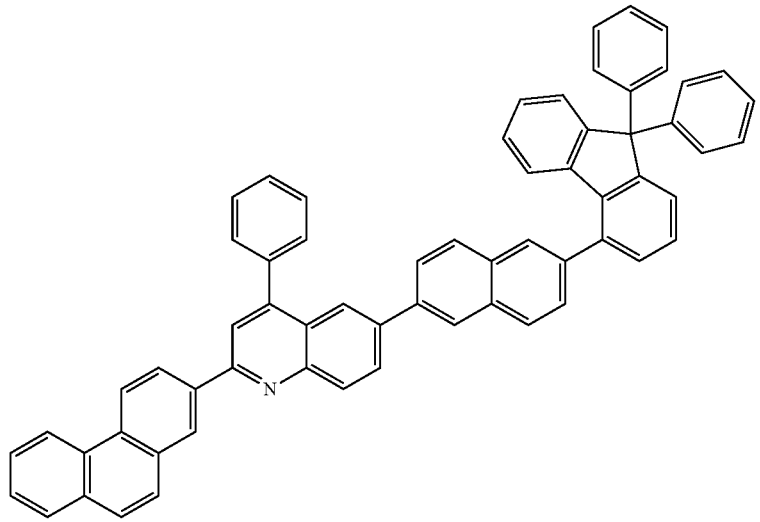

Compound 68
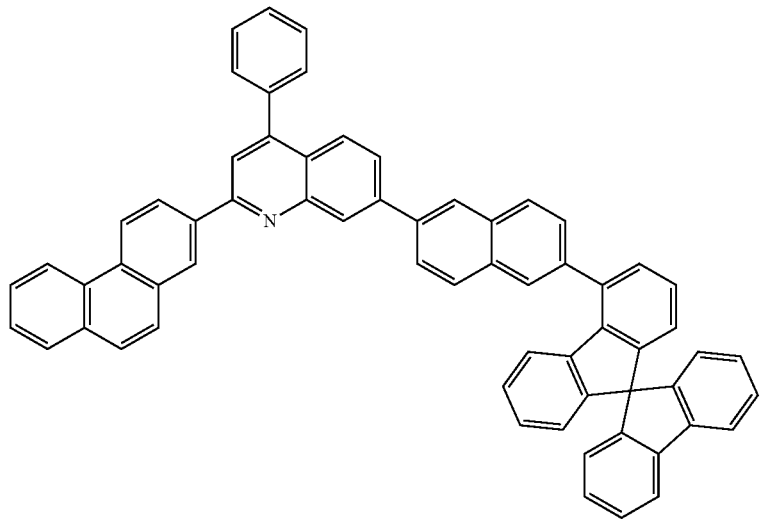
Comound 69
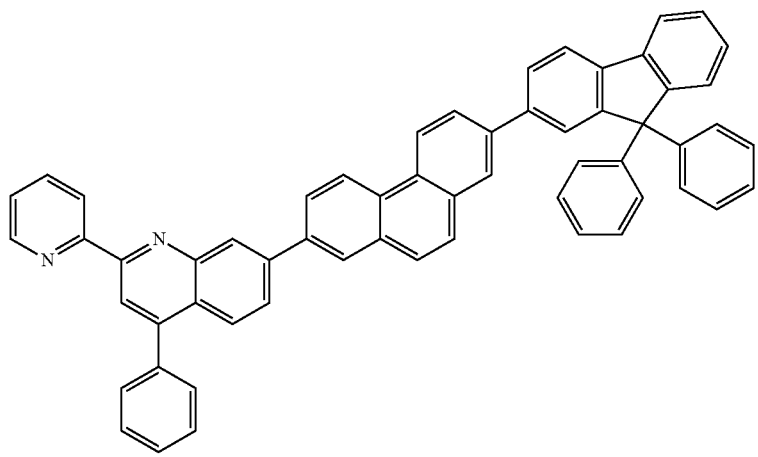
Compound 70
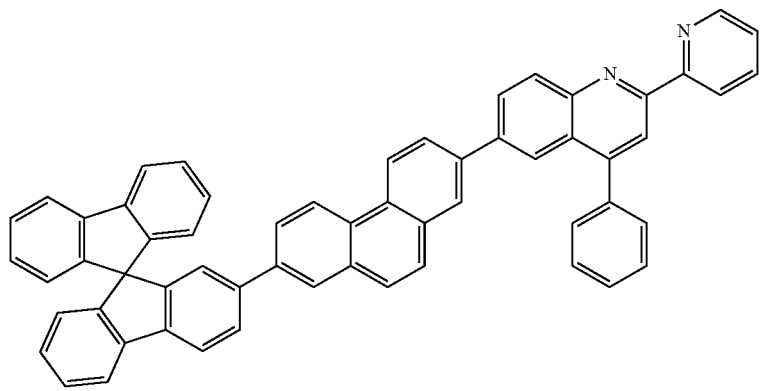

-continued
Compound 71
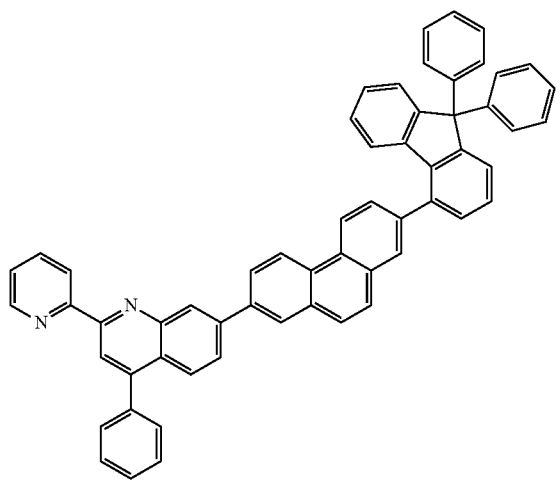
Compound 72
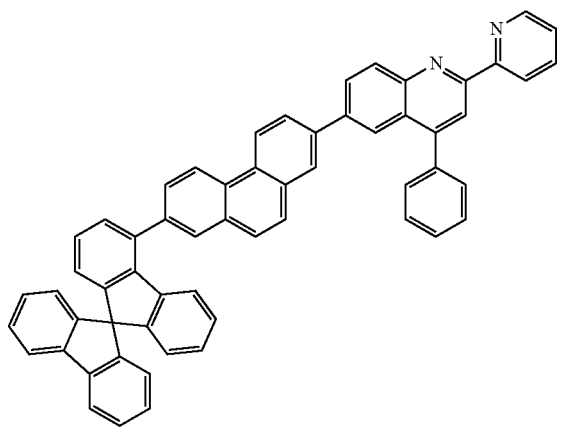
Compound 73
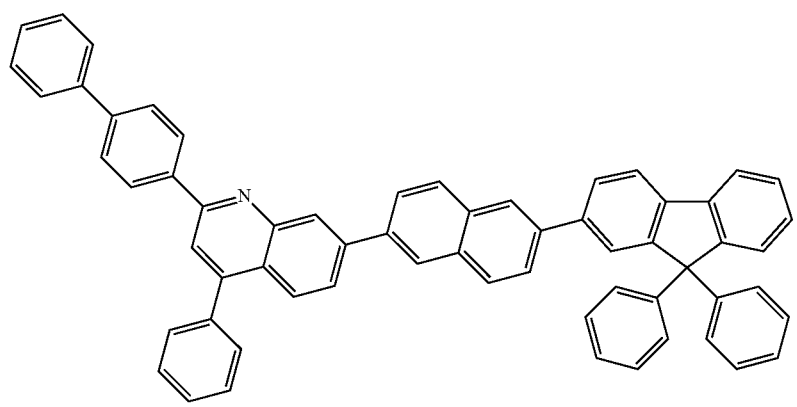
Compound 74
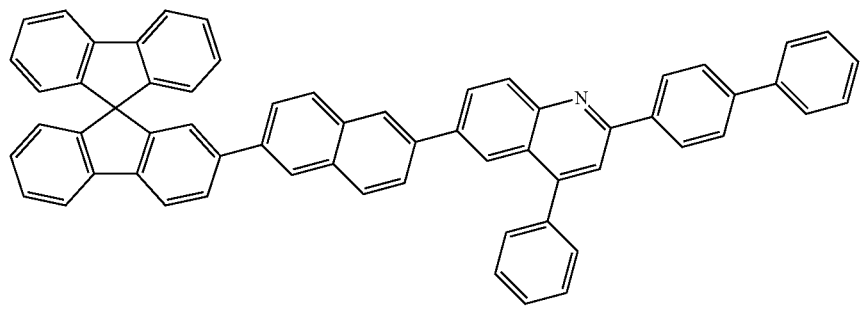

-continued
Compound 75
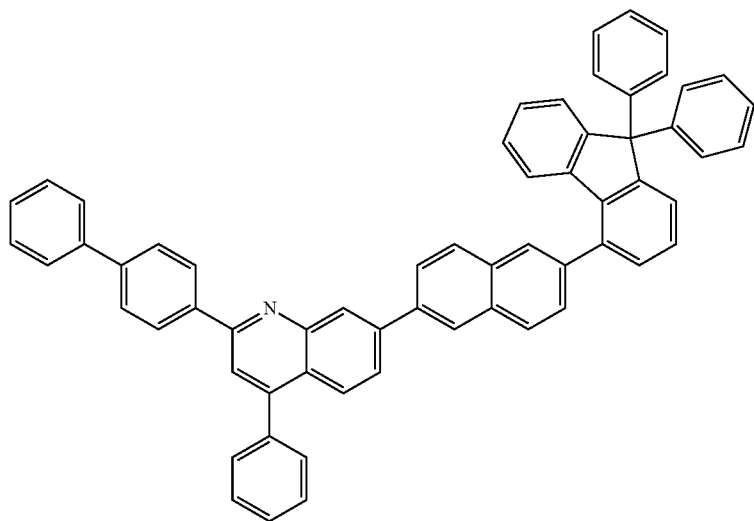
Compound 76
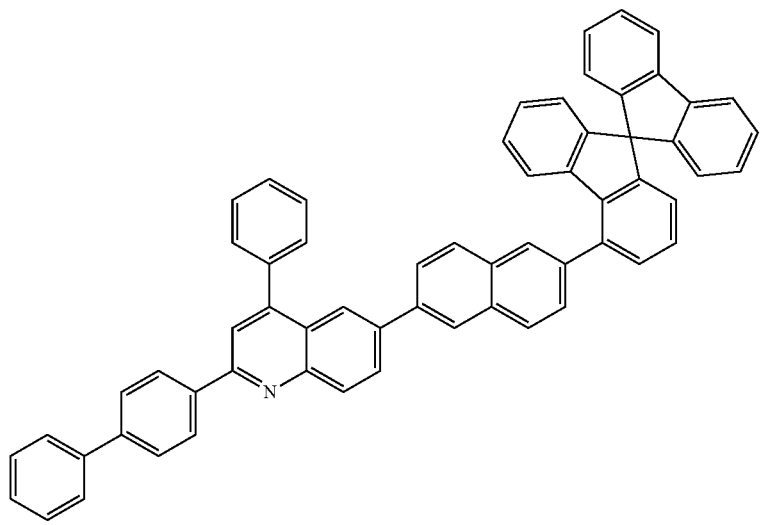
Compound 77
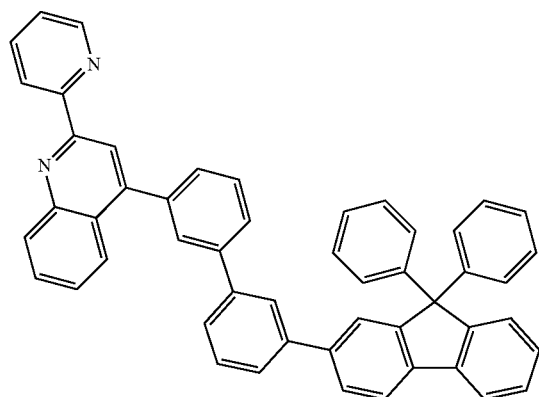
Compound 78
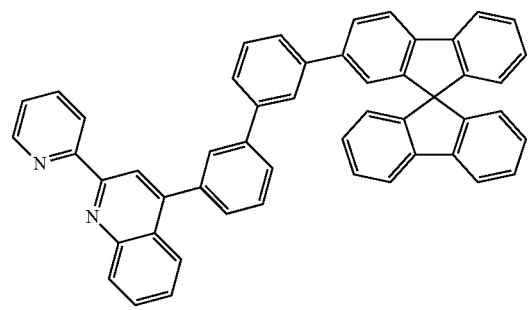

-continued

Compound 79

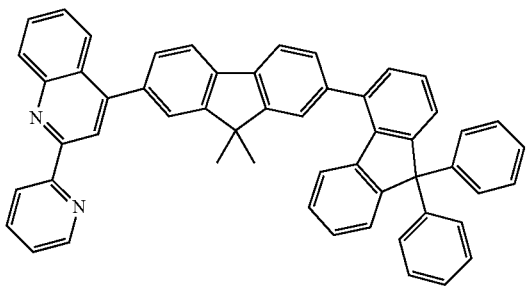

Compound 80

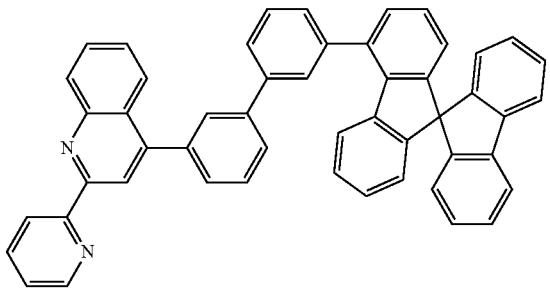

The compound according to an exemplary embodiment of the present application may be prepared by a preparation method described below. Representative examples will be described in the Preparation Examples described below, but if necessary, a substituent may be added or excluded, and the position of the substituent may be changed. Further, a starting material, a reactant, reaction conditions, and the like may be changed based on the technology known in the art.

For example, a core structure of the compound of Chemical Formula 1 may be prepared as in the following General Formulae 1 to 3. The substituent may be bonded by a method known in the art, and the kind and position of the substituent or the number of substituents may be changed according to the technology known in the art.

[General Formula 1]

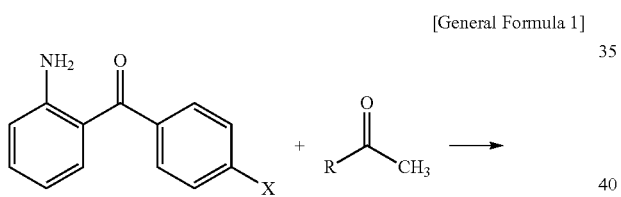

2-aminophenyl-4-halophenylmethanone and alkyl methyl ketone were put into acetic acid having a concentration of 1 M. In this case, a catalytic amount of sulfuric acid was together added thereto, and Compound A was synthesized by refluxing the resulting mixture.

[General Formula 2]

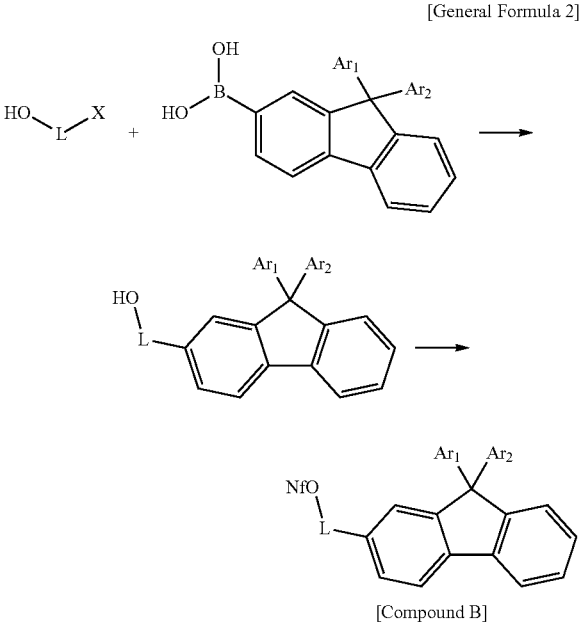

After a coupling reaction of fluorine boronic acid derivatives and linker derivatives was carried out by using a palladium (Pd) catalyst, Compound B was synthesized by carrying out a reaction of substituting a hydroxyl group with a leaving group.

[General Formula 3]

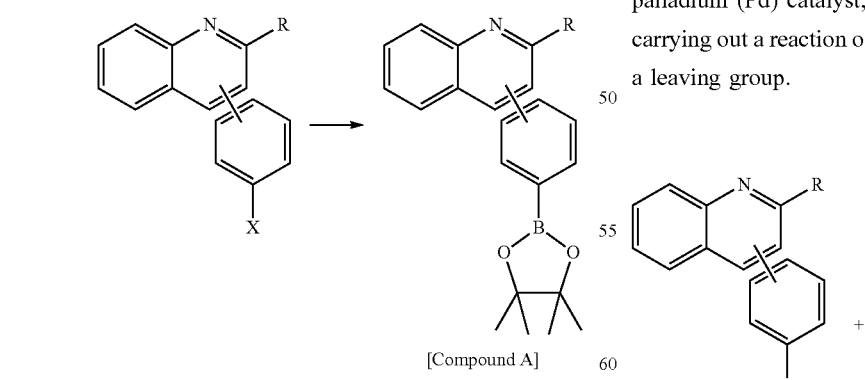

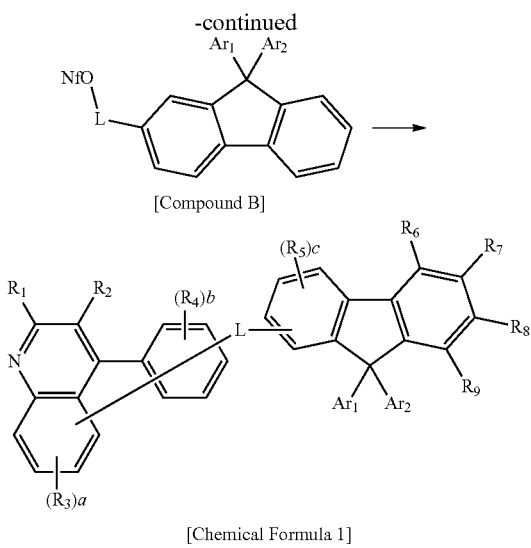

[Chemical Formula 1]

The same equivalents of Compound A and Compound B were mixed, and the structure of Chemical Formula 1 was synthesized by carrying out a coupling reaction using a palladium (Pd) catalyst.

In General Formulae 1 to 3, L, a to c, $Ar_1$ and $Ar_2$, and $R_1$ to $R_9$ are the same as those described above.

In General Formulae 1 to 3, an example of a method for synthesizing the core of Chemical Formula 1 is described, but the method is not limited thereto.

Further, the present specification provides an organic electronic device including the above-described compound.

An exemplary embodiment of the present application provides an organic electronic device including: a first electrode; a second electrode disposed to face the first electrode; and an organic material layer having one or more layers disposed between the first electrode and the second electrode, in which one or more layers of the organic material layer include the compound.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

The organic material layer of the organic electronic device of the present specification may also be composed of a single-layered structure, but may be composed of a multi-layered structure in which an organic material layer having two or more layers is stacked. For example, as a representative example of the organic electronic device of the present invention, an organic light emitting device may have a structure including a hole injection layer, a hole transporting layer, a light emitting layer, an electron transporting layer, an electron injection layer, an electron blocking layer, a hole blocking layer, and the like as organic material layer. However, the structure of the organic light emitting device is not limited thereto, and may include a fewer number of organic layers.

According to an exemplary embodiment of the present specification, the organic electronic device may be selected from the group consisting of an organic phosphorescent device, an organic solar cell, an organic photoconductor (OPC), and an organic transistor.

In an exemplary embodiment of the present specification, the organic material layer includes a light emitting layer, and the light emitting layer includes the compound.

In an exemplary embodiment of the present specification, the organic material layer includes a hole injection layer or a hole transporting layer, and the hole injection layer or the hole transporting layer includes the compound.

In an exemplary embodiment of the present specification, the organic material layer includes an electron injection layer, an electron transporting layer, or a layer which injects and transports electrons simultaneously, and the electron injection layer, the electron transporting layer, or the layer which injects and transports electrons simultaneously includes the compound.

In an exemplary embodiment of the present application, the organic material layer includes an electron blocking layer, and the electron blocking layer includes the compound.

In an exemplary embodiment of the present specification, the organic light emitting device further includes one or two or more layers selected from the group consisting of a hole injection layer, a hole transporting layer, a light emitting layer, an electron transporting layer, an electron injection layer, a hole blocking layer, and an electron blocking layer.

In an exemplary embodiment of the present specification, the organic light emitting device includes: a first electrode; a second electrode disposed to face the first electrode; a light emitting layer disposed between the first electrode and the second electrode; and an organic material layer including two or more layers disposed between the light emitting layer and the first electrode, or between the light emitting layer and the second electrode, in which at least one of the organic material layer including two or more layers includes the compound. In an exemplary embodiment of the present specification, as the organic material layer including two or more layers, two or more may be selected from the group consisting of an electron transporting layer, an electron injection layer, a layer which transports and injects electrons simultaneously, and a hole blocking layer.

In an exemplary embodiment of the present specification, the organic material layer includes an electron transporting layer having two or more layers, and at least one of the electron transporting layer having two or more layers includes the compound. Specifically, in an exemplary embodiment of the present specification, the compound may also be included in one layer of the electron transporting layer including two or more layers, and may be included in each electron transporting layer including two or more layers.

In addition, in an exemplary embodiment of the present specification, when the compound is included in each electron transporting layer including two or more layers, the other materials except for the compound may be the same as or different from each other.

In an exemplary embodiment of the present specification, the organic material layer further includes a hole injection layer or a hole transporting layer, which includes a compound including an arylamino group, a carbazolyl group, or a benzocarbazolyl group, in addition to the organic material layer including the compound.

In another exemplary embodiment, the organic light emitting device may be an organic light emitting device having a structure (normal type) in which a positive electrode, an organic material layer having one or more layers, and a negative electrode are sequentially stacked on a substrate.

When the organic material layer including the compound of Chemical Formula 1 is an electron transporting layer, the electron transporting layer may further include an n-type dopant. As the n-type dopant, those known in the art may be used, and for example, a metal or a metal complex may be used. According to an example, the electron transporting layer including the compound of Chemical Formula 1 may further include LiQ.

In still another exemplary embodiment, the organic light emitting device may be an organic light emitting device having a reverse-direction structure (inverted type) in which a negative electrode, an organic material layer having one or more layers, and a positive electrode are sequentially stacked on a substrate.

For example, the structure of the organic light emitting device of the present specification may have a structure as illustrated in FIGS. 1 and 2, but is not limited thereto.

FIG. 1 exemplifies the structure of an organic light emitting device 10 in which a first electrode 30, a light emitting layer 40, and a second electrode 50 are sequentially stacked on a substrate 20. FIG. 1 is an exemplified structure of the organic light emitting device according to an exemplary embodiment of the present specification, and may further include other organic material layers.

FIG. 2 exemplifies the structure of an organic light emitting device in which a first electrode 30, a hole injection layer 60, a hole transporting layer 70, an electron blocking layer 80, a light emitting layer 40, an electron transporting layer 90, an electron injection layer 100, and a second electrode 50 are sequentially stacked on a substrate 20. FIG. 2 is an exemplified structure according to exemplary embodiments of the present specification, and may further include other organic material layers.

According to an exemplary embodiment of the present specification, the organic material layer includes a light emitting layer, and the light emitting layer includes a compound represented by the following Chemical Formula 1-A.

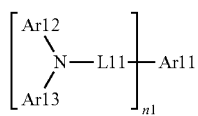

[Chemical Formula 1-A]

In Chemical Formula 1-A,
n1 is an integer of 1 or more,
Ar11 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L11 is a direct bond; a substituted or unsubstituted arylene group; or a substituted or unsubstituted heteroarylene group,
Ar12 and Ar13 are the same as or different from each other, and are each independently a substituted or unsubstituted aryl group; a substituted or unsubstituted silyl group; a substituted or unsubstituted alkyl group; a substituted or unsubstituted arylalkyl group; or a substituted or unsubstituted heteroaryl group, or may be bonded to each other to form a substituted or unsubstituted ring, and
when n1 is 2 or more, two or more structures in the parenthesis are the same as or different from each other.

According to an exemplary embodiment of the present specification, the organic material layer includes a light emitting layer, and the light emitting layer includes the compound represented by Chemical Formula 1-A as a dopant of the light emitting layer.

According to an exemplary embodiment of the present specification, L11 is a direct bond.

According to an exemplary embodiment of the present specification, n1 is 2.

In an exemplary embodiment of the present specification, Ar11 is a divalent pyrene group which is unsubstituted or substituted with deuterium, a methyl group, an ethyl group, or a tert-butyl group; or a divalent chrysene group which is unsubstituted or substituted with deuterium, a methyl group, an ethyl group, or a tert-butyl group.

According to an exemplary embodiment of the present specification, Ar12 and Ar13 are the same as or different from each other, and are each independently a substituted or unsubstituted aryl group having 6 to 30 carbon atoms.

According to an exemplary embodiment of the present specification, Ar12 and Ar13 are the same as or different from each other, and are each independently an aryl group which is unsubstituted or substituted with a silyl group substituted with a methyl group, an ethyl group, a tert-butyl group, a nitrile group, or an alkyl group.

According to an exemplary embodiment of the present specification, Ar12 and Ar13 are the same as or different from each other, and are each independently an aryl group which is unsubstituted or substituted with a silyl group substituted with an alkyl group.

According to an exemplary embodiment of the present specification, Ar12 and Ar13 are the same as or different from each other, and are each independently an aryl group which is unsubstituted or substituted with a trimethylsilyl group.

According to an exemplary embodiment of the present specification, Ar12 and Ar13 are the same as or different from each other, and are each independently a substituted or unsubstituted phenyl group; a substituted or unsubstituted biphenyl group; or a substituted or unsubstituted terphenyl group.

According to an exemplary embodiment of the present specification, Ar12 and Ar13 are the same as or different from each other, and are each independently a phenyl group which is unsubstituted or substituted with a methyl group, an ethyl group, a tert-butyl group, a nitrile group, or a trimethylsilyl group.

According to an exemplary embodiment of the present specification, Ar12 and Ar13 are the same as or different from each other, and are each independently a biphenyl group which is unsubstituted or substituted with a methyl group, an ethyl group, a tert-butyl group, a nitrile group, or a trimethylsilyl group.

According to an exemplary embodiment of the present specification, Ar12 and Ar13 are the same as or different from each other, and are each independently a terphenyl group which is unsubstituted or substituted with a methyl group, an ethyl group, a tert-butyl group, a nitrile group, or a trimethylsilyl group.

According to an exemplary embodiment of the present specification, Ar12 and Ar13 are the same as or different from each other, and are each independently a substituted or unsubstituted heteroaryl group having 6 to 30 carbon atoms.

According to an exemplary embodiment of the present specification, Ar12 and Ar13 are the same as or different from each other, and are each independently a heteroaryl group which is unsubstituted or substituted with a methyl group, an ethyl group, a tert-butyl group, a nitrile group, a silyl group substituted with an alkyl group, or a phenyl group.

According to an exemplary embodiment of the present specification, Ar12 and Ar13 are the same as or different from each other, and are each independently a dibenzofuran group which is unsubstituted or substituted with a methyl group, an ethyl group, a tert-butyl group, a nitrile group, a trimethylsilyl group, or a phenyl group.

According to an exemplary embodiment of the present specification, Chemical Formula 1-A is selected from the following compounds.

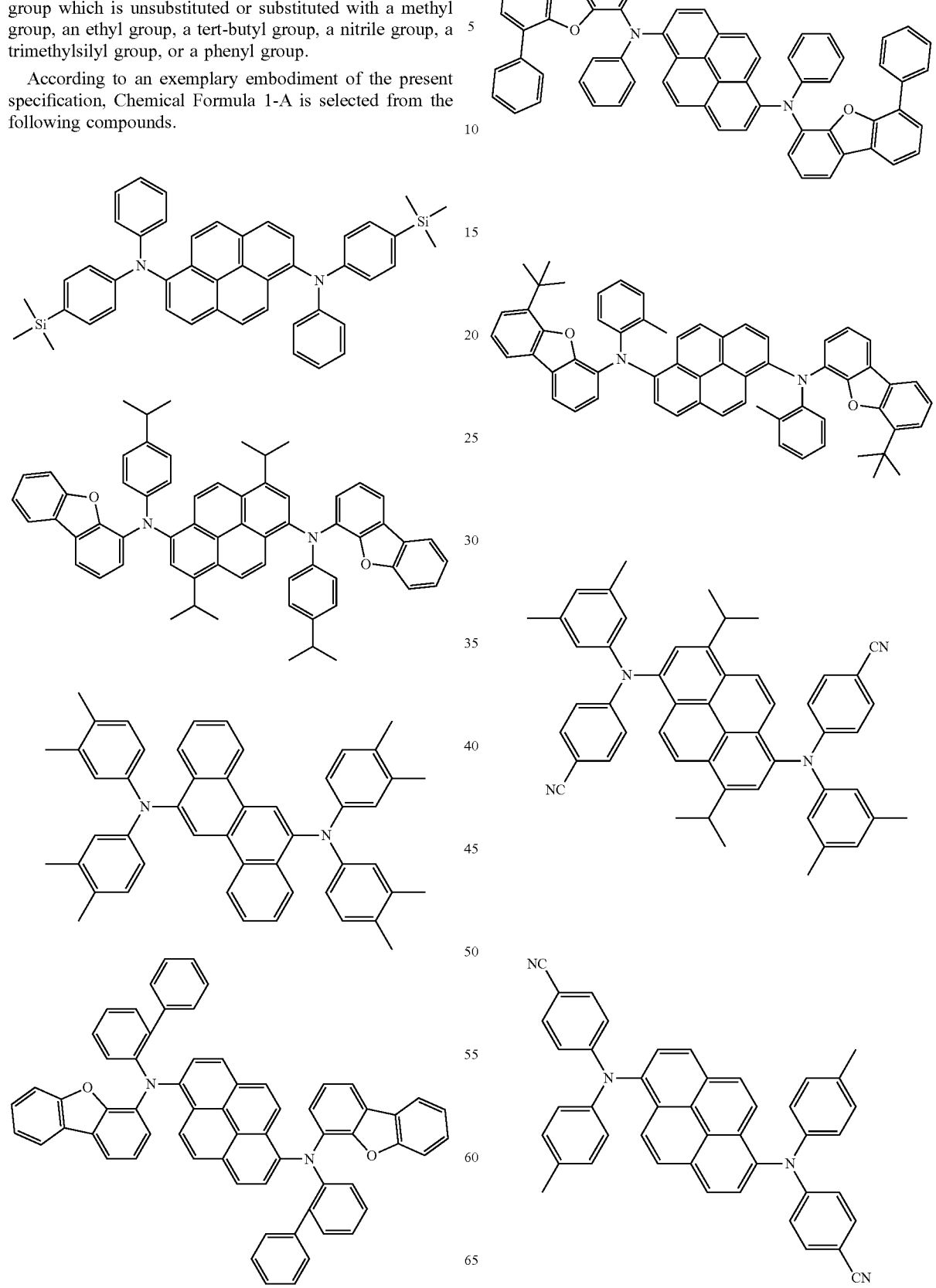

-continued

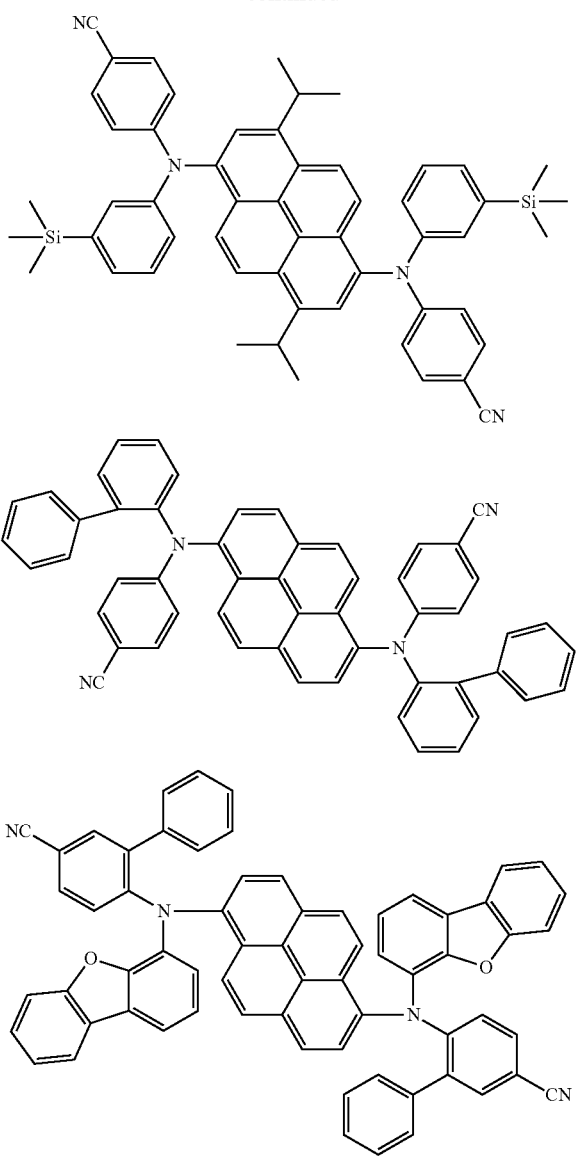

According to an exemplary embodiment of the present specification, the organic material layer includes a light emitting layer, and the light emitting layer includes a compound represented by the following Chemical Formula 2-A.

[Chemical Formula 2-A]

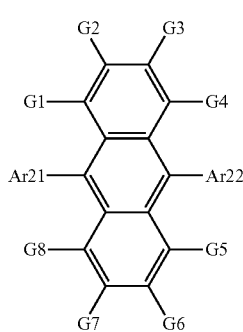

In Chemical Formula 2-A,

Ar21 and Ar22 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

According to an exemplary embodiment of the present specification, the organic material layer includes a light emitting layer, and the light emitting layer includes the compound represented by Chemical Formula 2-A as a host of the light emitting layer.

According to an exemplary embodiment of the present specification, Ar21 and Ar22 are the same as or different from each other, and are each independently a substituted or unsubstituted polycyclic aryl group.

According to an exemplary embodiment of the present specification, Ar21 and Ar22 are the same as or different from each other, and are each independently a substituted or unsubstituted polycyclic aryl group having 10 to 30 carbon atoms.

According to an exemplary embodiment of the present specification, Ar21 and Ar22 are the same as or different from each other, and are each independently a substituted or unsubstituted naphthyl group.

According to an exemplary embodiment of the present specification, Ar21 and Ar22 are the same as or different from each other, and are each independently a substituted or unsubstituted 1-naphthyl group.

According to an exemplary embodiment of the present specification, Ar21 and Ar22 are a 1-naphthyl group.

According to an exemplary embodiment of the present specification, G1 to G8 are hydrogen.

According to an exemplary embodiment of the present specification, Chemical Formula 2-A is selected from the following compound.

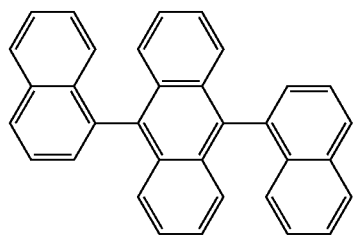 [SMILES: c1ccc2c(-c3c4ccccc4c(-c4cccc5ccccc45)c4ccccc34)cccc2c1]

According to an exemplary embodiment of the present specification, the organic material layer includes a light emitting layer, and the light emitting layer includes the compound represented by Chemical Formula 1-A as a dopant of the light emitting layer, and includes the compound represented by Chemical Formula 2-A as a host of the light emitting layer.

The organic light emitting device of the present specification may be manufactured by the materials and methods known in the art, except that one or more layers of the organic material layer include the compound of the present specification, that is, the compound.

When the organic light emitting device includes a plurality of organic material layers, the organic material layers may be formed of the same material or different materials.

The organic light emitting device of the present specification may be manufactured by the materials and methods known in the art, except that one or more layers of the organic material layer include the compound, that is, the compound represented by Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, materials having a large work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as $ZnO:Al$ or $SnO_2:Sb$; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a small work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material such as LiF/Al or $LiO_2$/Al; and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is a value between the work function of the positive electrode material and the HOMO of the neighboring organic material layer. Specific examples of the hole injection material include metal porphyrin, oligothiophene, an arylamine-based organic material, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The electron blocking layer is a layer which may improve the service life and efficiency of the device by preventing holes injected from a hole injection layer from passing through a light emitting layer and entering an electron injection layer, and may be formed at an appropriate portion between the light emitting layer and the electron injection layer using publicly-known materials, if necessary.

A light emitting material for the light emitting layer is a material which may emit light in a visible light region by accepting and combining holes and electrons from a hole transporting layer and an electron transporting layer, respectively, and is preferably a material having high quantum efficiency for fluorescence or phosphorescence. Specific examples thereof include: 8-hydroxy-quinoline-aluminum complex ($Alq_3$); carbazole-based compounds; dimerized styryl compounds; BAlq; 10-hydroxybenzoquinoline-metal compounds; benzoxazole-based, benzthiazole-based and benzimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a compound, a dibenzofuran derivative, a ladder-type furan compound, a pyrimidine derivative, and the like, but the examples are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting layer is a layer which accepts electrons from an electron injection layer and transports the electrons to a light emitting layer, and an electron transporting material is suitably a material having high electron mobility which may proficiently accept electrons from a negative electrode and transfer the electrons to a light emitting layer. Specific examples thereof include: Al complexes of 8-hydroxyquinoline; complexes including Alq$_3$; organic radical compounds; hydroxyflavone-metal complexes, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a negative electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the materials to be used.

In an exemplary embodiment of the present specification, the compound represented by Chemical Formula 1 may be included in an organic solar cell or an organic transistor in addition to the organic light emitting device.

The compound according to the present specification may act even in organic electronic devices including organic phosphorescent devices, organic solar cells, organic photoconductors, organic transistors, and the like, based on the principle similar to those applied to organic light emitting devices.

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

EXAMPLES

<Preparation Example 1>—Synthesis of Compound 1

1) Synthesis of Compound 1-A

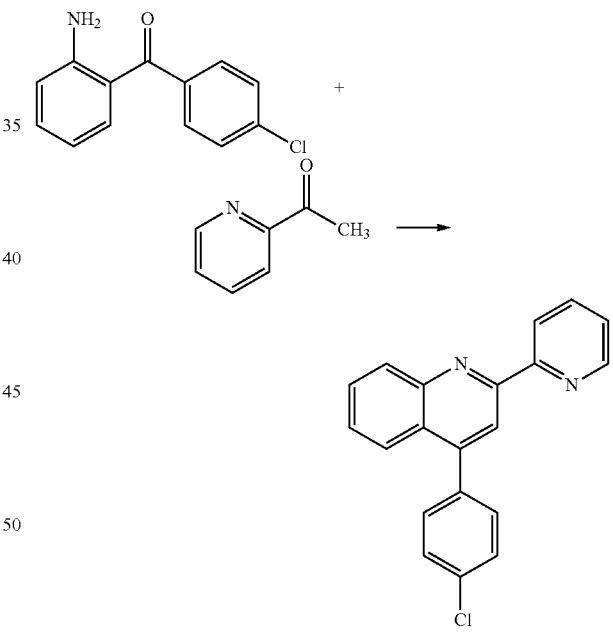

[Compound 1-A]

After (2-aminophenyl) (4-chlorophenyl)methanone (25.0 g, 107.9 mmol) and methyl pyridyl ketone (13.0 g, 107.9 mmol) were dissolved in 108 ml of acetic acid under a nitrogen atmosphere, 3 ml of anhydrous sulfuric acid was added thereto, and the resulting mixture was heated and stirred for 5 hours. The temperature was lowered to normal temperature, an extraction was performed with chloroform, and the extract was washed with water. After the moisture of the reactant was removed over anhydrous magnesium sulfate, the organic solvent was distilled and removed under reduced pressure, and the residue was washed with ethanol to prepare Compound 1-A (27 g, yield: 79.0%).

MS[M+H]$^+$=317

2) Synthesis of Compound 1-B

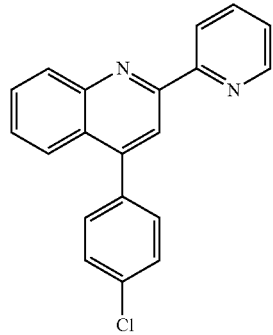

[Compound 1-A]

→

3) Synthesis of Compound 1

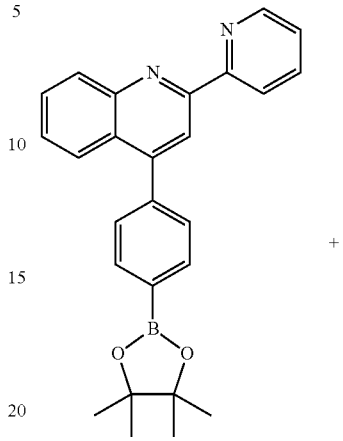

[Compound 1-B]

+

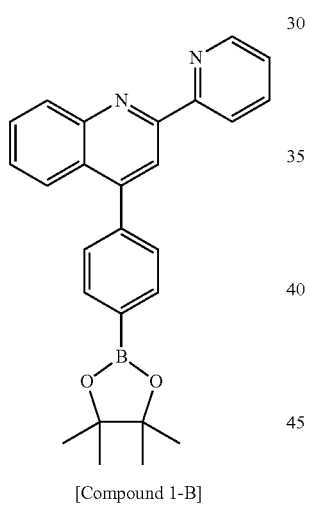

[Compound 1-B]

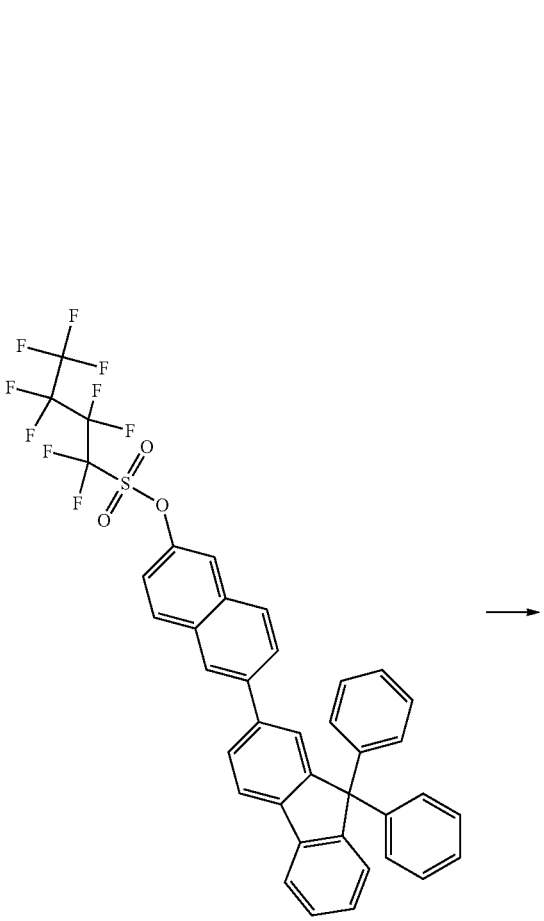

Compound 1-A (25.0 g, 78.9 mmol), bis(pinacolato) diboron (22.0 g, 86.8 mmol), and potassium acetate (20.9 g, 213.1 mmol) were mixed under a nitrogen atmosphere, and the resulting mixture was added to 100 ml of dioxane, and heated and stirred.
Bis(dibenzylidineacetone)palladium (1.4 g, 2.37 mmol) and tricyclohexylphosphine (1.3 g, 4.7 mmol) were put into the mixture while being refluxed, and the resulting mixture was stirred for 8 hours while being heated. After the reaction was terminated, the temperature was lowered to normal temperature, and then the mixture was filtered. The filtrate was added to water, an extraction was performed with chloroform, and the organic layer was dried over anhydrous magnesium sulfate. The organic layer was distilled under reduced pressure, and then washed with ethanol to prepare Compound 1-B (27 g, yield: 84%).

MS [M+H]$^+$=409

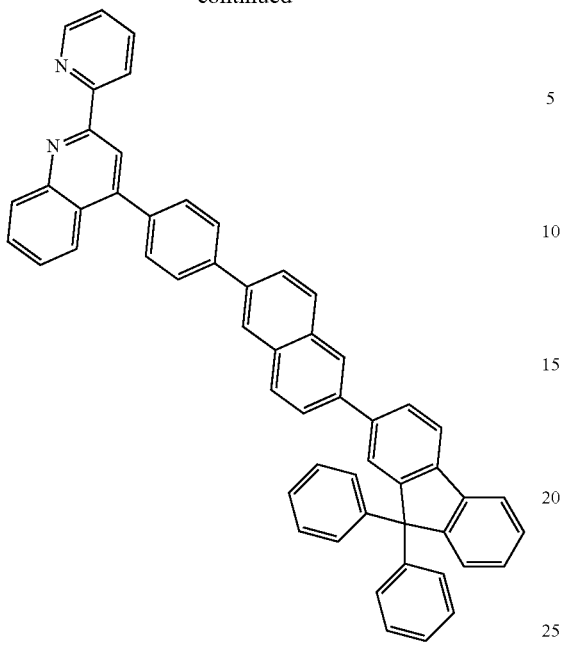

[Compound 1]

After Compound 1-B (20.0 g, 49.0 mmol) and 6-(9,9-diphenyl-2-fluorenyl)-2-naphthalenyl-nonafluorobutane-1-sulfonate (36.4 g, 49.0 mmol) were completely dissolved in tetrahydrofuran (50 ml), 30 ml of a 2 M aqueous potassium carbonate solution was added thereto, and tetrakistriphenylphosphinopalladium (1.7 g, 1.5 mmol) was put thereinto, and then the resulting mixture was stirred for 4 hours while being heated. The temperature was lowered to normal temperature, the reaction was terminated, and then the potassium carbonate solution was removed to filter the residue. The filtered solid was washed each once with tetrahydrofuran and ethanol to prepare Compound 1 (30.0 g, yield: 85%).

MS [M+H]$^+$=725

<Preparation Example 2>—Synthesis of Compound 2

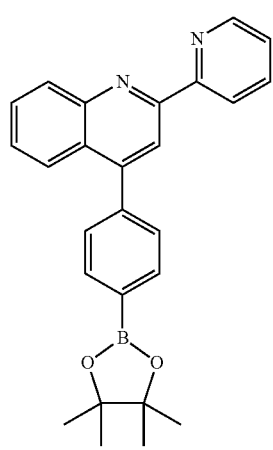

[Compound 1-B]

+

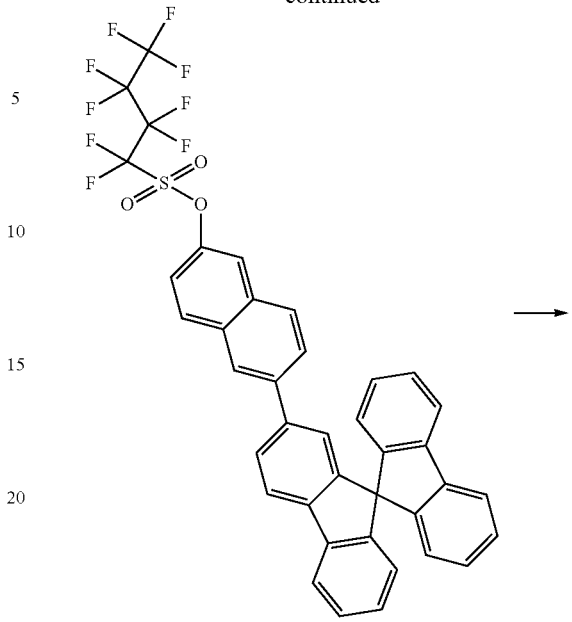

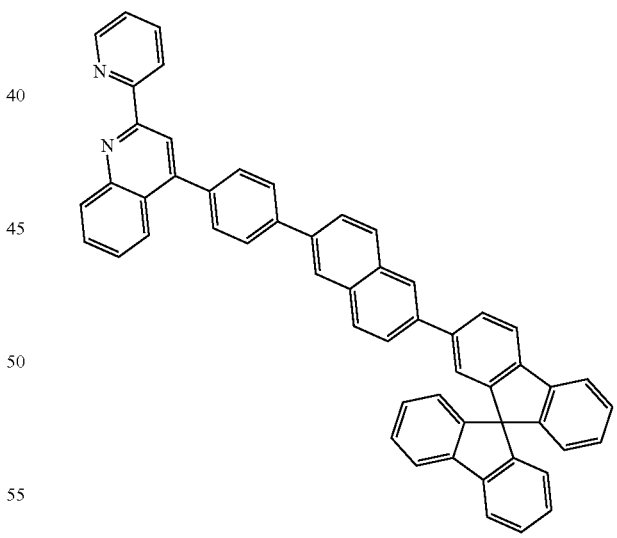

[Compound 2]

Compound 2 was prepared in the same manner as in the preparation method of Compound 1, except that 6-(9,9'-spirobi[fluoren]-2-yl)naphthalen-2-yl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.

MS [M+H]$^+$=723

<Preparation Example 3>—Synthesis of Compound 3

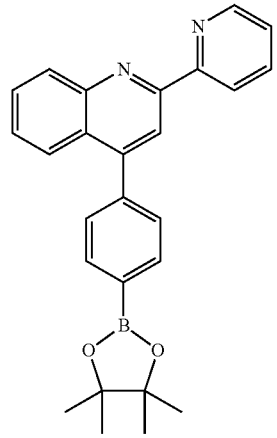

[Compound 1-B]

+

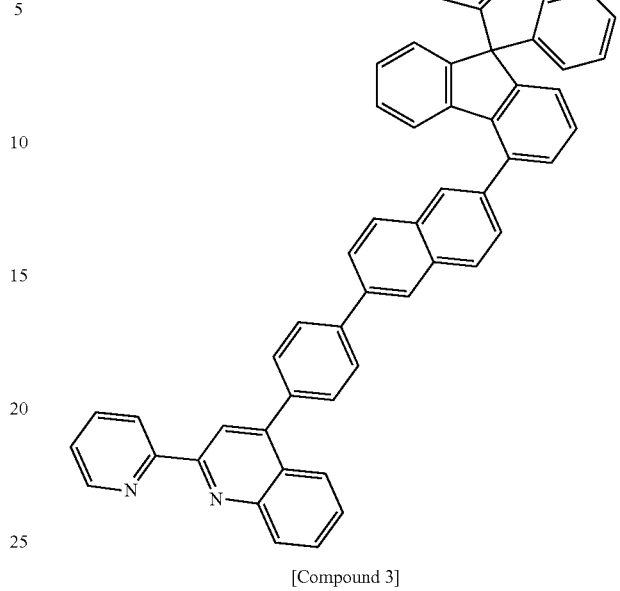

[Compound 3]

Compound 3 was prepared in the same manner as in the preparation method of Compound 1, except that 6-(9,9-diphenyl-9H-fluoren-4-yl)naphthalen-2-yl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.

MS [M+H]$^+$=725

<Preparation Example 4>—Synthesis of Compound 4

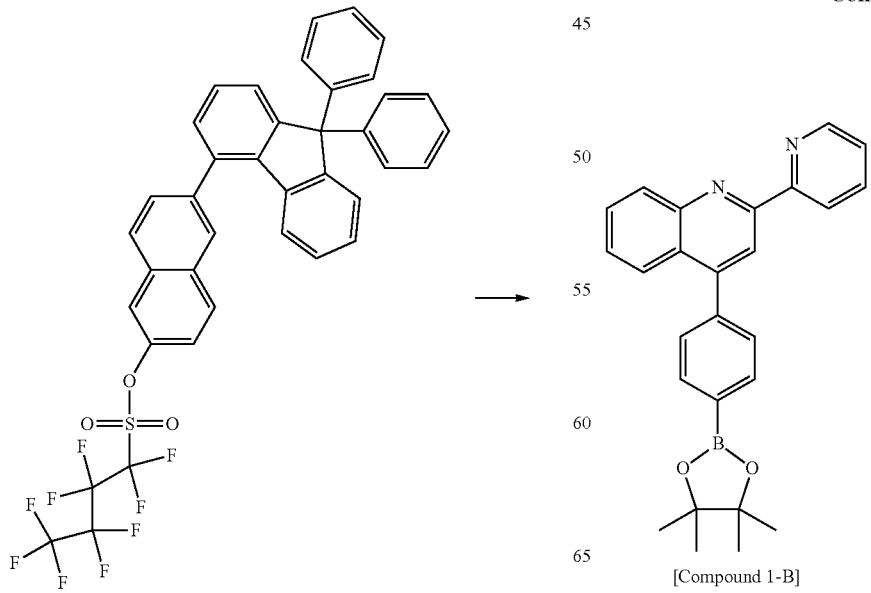

[Compound 1-B]

-continued
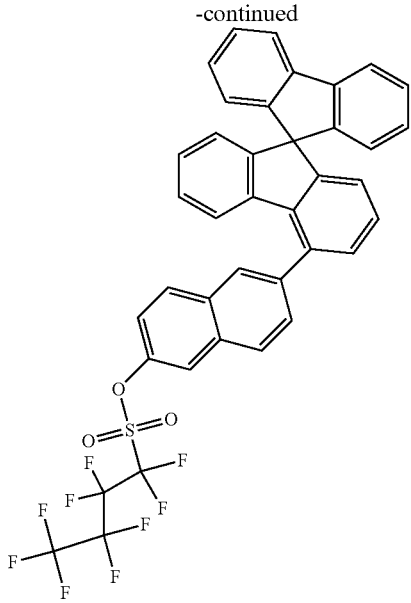
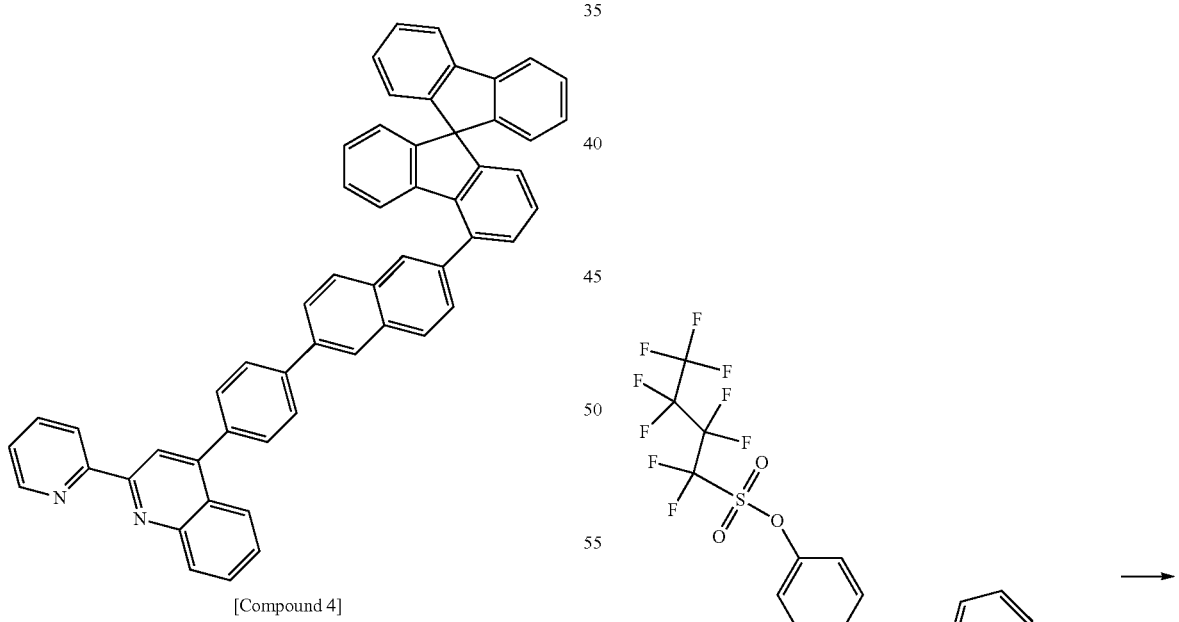
[Compound 4]
Compound 4 was prepared in the same manner as in the preparation method of Compound 1, except that 6-(9,9'-spirobi[fluoren]-4-yl)naphthalen-2-yl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.
MS [M+H]$^+$=723
<Preparation Example 5>—Synthesis of Compound 5
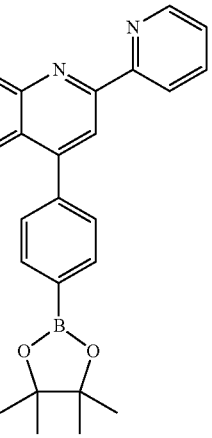
[Compound 1-B]
+

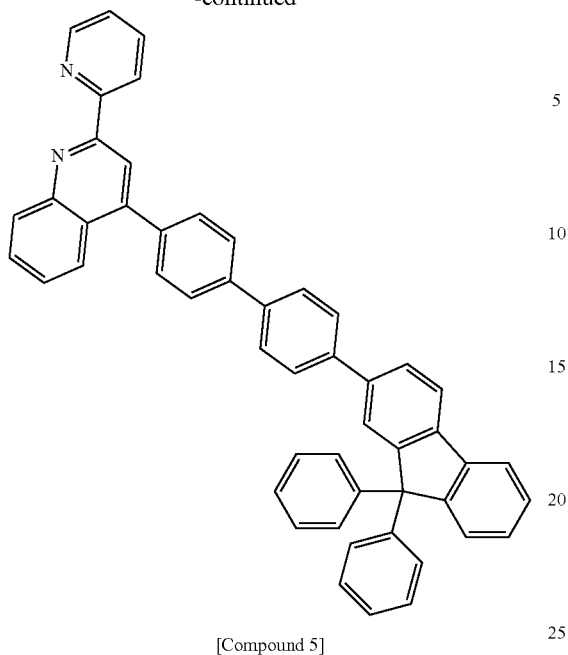

[Compound 5]

Compound 5 was prepared in the same manner as in the preparation method of Compound 1, except that 4-(9,9-diphenyl-9H-fluoren-2-yl)phenyl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.

MS [M+H]⁺=675

<Preparation Example 6>—Synthesis of Compound 8

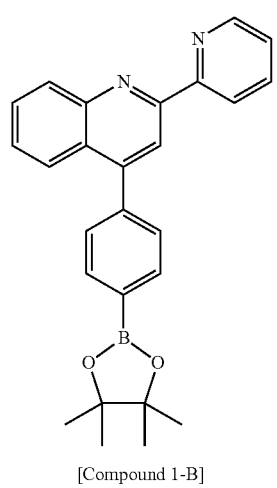

[Compound 1-B]

+

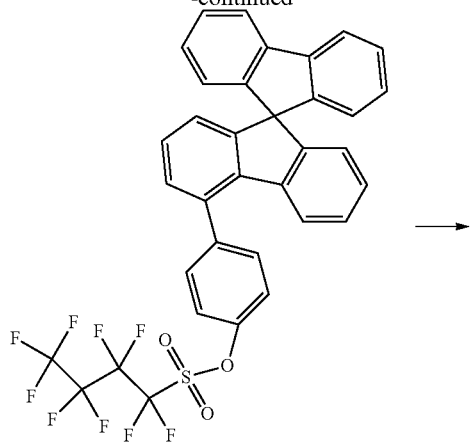

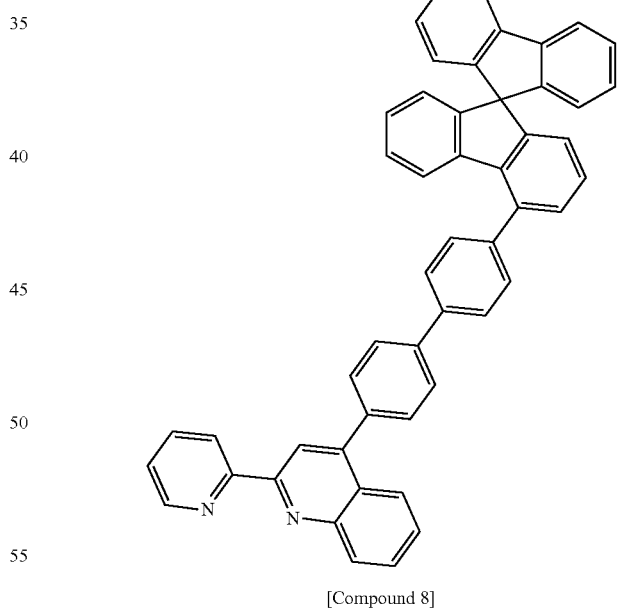

[Compound 8]

Compound 8 was prepared in the same manner as in the preparation method of Compound 1, except that 4-(9,9'-spirobi[fluoren]-4-yl)phenyl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.

MS [M+H]⁺=673

<Preparation Example 7>—Synthesis of Compound 9
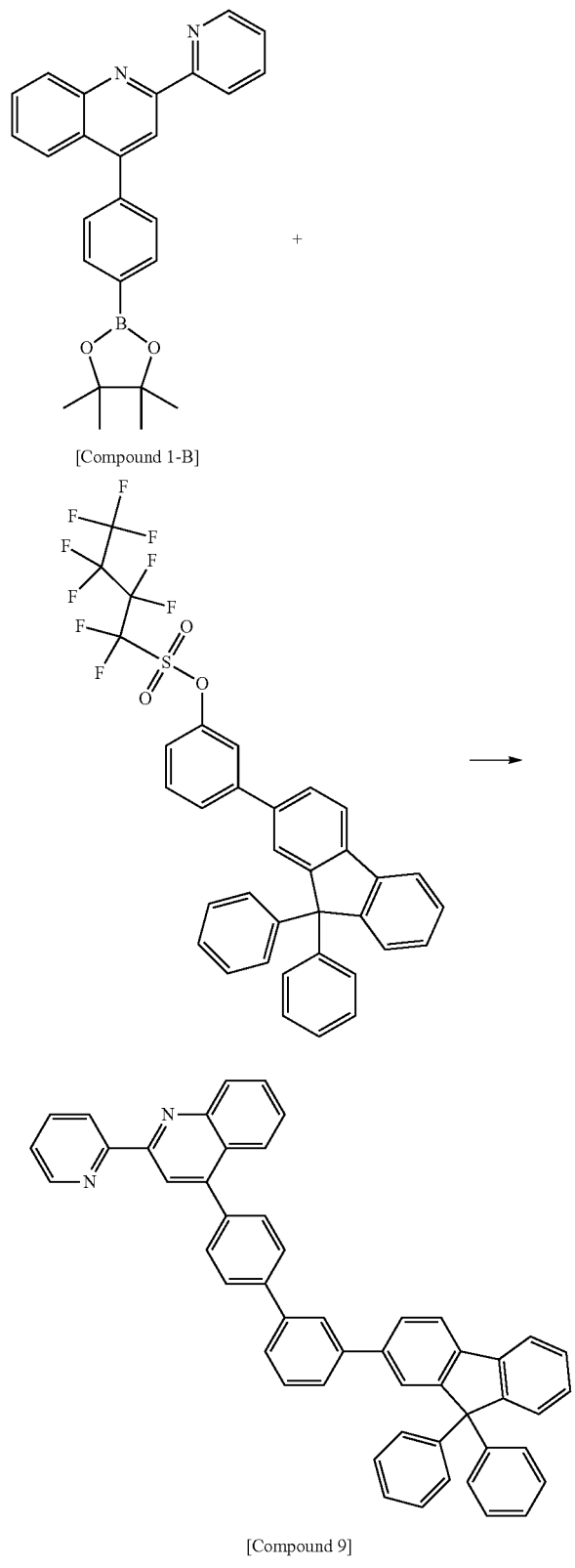
<Preparation Example 8>—Synthesis of Compound 12
Compound 9 was prepared in the same manner as in the preparation method of Compound 1, except that 3-(9,9-diphenyl-9H-fluoren-2-yl)phenyl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.
MS [M+H]$^+$=675
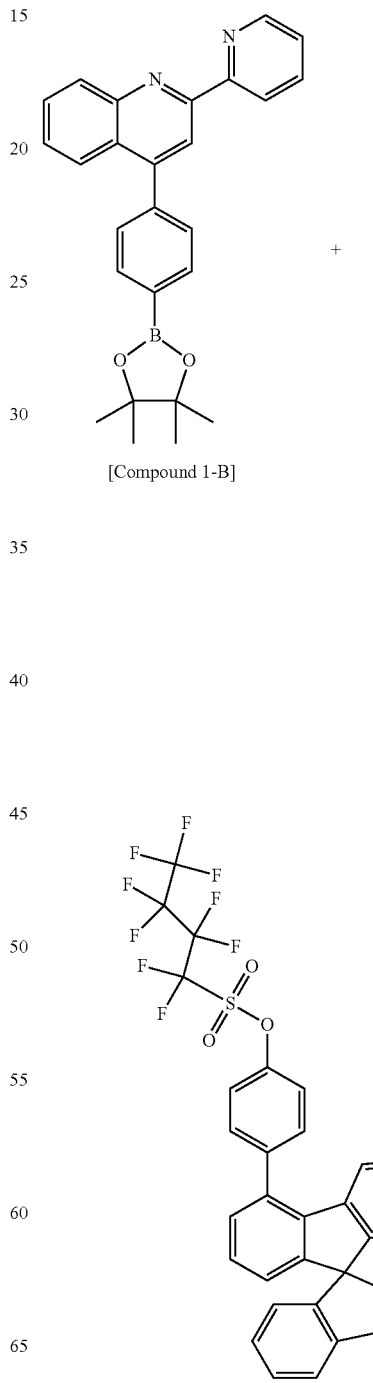

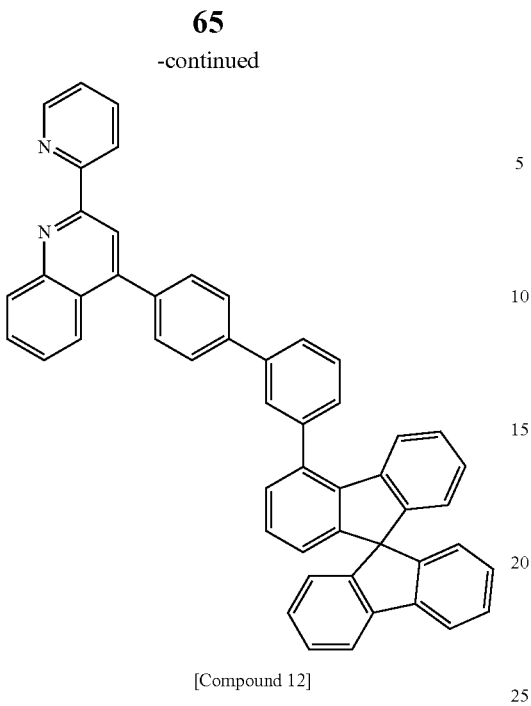

[Compound 12]

Compound 12 was prepared in the same manner as in the preparation method of Compound 1, except that 3-(9,9'-spirobi[fluoren]-4-yl)phenyl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.

MS [M+H]⁺=673

<Preparation Example 9>—Synthesis of Compound 13

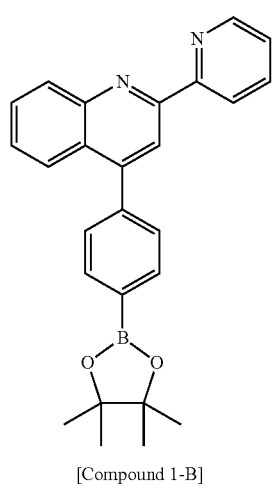

[Compound 1-B]

+

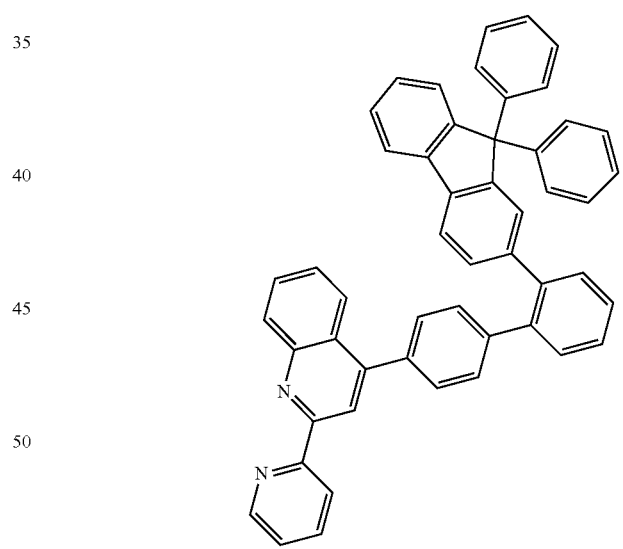

[Compound 13]

Compound 13 was prepared in the same manner as in the preparation method of Compound 1, except that 2-(9,9-diphenyl-9H-fluoren-2-yl)phenyl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.

MS [M+H]⁺=675

<Preparation Example 10>—Synthesis of Compound 17
Compound 17 was prepared in the same manner as in the preparation method of Compound 1, except that 7-(9,9-diphenyl-9H-fluoren-2-yl)naphthalen-2-yl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.
MS $[M+H]^+$=725
<Preparation Example 11>—Synthesis of Compound 18
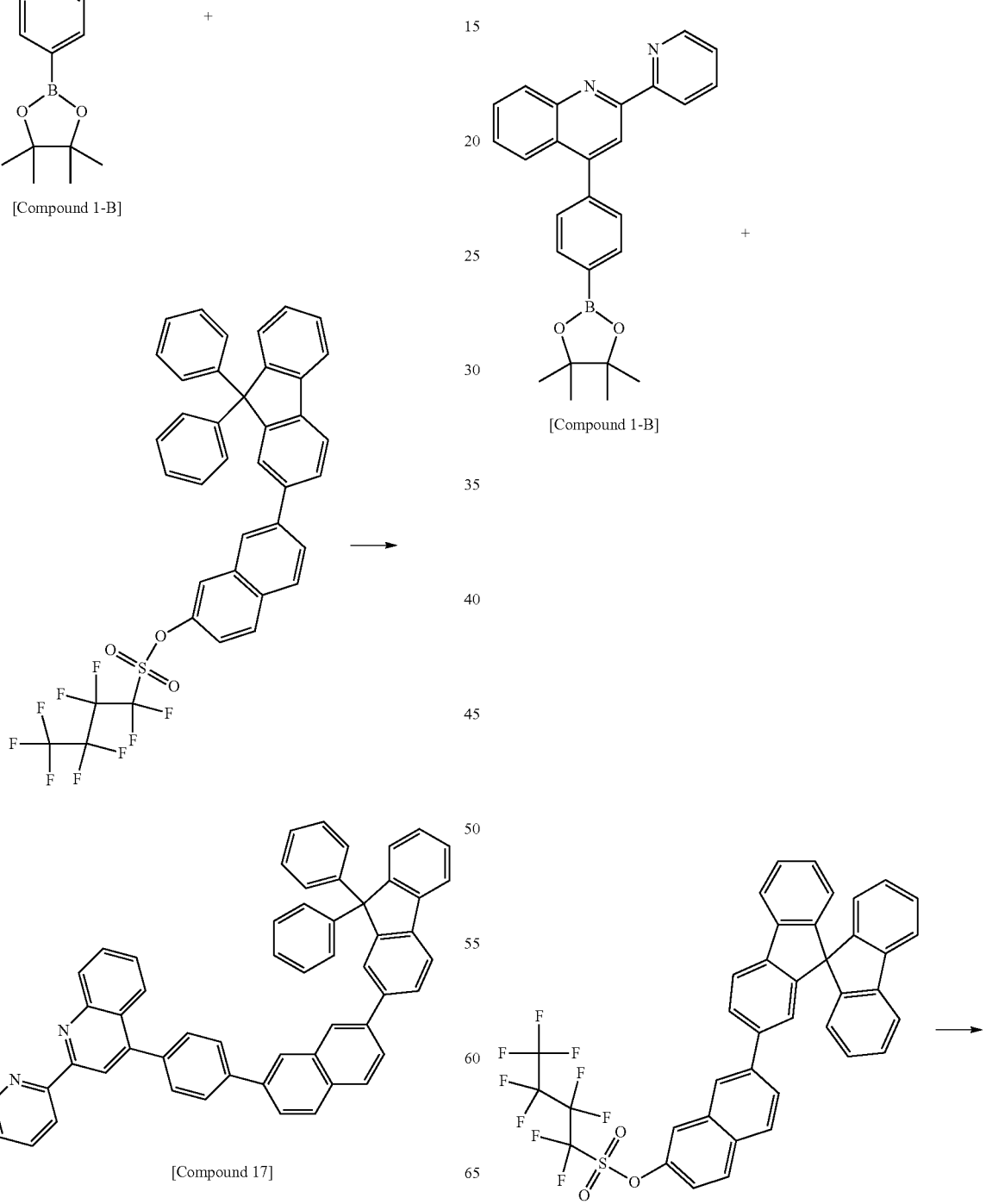

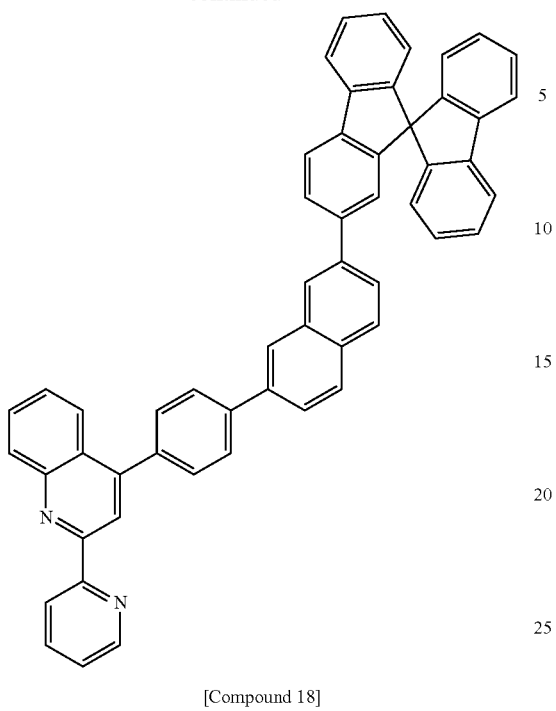

[Compound 18]

Compound 18 was prepared in the same manner as in the preparation method of Compound 1, except that 7-(9,9'-spirobi[fluoren]-2-yl)naphthalen-2-yl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.

MS [M+H]$^+$=723

<Preparation Example 12>—Synthesis of Compound 21

1) Synthesis of Compound 21-A

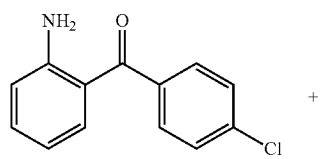

+

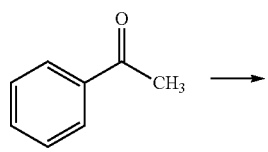

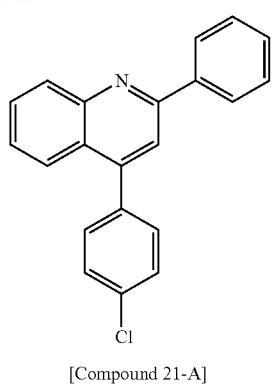

[Compound 21-A]

Compound 21-A was prepared in the same manner as in the preparation of Compound 1-A, except that acetophenone was used instead of methyl pyridyl ketone.

MS [M+H]$^+$=316

2) Synthesis of Compound 21-B

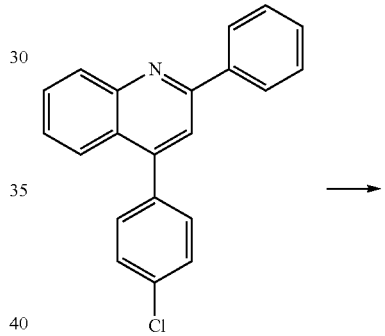

[Compound 21-A]

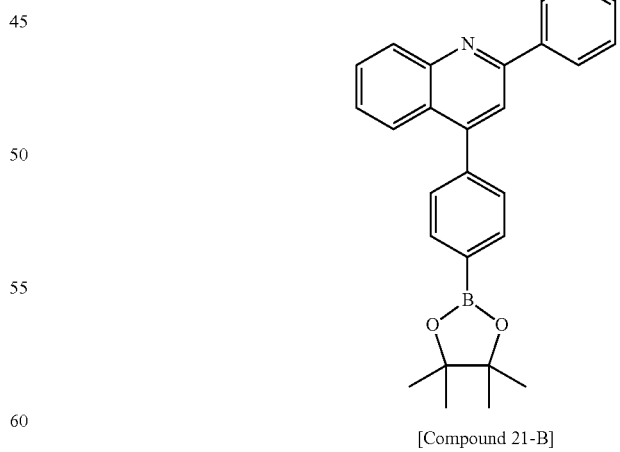

[Compound 21-B]

Compound 21-B was prepared in the same manner as in the preparation method of Compound 1-B, except that [Compound 21-A] was used instead of [Compound 1-A].

MS [M+H]$^+$=408

3) Synthesis of Compound 21
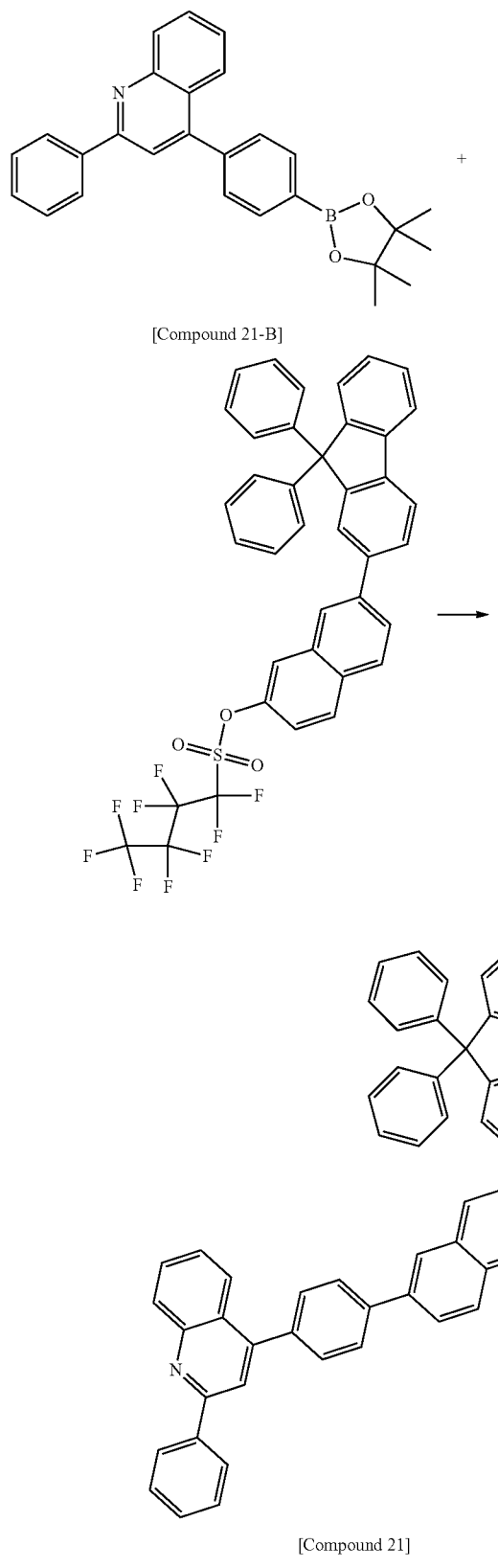
[Compound 21-B]
[Compound 21]
Compound 21 was prepared in the same manner as in the preparation method of Compound 17, except that Compound 21-B was used instead of Compound 1-B.
MS [M+H]$^+$=724
<Preparation Example 13>—Synthesis of Compound 22
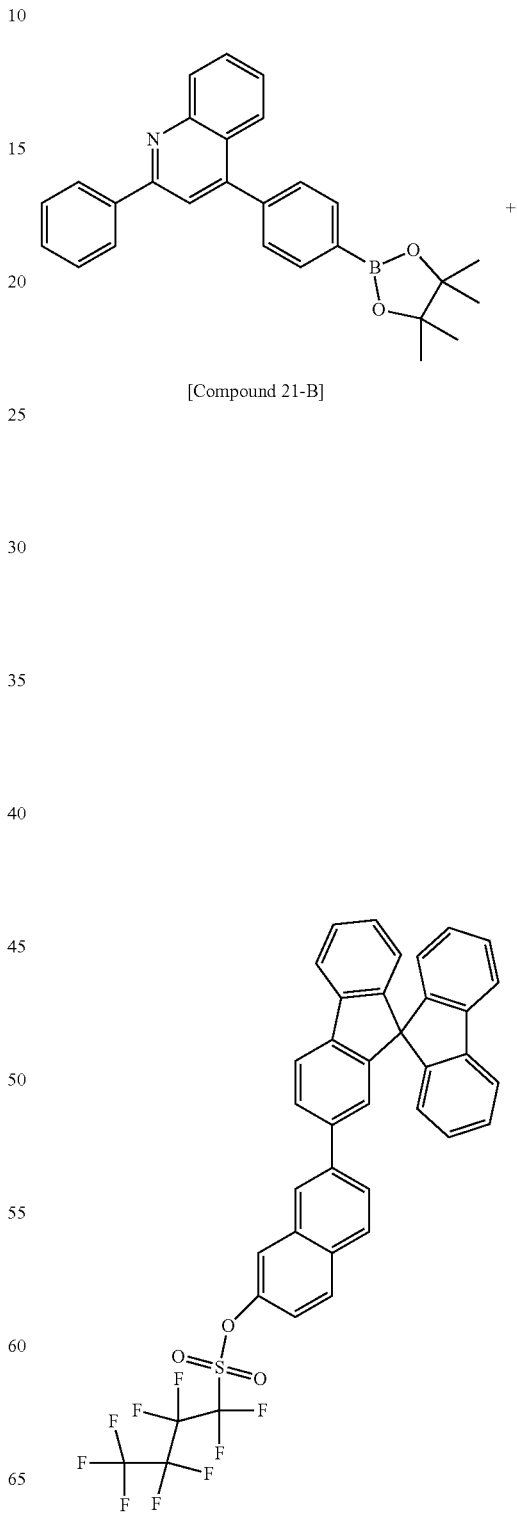
[Compound 21-B]

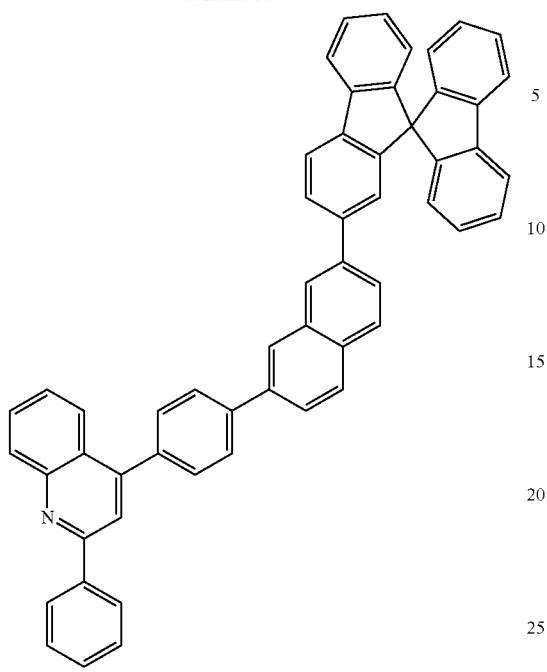

[Compound 22]

Compound 22 was prepared in the same manner as in the preparation method of Compound 21, except that 7-(9,9'-spirobi[fluoren]-2-yl)naphthalen-2-yl 1,1,2,2,3,3,4,4,4-nonafluorobutan-1-sulfonate was used instead of 7-(9,9-diphenyl-9H-fluoren-2-yl)naphthalen-2-yl 1,1,2,2,3,3,4,4,4-nonafluorobutane-1-sulfonate.

MS [M+H]$^+$=722

<Preparation Example 14>—Synthesis of Compound 25

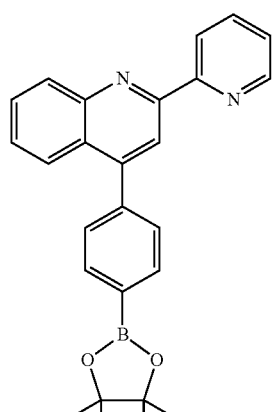

[Compound 1-B]

+

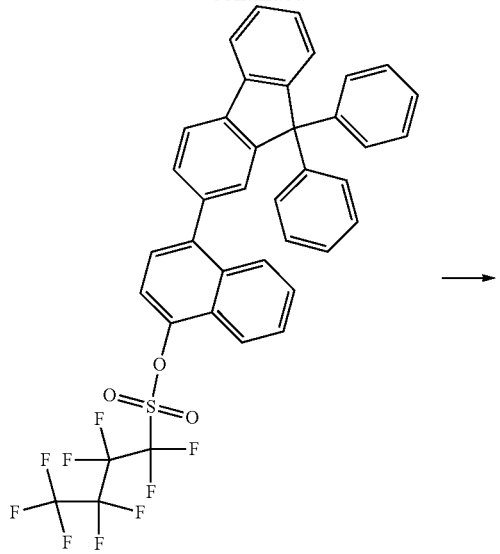

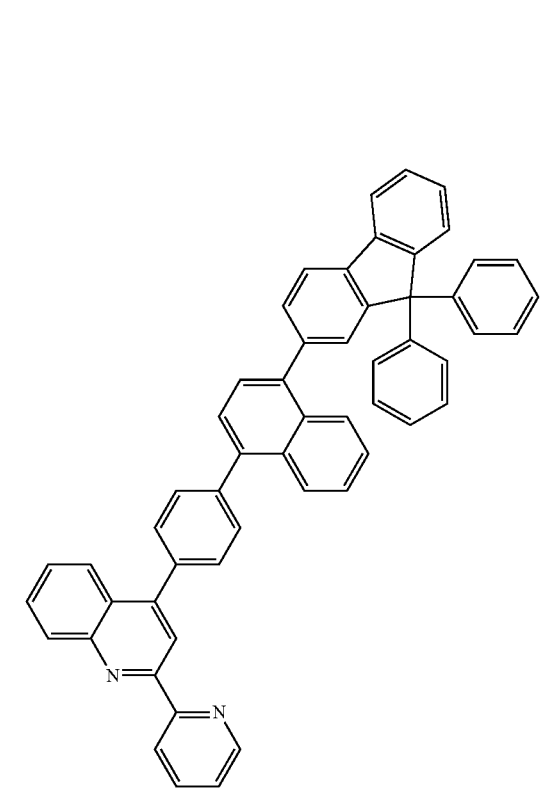

[Compound 25]

Compound 25 was prepared in the same manner as in the preparation method of Compound 1, except that 4-(9,9-diphenyl-9H-fluoren-2-yl)naphthalen-1-yl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.

MS [M+H]$^+$=725

<Preparation Example 15>—Synthesis of Compound 33

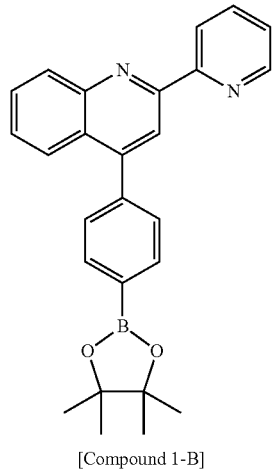

[Compound 1-B]

+

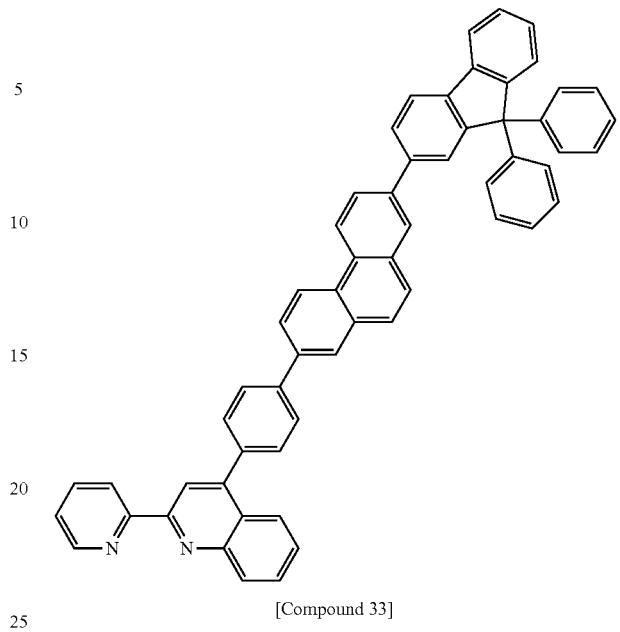

[Compound 33]

Compound 33 was prepared in the same manner as in the preparation method of Compound 1, except that 7-(9,9-diphenyl-9H-fluoren-2-yl)phenanthren-2-yl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.

MS [M+H]$^+$=775

<Preparation Example 16>—Synthesis of Compound 34

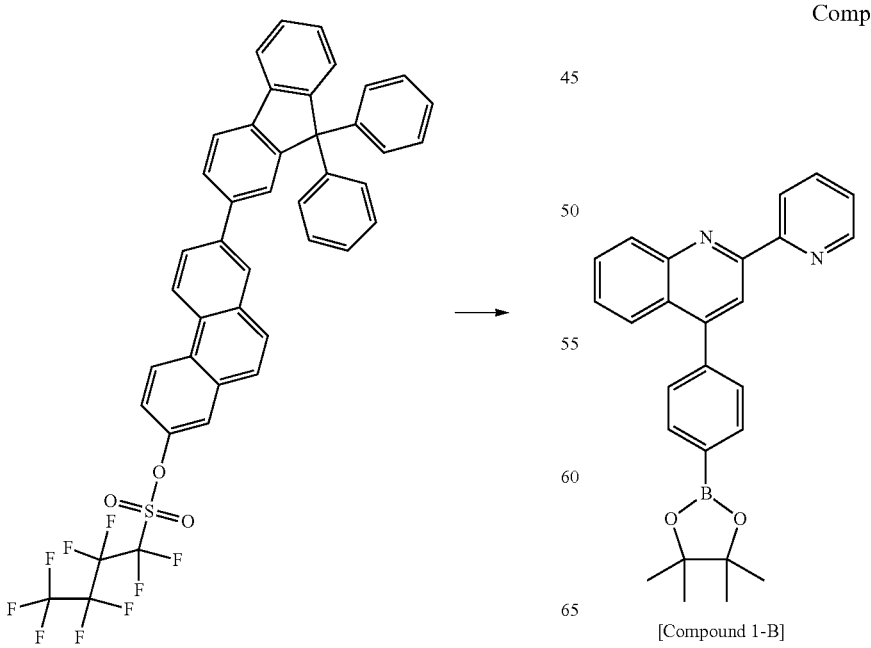

[Compound 1-B]

-continued

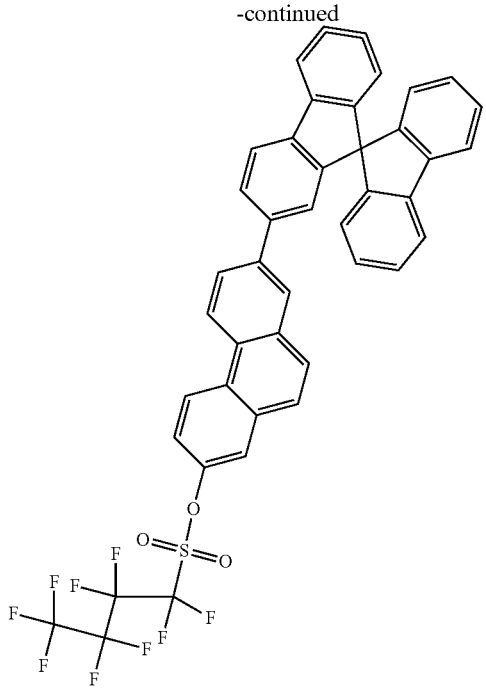

[Compound 34]

Compound 34 was prepared in the same manner as in the preparation method of Compound 1, except that 7-(9,9'-spirobi[fluoren]-2-yl)phenanthren-2-yl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.

MS [M+H]$^+$=773

<Preparation Example 17>—Synthesis of Compound 45

1) Synthesis of Compound 45-A

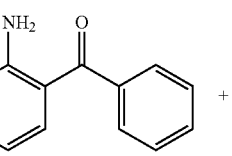

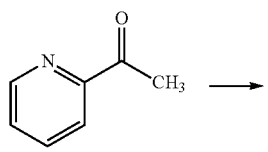

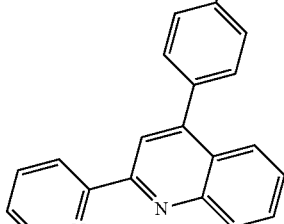

[Compound 45-A]

Compound 45-A was prepared in the same manner as in the preparation method of Compound 1-A, except that (2-amino-4-chlorophenyl) (phenyl)methanone was used instead of 2-aminophenyl-4-chlorophenylmethanone.

MS [M+H]$^+$=317

2) Synthesis of Compound 45-B

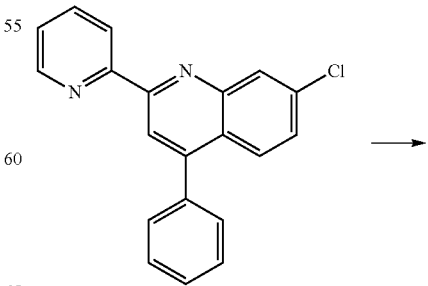

[Compound 45-A]

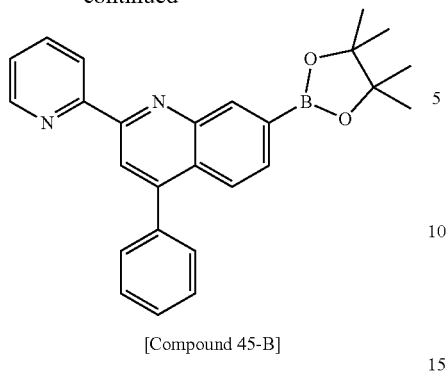

[Compound 45-B]

Compound 45-B was prepared in the same manner as in the preparation method of Compound 1-B, except that [Compound 45-A] was used instead of [Compound 1-A].

MS [M+H]$^+$=409

3) Synthesis of Compound 45

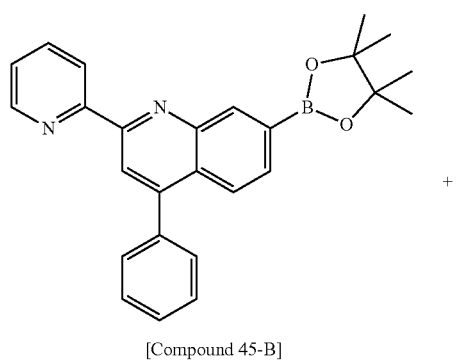

[Compound 45-B]

+

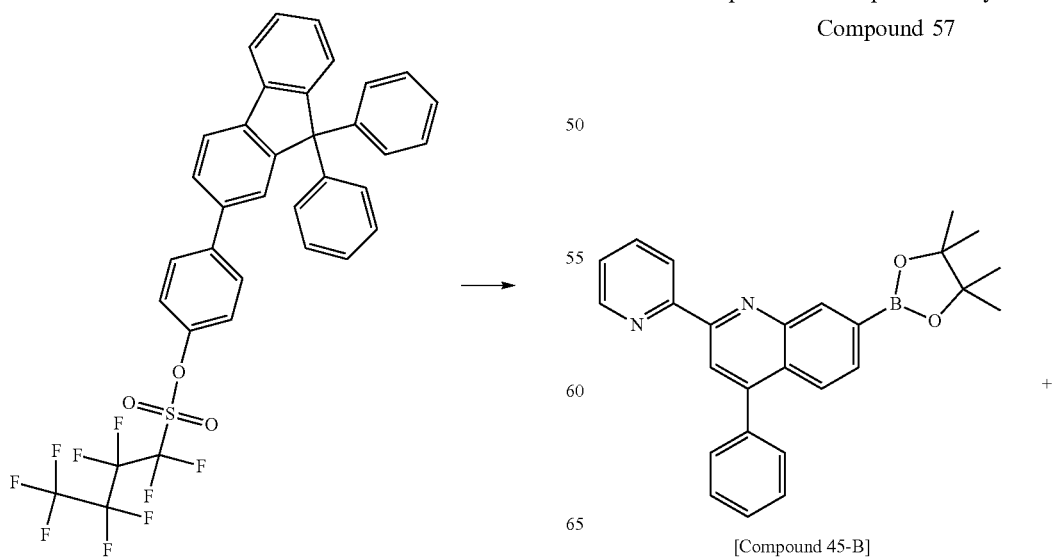

[Compound 45]

Compound 45 was prepared in the same manner as in the preparation method of Compound 1, except that [Compound 45-B] was used instead of [Compound 1-B], and 4-(9,9-diphenyl-9H-fluoren-2-yl)phenyl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.

MS [M+H]$^+$=675

<Preparation Example 18>—Synthesis of Compound 57

-continued

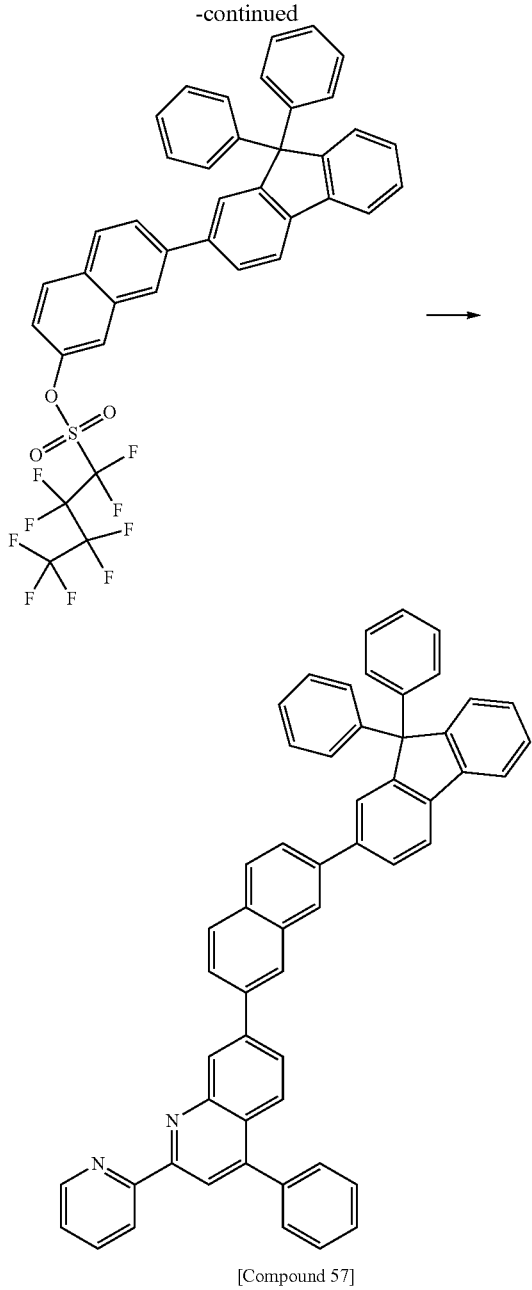

[Compound 57]

Compound 57 was prepared in the same manner as in the preparation method of Compound 1, except that [Compound 45-B] was used instead of [Compound 1-B], and 7-(9,9-diphenyl-9H-fluoren-2-yl)naphthalen-2-yl 1,1,2,2,3,3,4,4,4-nonafluorobutane-1-sulfonate was used instead of 6-(9,9-diphenyl-2-fluorenyl)-2-naphthalenyl-nonafluorobutane-1-sulfonate.

MS $[M+H]^+$=725

EXAMPLES

Example 1

A glass substrate (Corning glass) thinly coated with ITO (indium tin oxide) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted.

Hexanitrile hexaazatriphenylene was thermally vacuum deposited to have a thickness of 500 Å on a transparent ITO electrode, which was thus prepared, thereby forming a hole injection layer. HT1 (400 Å), which is a material transporting holes, was vacuum deposited thereon, and then compounds of a host H1 and a dopant D1 were vacuum deposited as a light emitting layer to have a thickness of 300 Å. Compound 1 prepared in Preparation Example 1 and LiQ (lithium quinolate) were vacuum deposited at a weight ratio of 1:1 on the light emitting layer, thereby forming an electron injection and transporting layer having a thickness of 350 Å.

Lithium fluoride (LiF) and aluminum were sequentially deposited on the electron injection and transporting layer to have a thickness of 12 Å and 2,000 Å, respectively, thereby forming a negative electrode. An organic light emitting device was manufactured.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

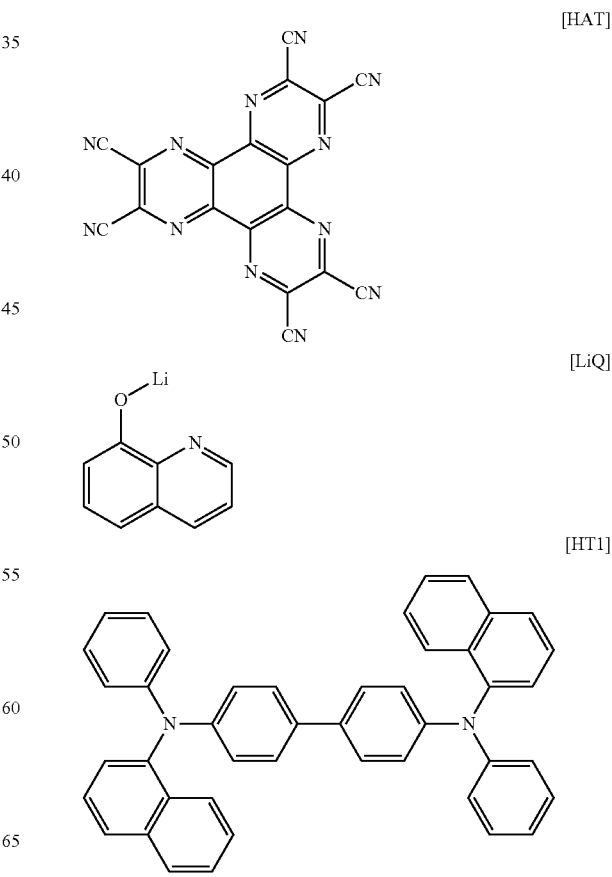

[H1]

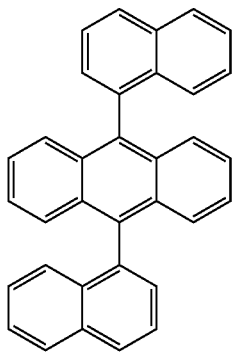

[D1]

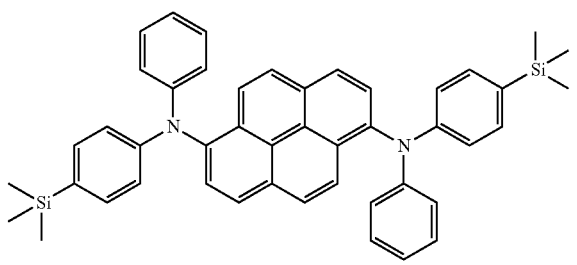

Example 2

An experiment was performed in the same manner as in Example 1, except that as the electron injection and transporting layer, Compound 2 was used instead of Compound 1.

Example 3

An experiment was performed in the same manner as in Example 1, except that as the electron injection and transporting layer, Compound 3 was used instead of Compound 1.

Example 4

An experiment was performed in the same manner as in Example 1, except that as the electron injection and transporting layer, Compound 4 was used instead of Compound 1.

Example 5

An experiment was performed in the same manner as in Example 1, except that as the electron injection and transporting layer, Compound 5 was used instead of Compound 1.

Example 6

An experiment was performed in the same manner as in Example 1, except that as the electron injection and transporting layer, Compound 8 was used instead of Compound 1.

Example 7

An experiment was performed in the same manner as in Example 1, except that as the electron injection and transporting layer, Compound 9 was used instead of Compound 1.

Example 8

An experiment was performed in the same manner as in Example 1, except that as the electron injection and transporting layer, Compound 12 was used instead of Compound 1.

Example 9

An experiment was performed in the same manner as in Example 1, except that as the electron injection and transporting layer, Compound 13 was used instead of Compound 1.

Example 10

An experiment was performed in the same manner as in Example 1, except that as the electron injection and transporting layer, Compound 17 was used instead of Compound 1.

Example 11

An experiment was performed in the same manner as in Example 1, except that as the electron injection and transporting layer, Compound 18 was used instead of Compound 1.

Example 12

An experiment was performed in the same manner as in Example 1, except that as the electron injection and transporting layer, Compound 21 was used instead of Compound 1.

Example 13

An experiment was performed in the same manner as in Example 1, except that as the electron injection and transporting layer, Compound 22 was used instead of Compound 1.

Example 14

An experiment was performed in the same manner as in Example 1, except that as the electron injection and transporting layer, Compound 25 was used instead of Compound 1.

Example 15

An experiment was performed in the same manner as in Example 1, except that as the electron injection and transporting layer, Compound 33 was used instead of Compound 1.

Example 16

An experiment was performed in the same manner as in Example 1, except that as the electron injection and transporting layer, Compound 34 was used instead of Compound 1.

Example 17

An experiment was performed in the same manner as in Example 1, except that as the electron injection and transporting layer, Compound 45 was used instead of Compound 1.

Example 18

An experiment was performed in the same manner as in Example 1, except that as the electron injection and transporting layer, Compound 57 was used instead of Compound 1.

Comparative Example 1

An experiment was performed in the same manner as in Example 1, except that as the electron injection and transporting layer, the following compound ET1 was used instead of Compound 1.

[ET1]

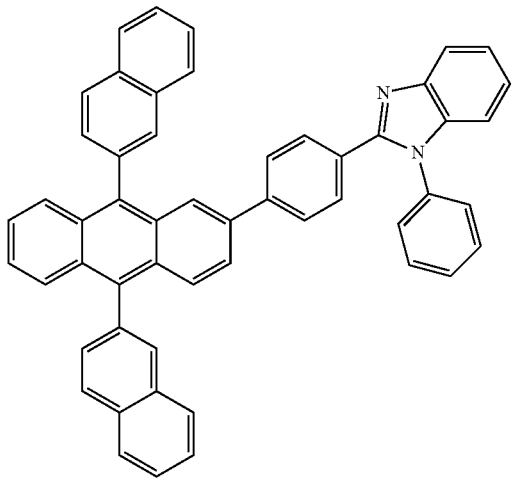

Comparative Example 2

An experiment was performed in the same manner as in Example 1, except that as the electron injection and transporting layer, the following compound ET2 was used instead of Compound 1.

[ET2]

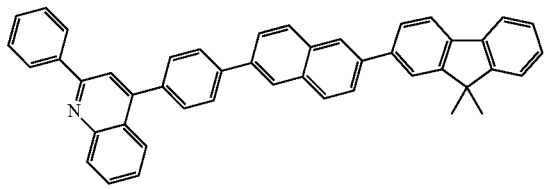

When current was applied to the organic light emitting devices manufactured in Examples 1 to 18 and Comparative Examples 1 to 2, the results of the following Table 1 were obtained.

TABLE 1

| Example 10 mA/cm$^2$ | Compound (Electron transporting layer) | Voltage (V) | Current efficiency (cd/A) | Color coordinate (x, y) | Life Time (98 at 20 mA/cm$^2$) |
|---|---|---|---|---|---|
| Example 1 | 1 | 3.84 | 5.29 | (0.137, 0.127) | 49 |
| Example 2 | 2 | 3.76 | 5.28 | (0.137, 0.127) | 48 |
| Example 3 | 3 | 3.74 | 5.27 | (0.138, 0.127) | 46 |
| Example 4 | 4 | 3.85 | 5.12 | (0.137, 0.126) | 40 |
| Example 5 | 5 | 3.87 | 5.09 | (0.136, 0.127) | 41 |
| Example 6 | 8 | 3.85 | 5.10 | (0.136, 0.126) | 40 |
| Example 7 | 9 | 3.90 | 5.05 | (0.136, 0.126) | 42 |
| Example 8 | 12 | 3.91 | 5.10 | (0.136, 0.127) | 43 |
| Example 9 | 13 | 3.87 | 5.13 | (0.136, 0.126) | 40 |
| Example 10 | 17 | 3.85 | 5.27 | (0.137, 0.127) | 45 |
| Example 11 | 18 | 3.84 | 5.26 | (0.137, 0.127) | 45 |
| Example 12 | 21 | 3.77 | 5.04 | (0.136, 0.127) | 39 |
| Example 13 | 22 | 3.78 | 5.05 | (0.137, 0.126) | 40 |
| Example 14 | 25 | 3.82 | 5.28 | (0.137, 0.127) | 47 |
| Example 15 | 33 | 3.90 | 5.24 | (0.136, 0.127) | 49 |
| Example 16 | 34 | 3.88 | 5.25 | (0.140, 0.129) | 48 |
| Example 17 | 45 | 3.92 | 5.11 | (0.139, 0.130) | 43 |
| Example 18 | 57 | 3.93 | 5.12 | (0.139, 0.130) | 44 |
| Comparative Example 1 | ET 1 | 4.33 | 4.89 | (0.140, 0.129) | 26 |
| Comparative Example 2 | ET 2 | 4.05 | 4.99 | (0.139, 0.130) | 32 |

As shown in Table 1, it can be seen that the organic light emitting device manufactured by using the compound represented by Chemical Formula 1 of the present specification as the electron injection and transporting layer exhibits excellent characteristics in terms of efficiency, driving voltage, and/or stability of the organic light emitting device.

Specifically, it can be confirmed that the compound having the structure represented by Chemical Formula 1 of the present specification has more improved voltage, efficiency, and service life characteristics as compared to the existing electron transporting layer material in Comparative Example 1, and it can be confirmed that the aromatic or fused-fluorene structure of the compound represented by Chemical Formula 1 has more improved low-voltage characteristics and efficiency characteristics by electronically rich material characteristics and shows more thermally stable characteristics, as compared to the organic light emitting device of Comparative Example 2 manufactured by using the compound having the alkyl-fluorene structure as the electron injection and transporting layer.

Although the preferred exemplary embodiments (an electron injection and transporting layer) of the present invention have been described above, the present invention is not limited thereto, and various modifications can be made and carried out within the scope of the claims and the detailed description of the invention, and also fall within the scope of the invention.

The invention claimed is:

1. A compound represented by the following Chemical Formula 1:

[Chemical Formula 1]

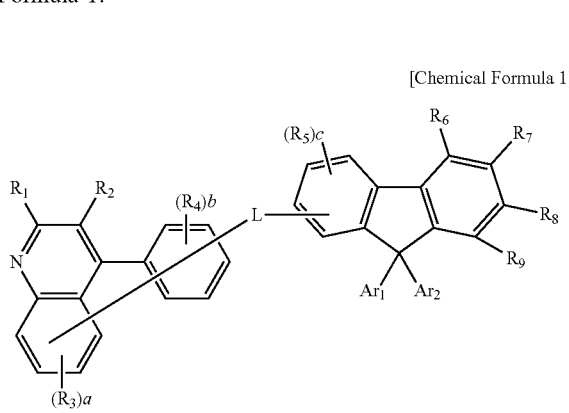

in Chemical Formula 1,

L is a direct bond; or a substituted or unsubstituted arylene group, $Ar_1$ and $Ar_2$ are the same as or different from each other, and are each independently hydrogen; deuterium; a substituted or unsubstituted cycloalkyl group; a substituted or unsubstituted aryl group; or a substituted or unsubstituted heteroaryl group, or are optionally bonded to an adjacent group to form a ring, $R_1$ is a substituted or unsubstituted alkyl group; a substituted or unsubstituted cycloalkyl group; a substituted or unsubstituted aryl group; or a substituted or unsubstituted heteroaryl group, $R_2$ to $R_9$ are the same as or different from each other, and are each independently hydrogen; deuterium; a substituted or unsubstituted alkyl group; a substituted or unsubstituted cycloalkyl group; a substituted or unsubstituted aryl group; or a substituted or unsubstituted heteroaryl group, a is an integer from 1 to 4, b is an integer from 1 to 5, c is an integer from 1 to 3, a+b is an integer from 2 to 8, and when a to c are each 2 or more, structures in the parenthesis are the same as or different from each other.

2. The compound of claim 1, wherein Chemical Formula 1 is represented by the following Chemical Formula 2 or 3:

[Chemical Formula 2]

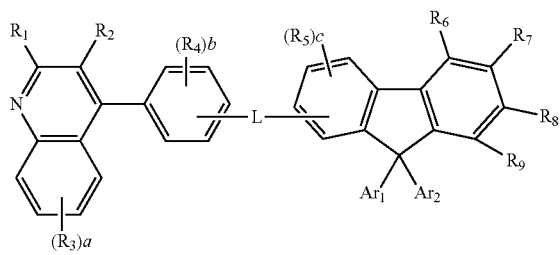

[Chemical Formula 3]

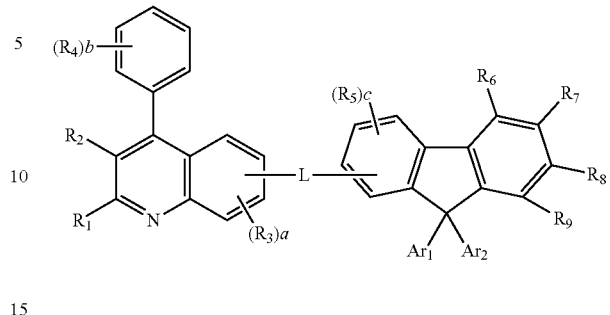

in Chemical Formulae 2 and 3,

L, $Ar_1$, $Ar_2$, $R_1$ to $R_9$, and a to c are the same as those defined in Chemical Formula 1.

3. The compound of claim 1, wherein Chemical Formula 1 is represented by any one of the following Chemical Formulae 4 to 9:

[Chemical Formula 4]

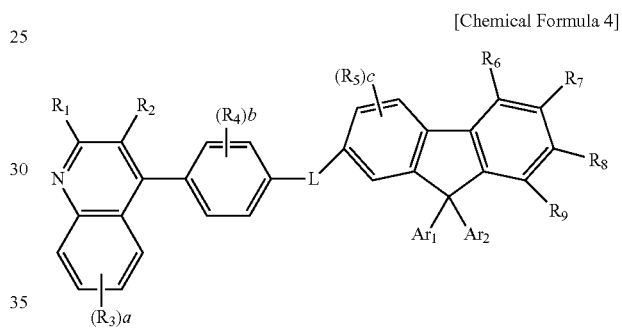

[Chemical Formula 5]

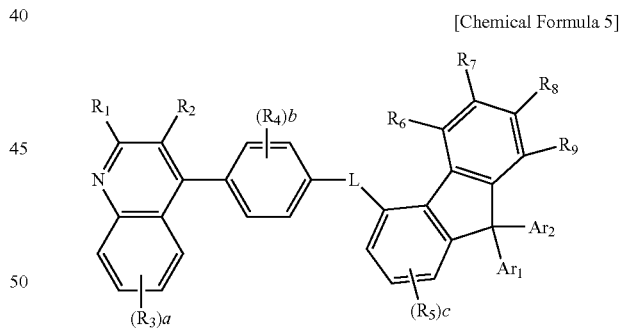

[Chemical Formula 6]

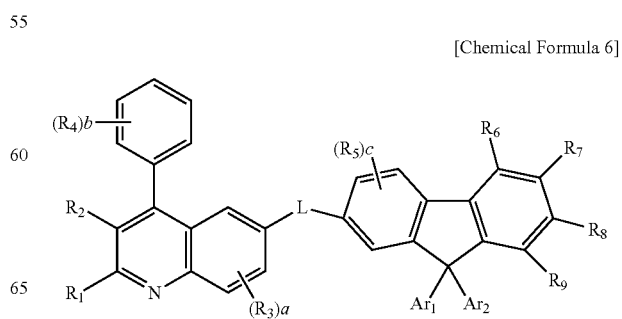

-continued

[Chemical Formula 7]

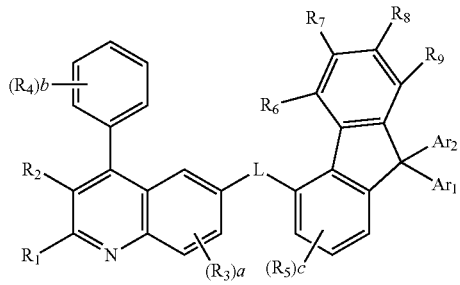

[Chemical Formula 8]

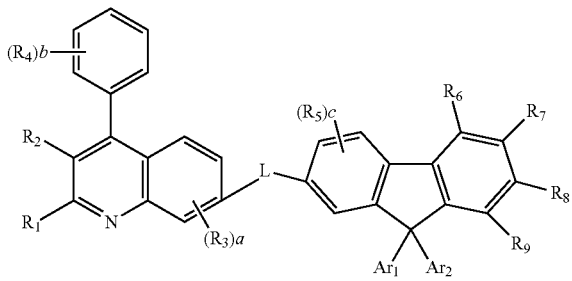

-continued

[Chemical Formula 9]

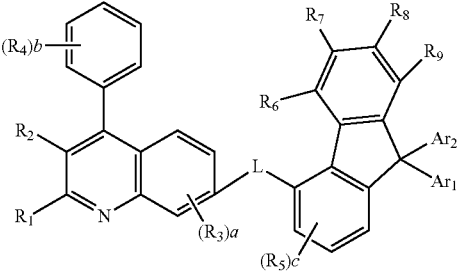

in Chemical Formulae 4 to 9,

L, $Ar_1$, $Ar_2$, $R_1$ to $R_9$, and a to c are the same as those defined in Chemical Formula 1.

4. The compound of claim 1, wherein L is a direct bond; a substituted or unsubstituted phenylene group; a substituted or unsubstituted biphenylylene group; a substituted or unsubstituted naphthylene group; a substituted or unsubstituted divalent phenanthrene group; or a substituted or unsubstituted divalent fluorene group.

5. The compound of claim 1, wherein $Ar_1$ and $Ar_2$ are the same as or different from each other, and are each independently a substituted or unsubstituted phenyl group, or are optionally bonded to an adjacent group to form a ring.

6. The compound of claim 1, wherein $R_1$ is a substituted or unsubstituted phenyl group; a substituted or unsubstituted biphenyl group; a substituted or unsubstituted naphthyl group; a substituted or unsubstituted phenanthryl group; or a substituted or unsubstituted pyridine group.

7. The compound of claim 1, wherein Chemical Formula 1 is selected from the following compounds:

Compound 1

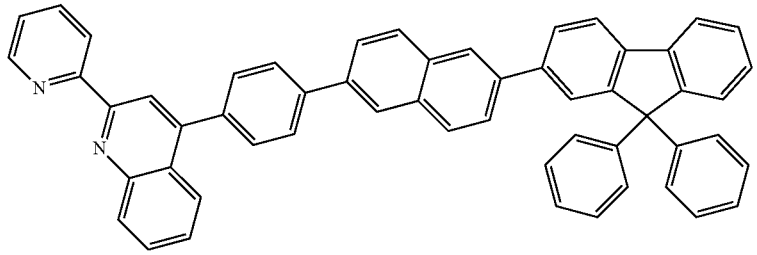

Compound 2

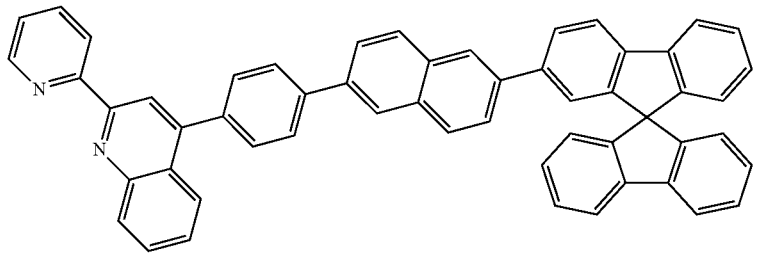

-continued
Compound 3
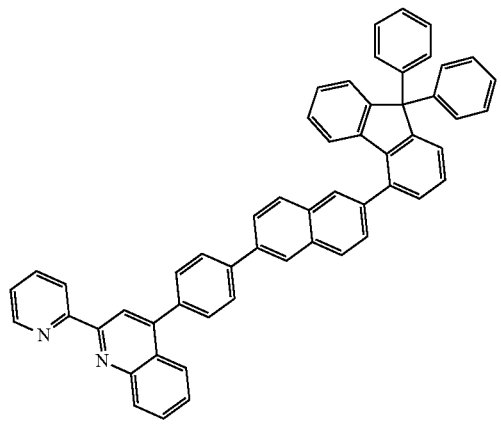
Compound 4
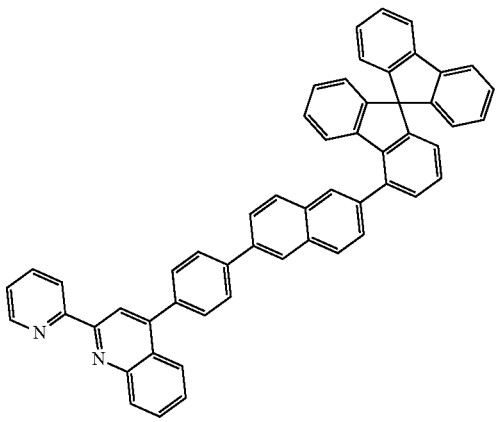
Compound 5
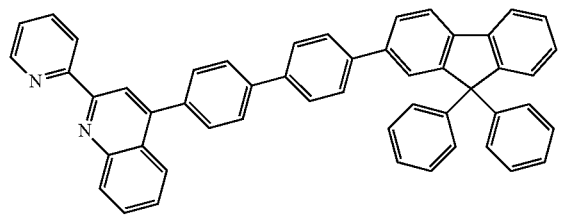
Compound 6
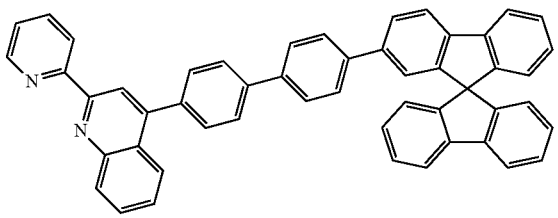
Compound 7
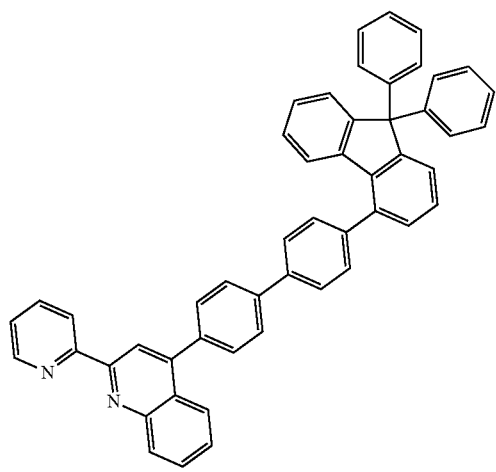
Compound 8
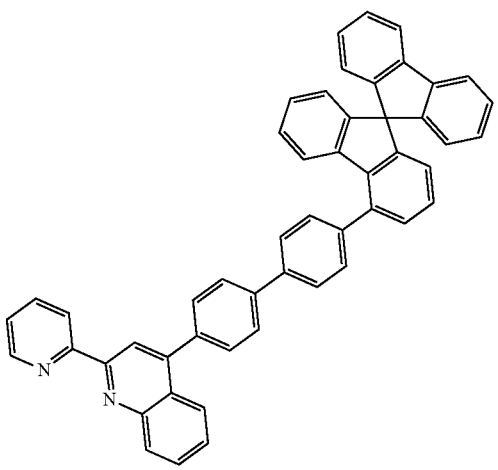
Compound 9
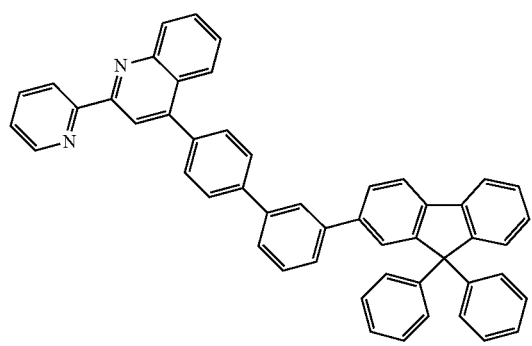
Compound 10
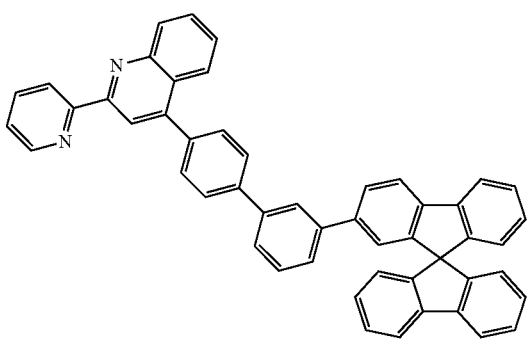

-continued
Compound 11
Compound 12
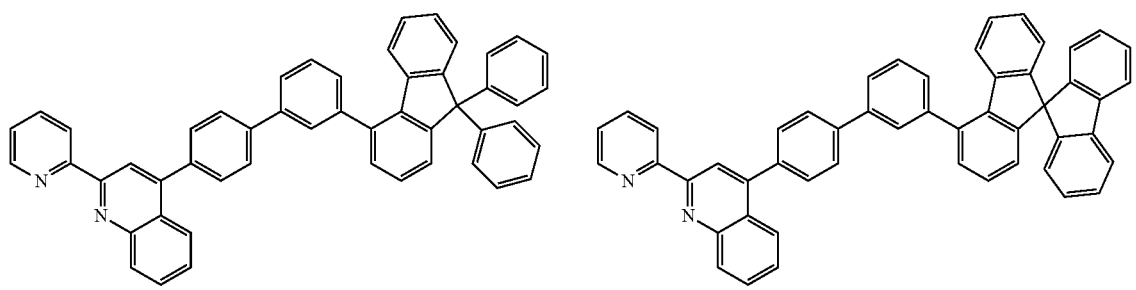
Compound 13
Compound 14
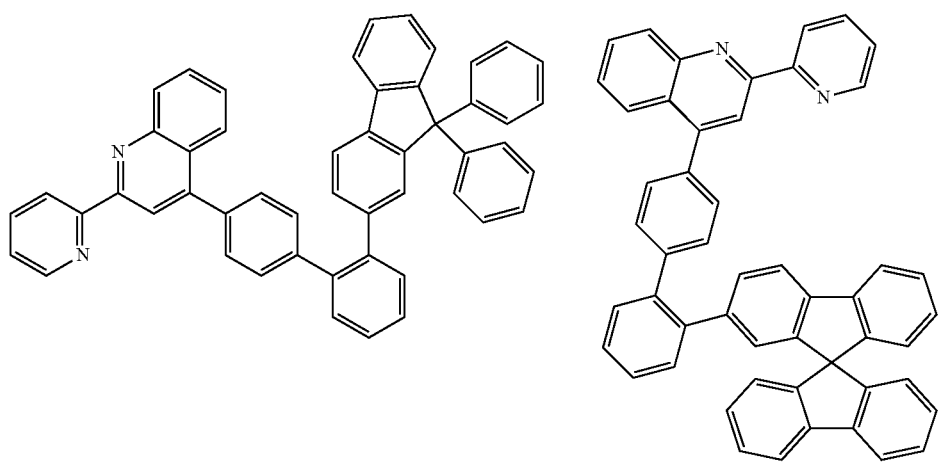
Compound 15
Compound 16
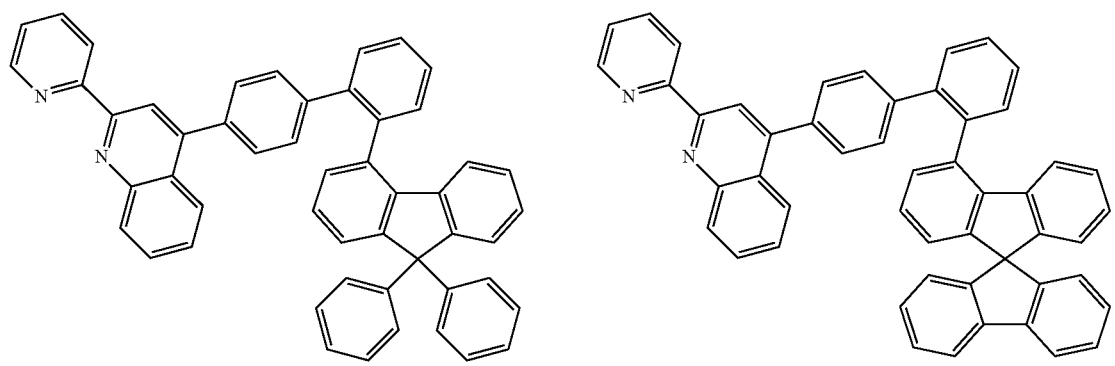
Compound 17
Compound 18
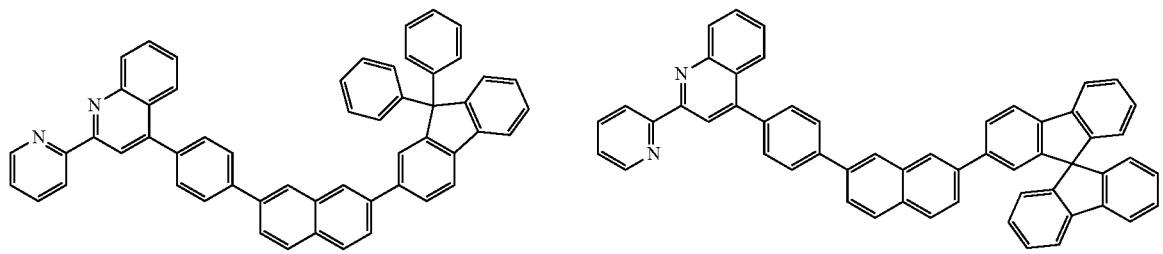

-continued
Compound 19
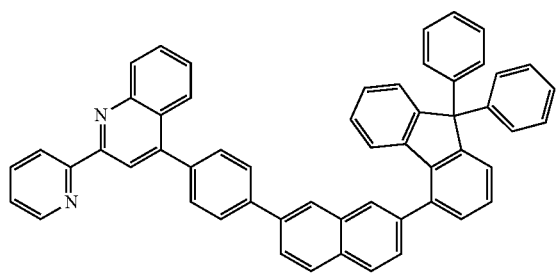
Compound 20
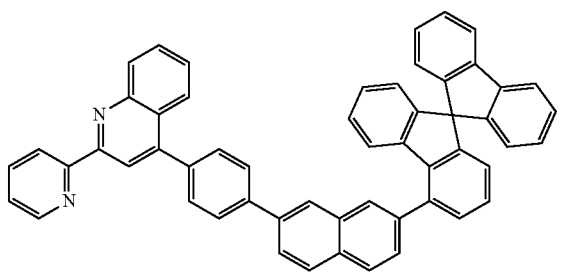
Compound 21
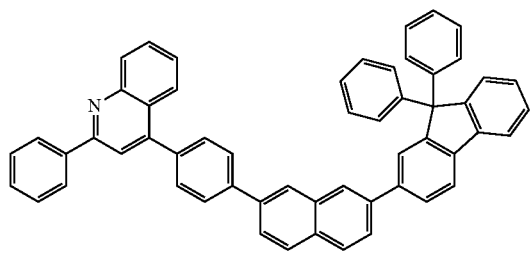
Compound 22
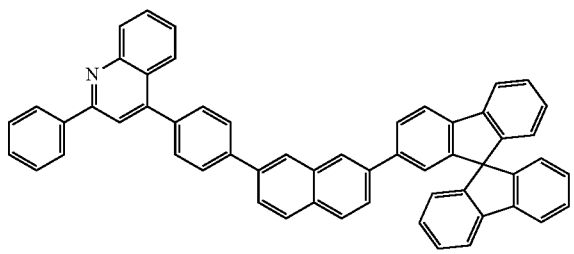
Compound 23
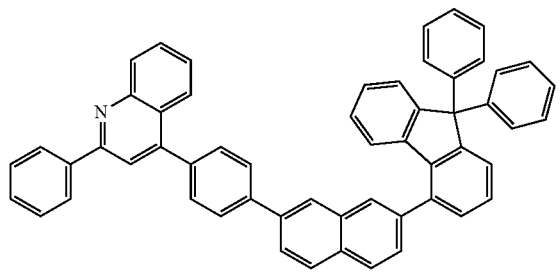
Compound 24
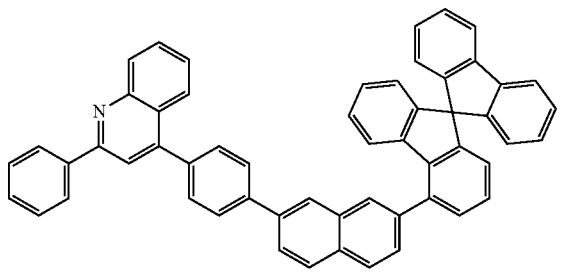
Compound 25
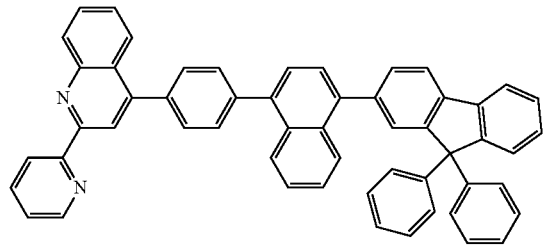
Compound 26
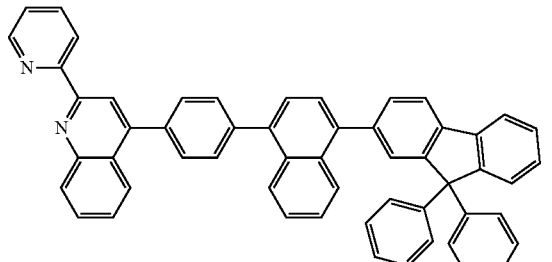
Compound 27
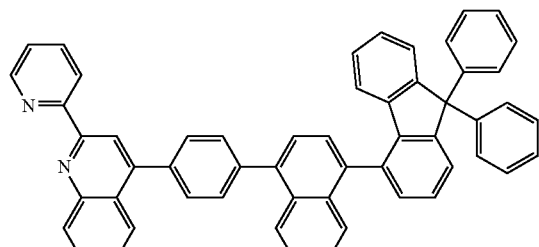
Compound 28
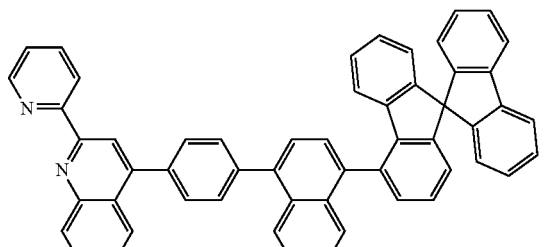

Compound 29
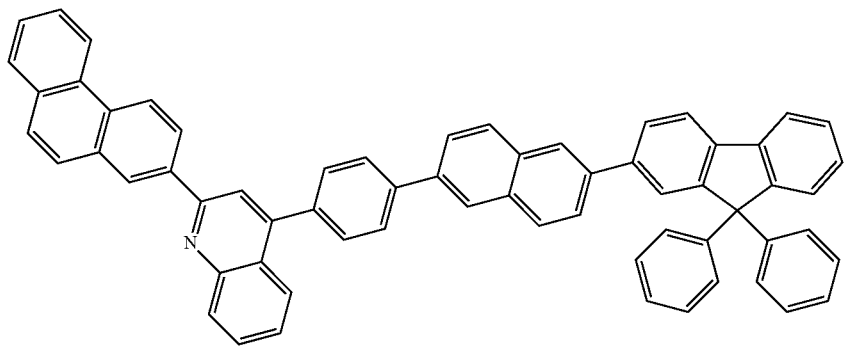
Compound 30
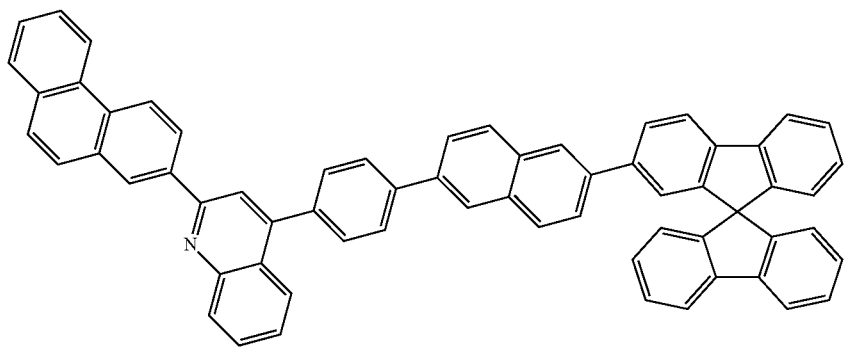
Compound 31
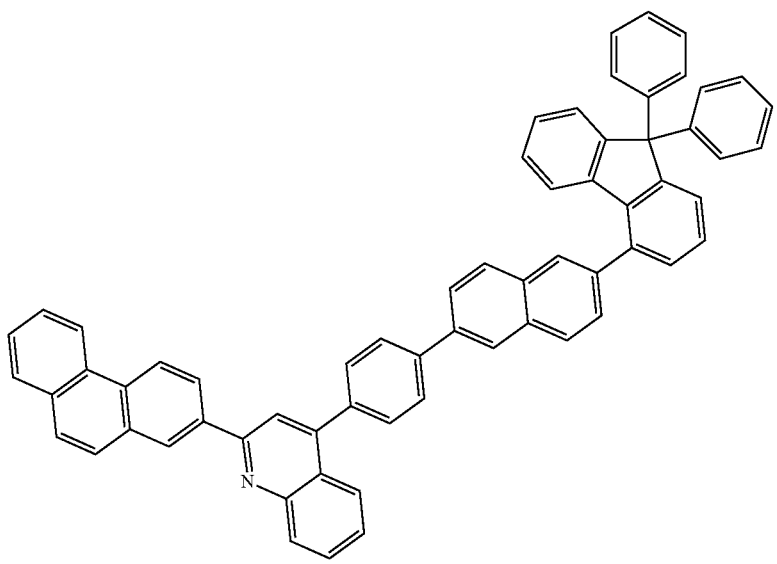

-continued
Compound 32
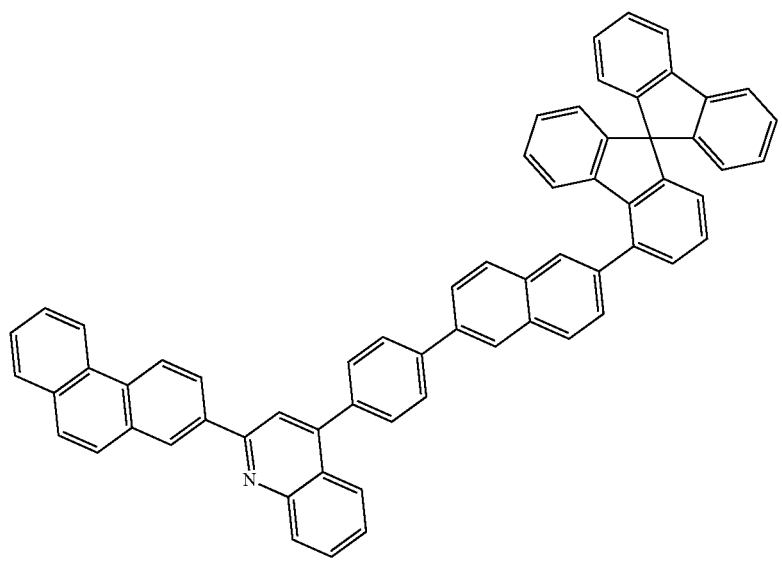
Compound 33
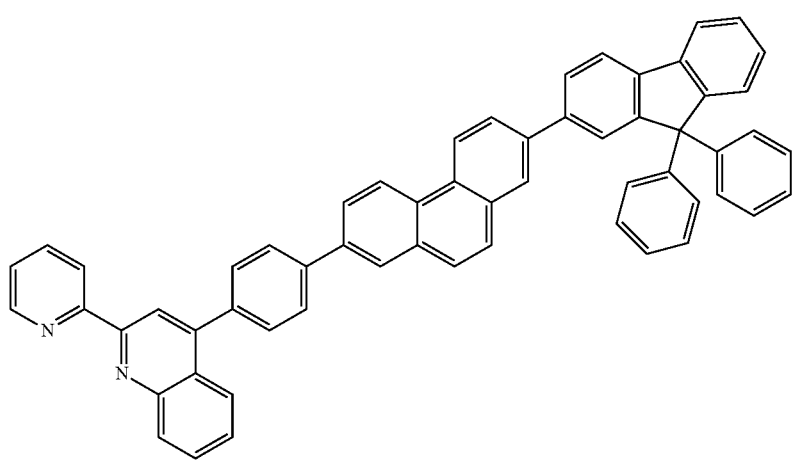
Compound 34
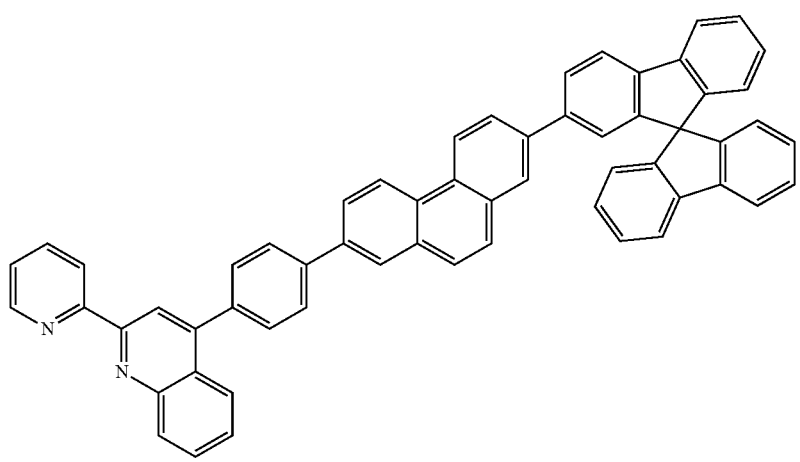

-continued
Compound 35
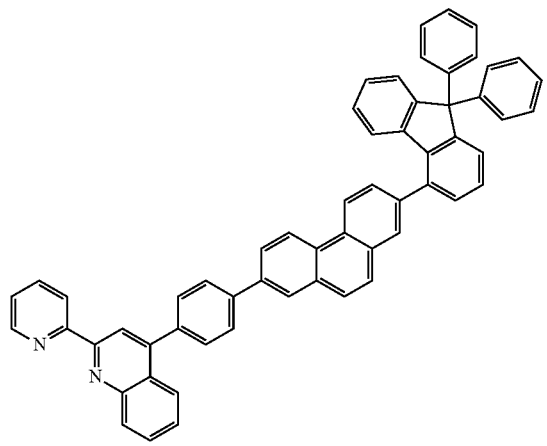
Compound 36
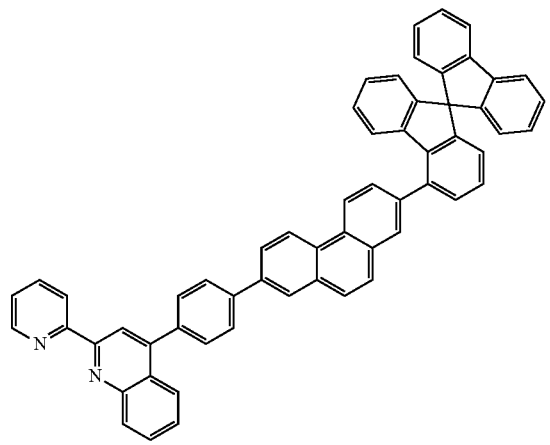
Compound 37
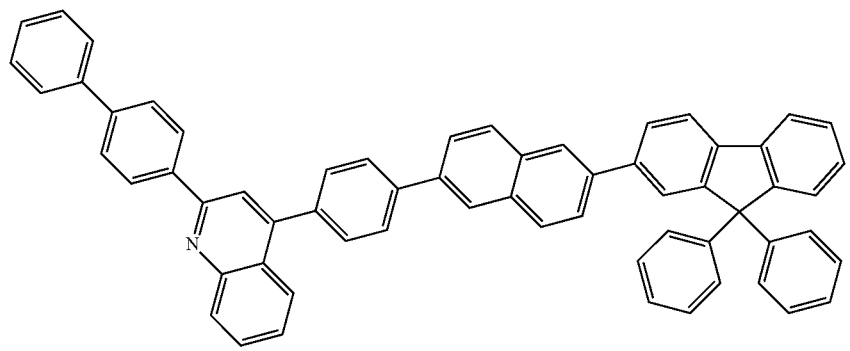
Compound 38
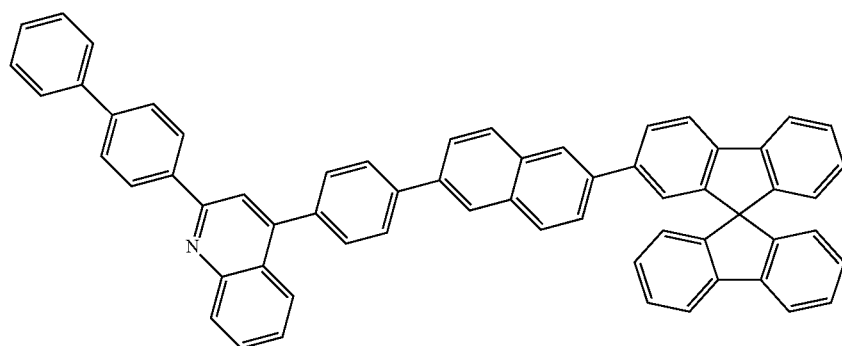

-continued
Compound 39
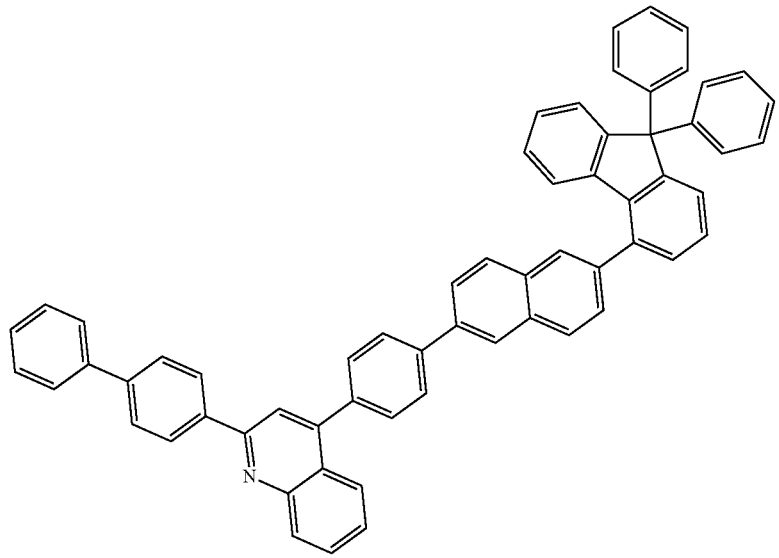
Compound 40
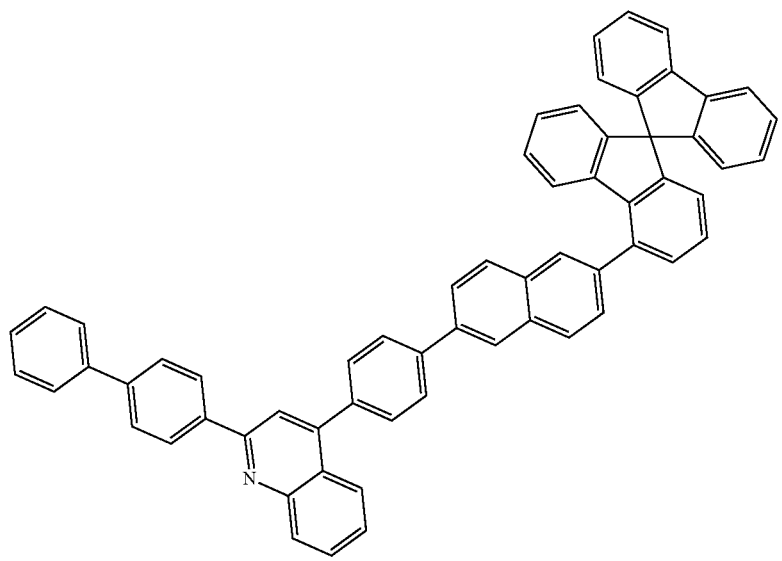
Compound 41 Compound 42
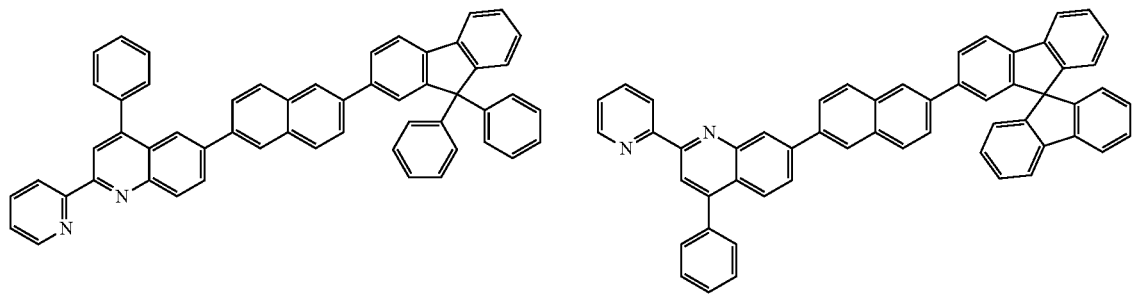

-continued
Compound 43
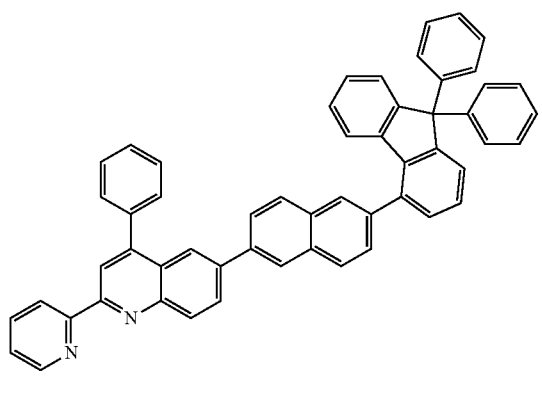
Compound 44
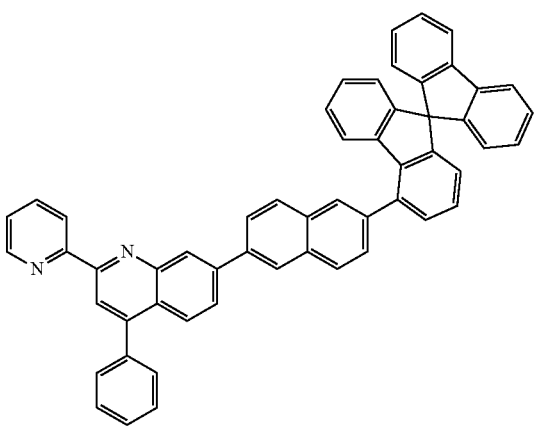
Compound 45
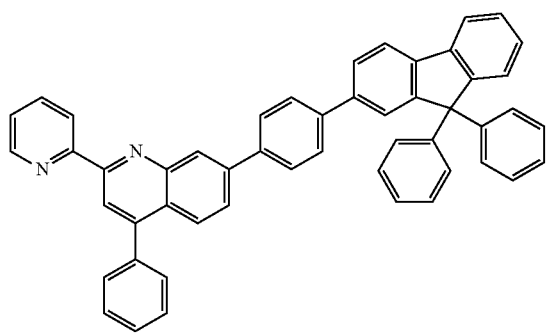
Compound 46
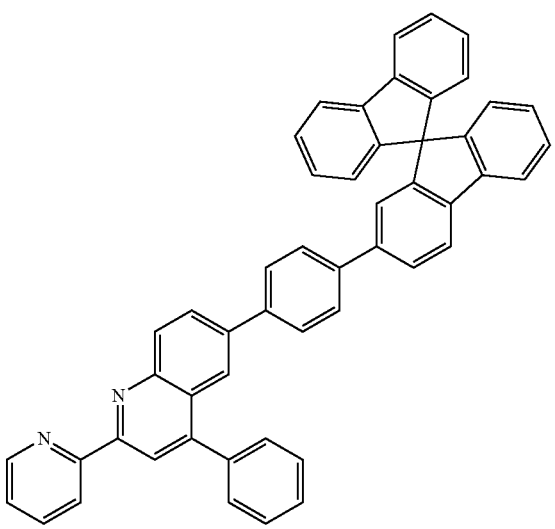
Compound 47
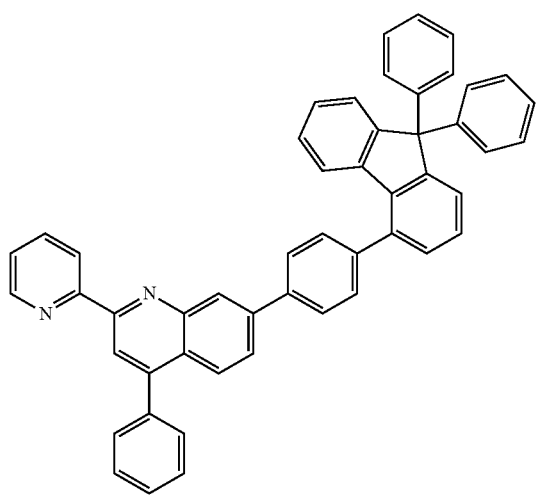
Compound 48
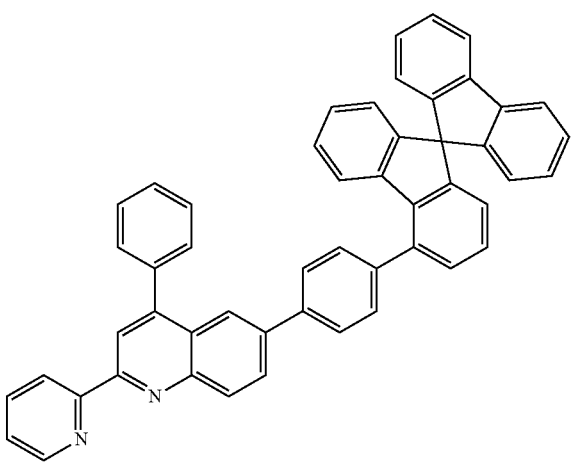

-continued
Compound 49
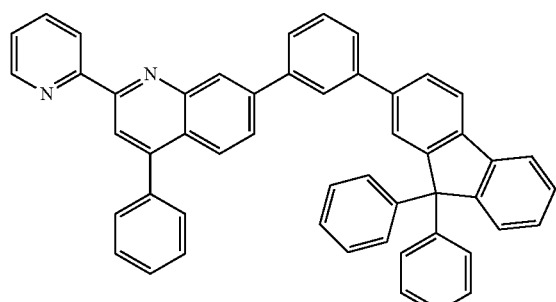
Compound 50
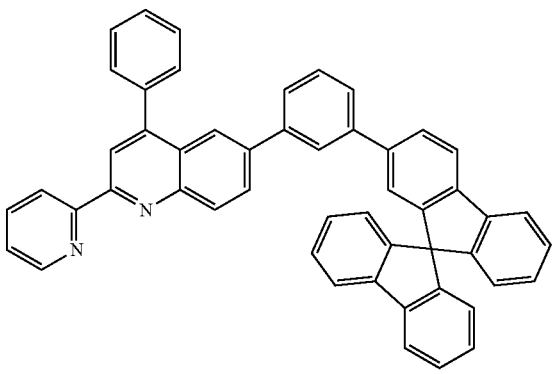
Compound 51
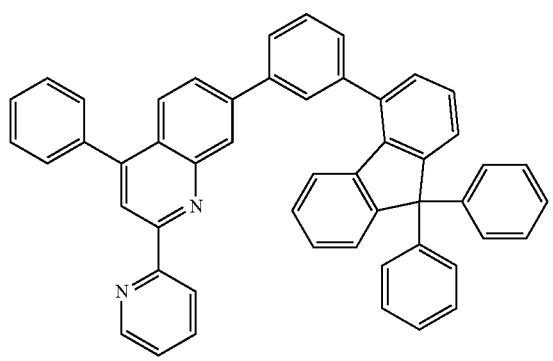
Compound 52
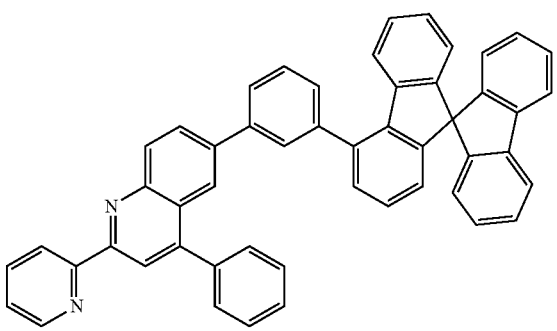
Compound 53
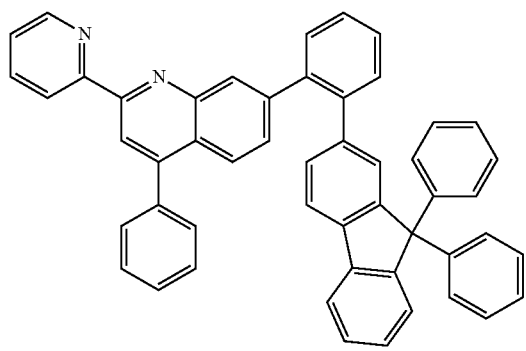
Compound 54
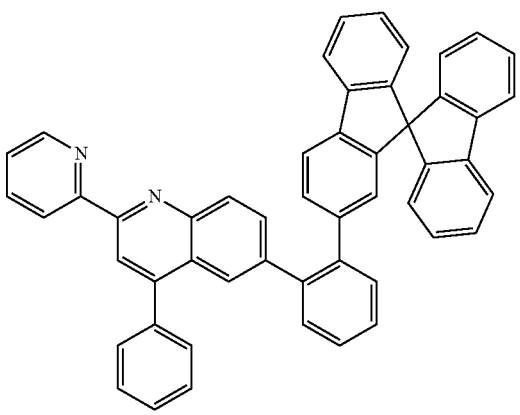

-continued
Compound 55
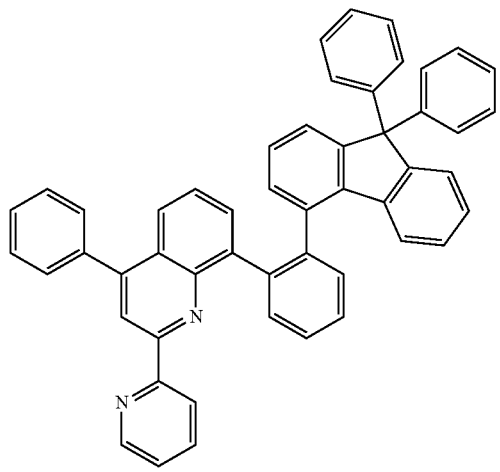
Compound 56
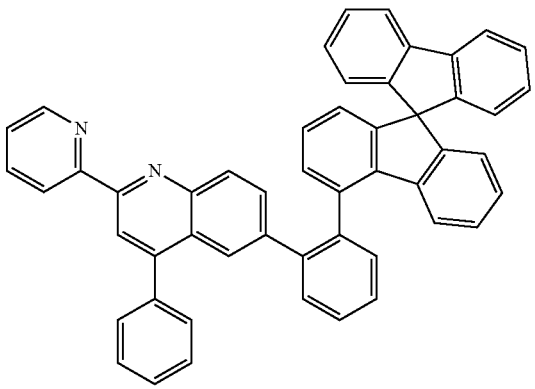
Compound 57
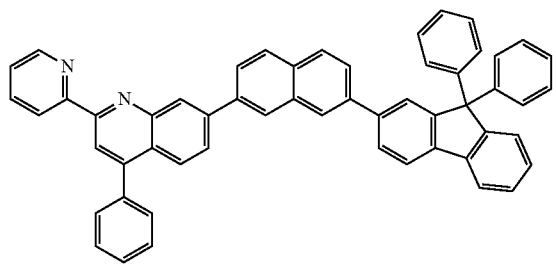
Compound 58
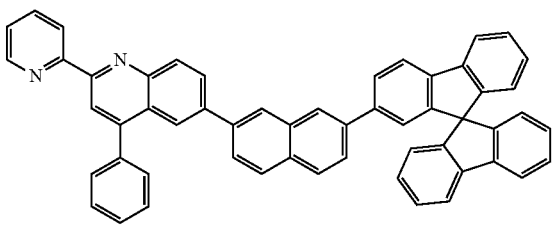
Compound 59
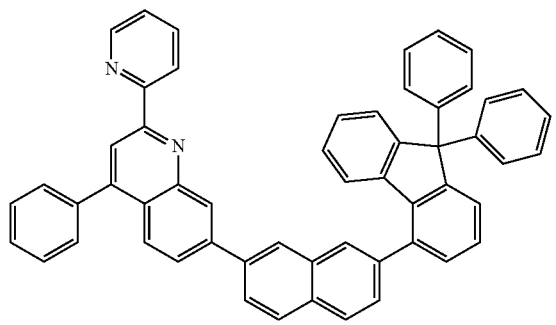
Compound 60
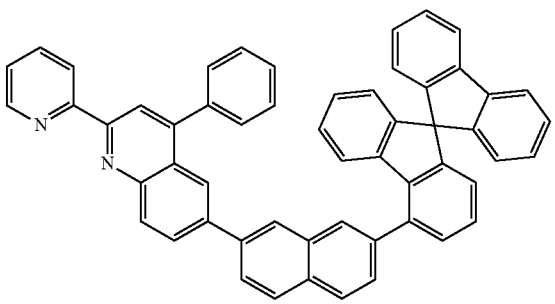
Compound 61
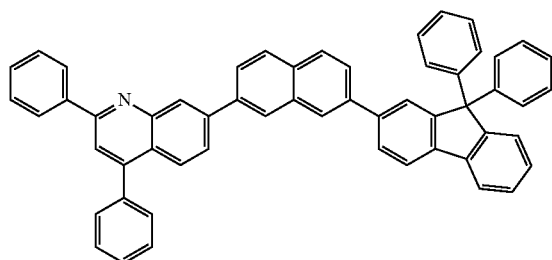
Compound 62
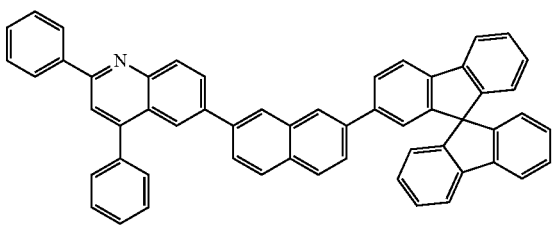

-continued
Compound 63
Compound 64
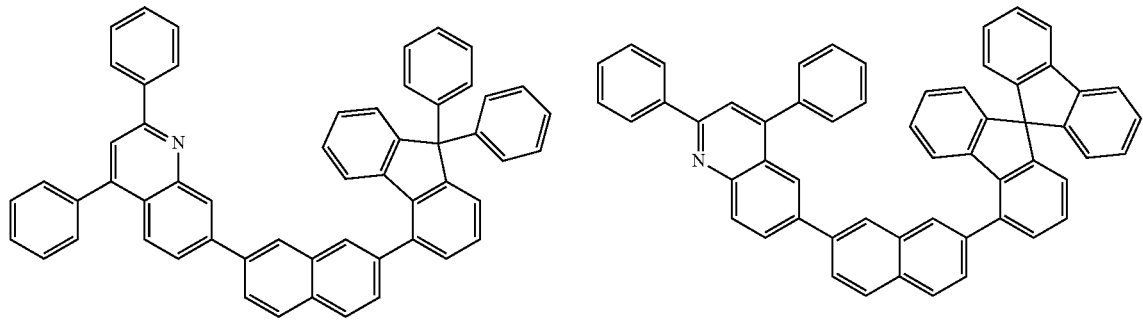
Compound 65
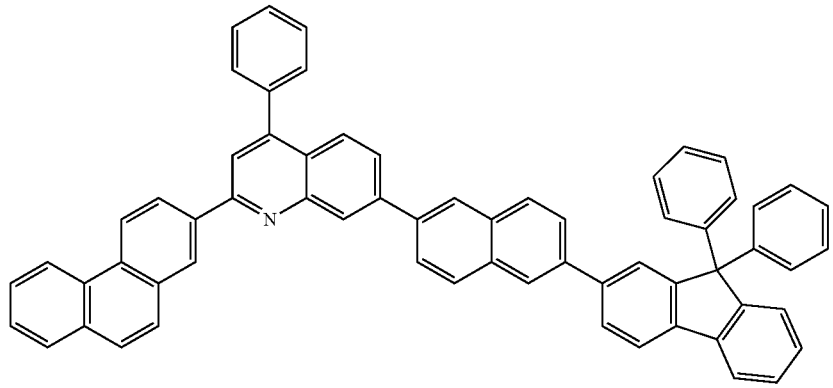
Compound 66
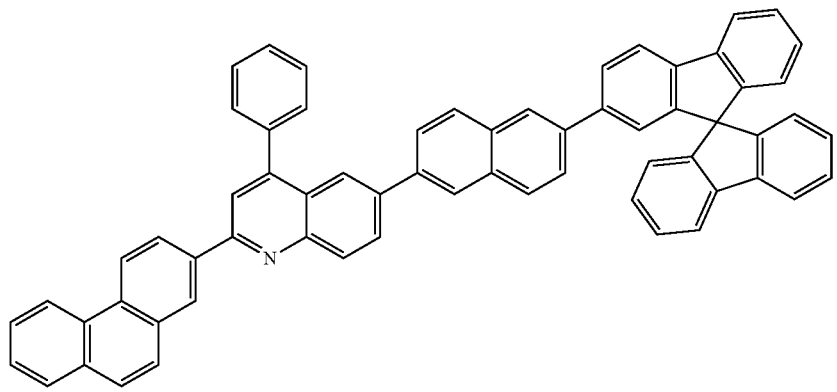
Compound 67
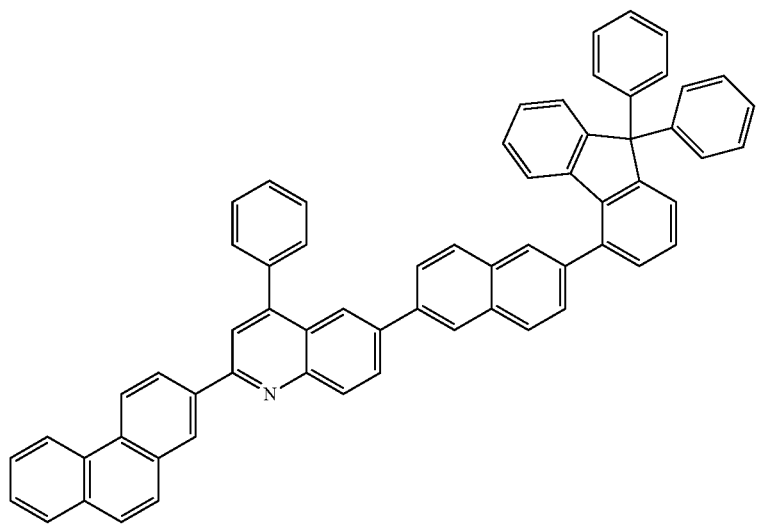

-continued
Compound 68
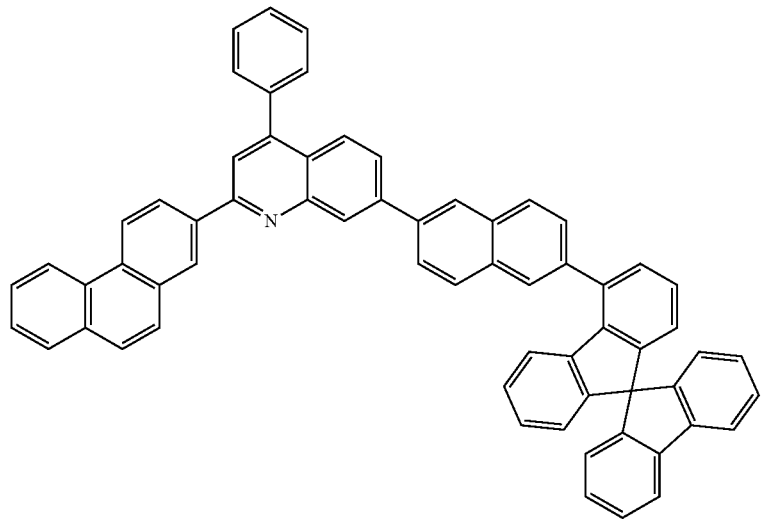
Compound 69
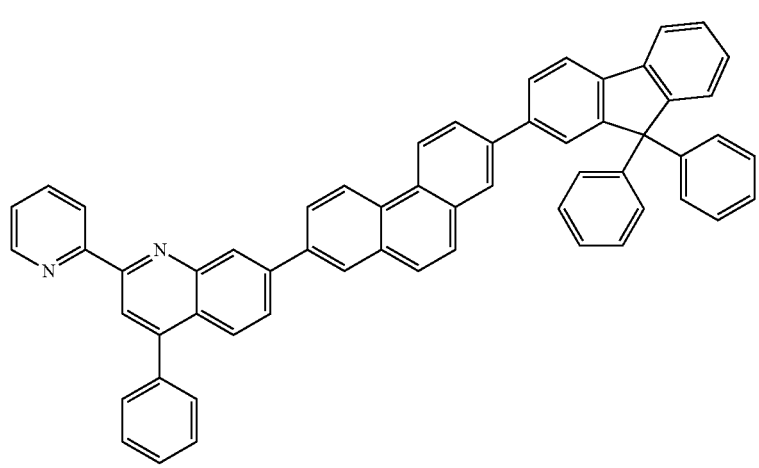
Compound 70
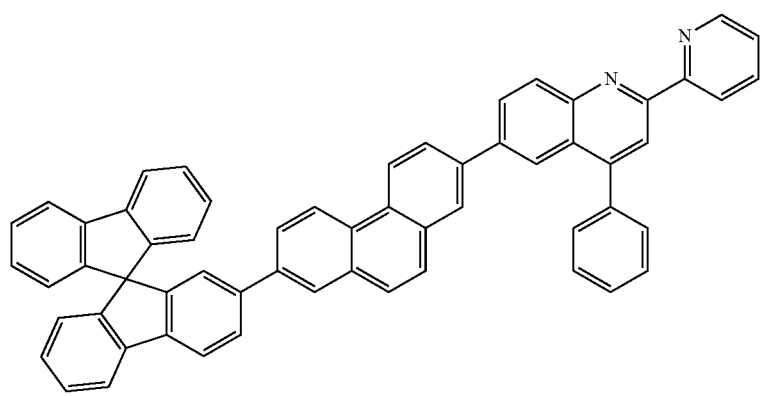

-continued
Compound 71
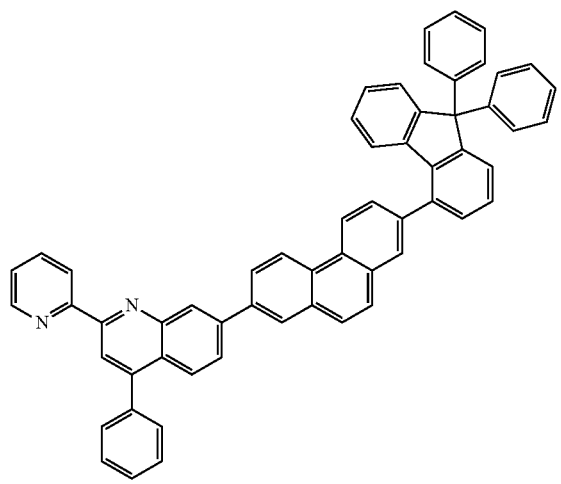
Compound 72
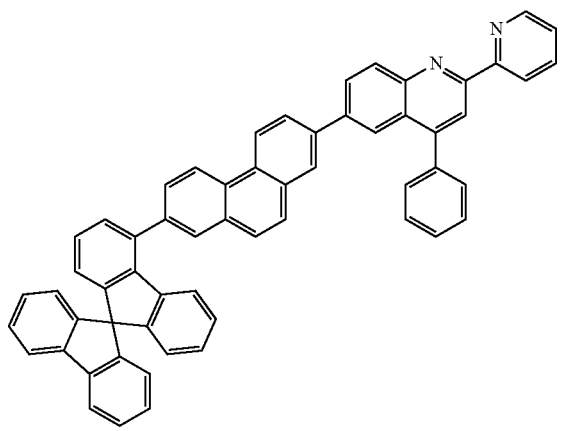
Compound 73
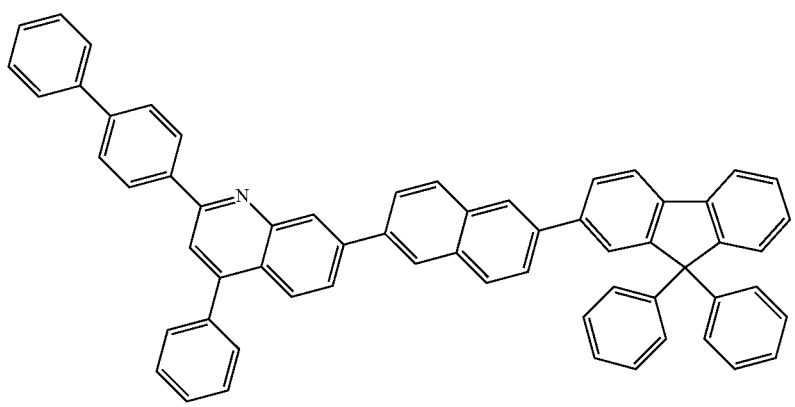
Compound 74
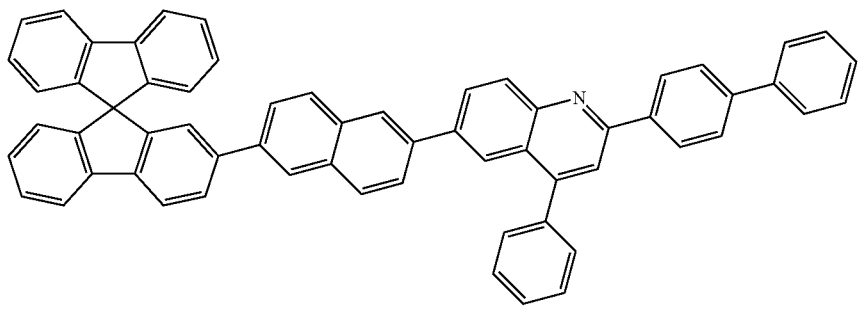

Compound 75
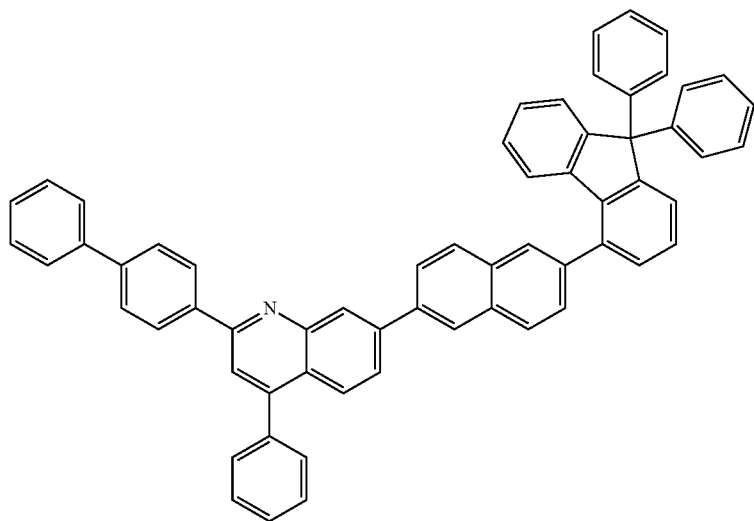
Compound 76
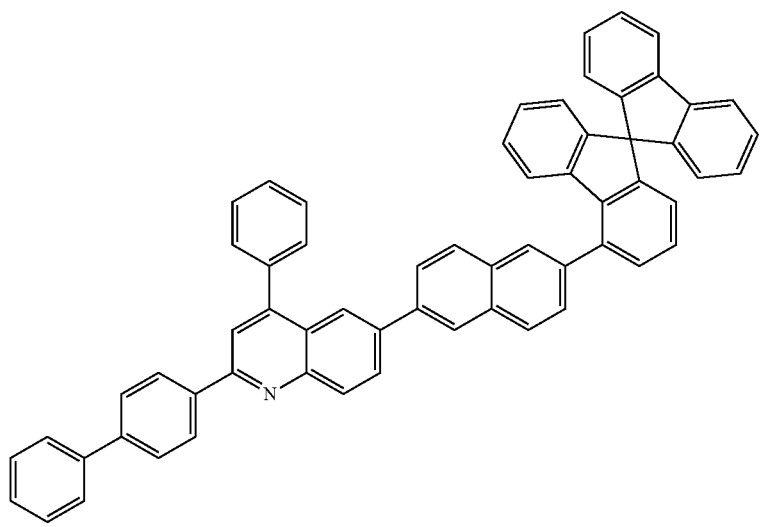
Compound 77
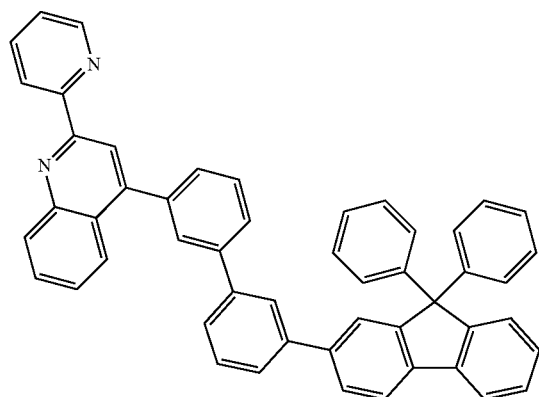
Compound 78
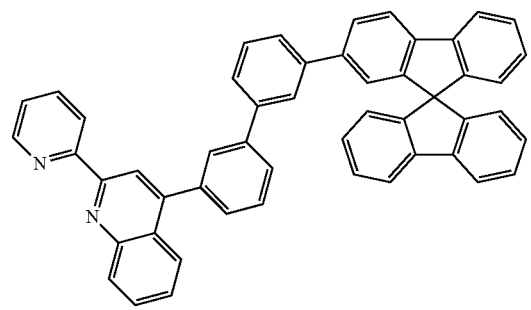

Compound 79

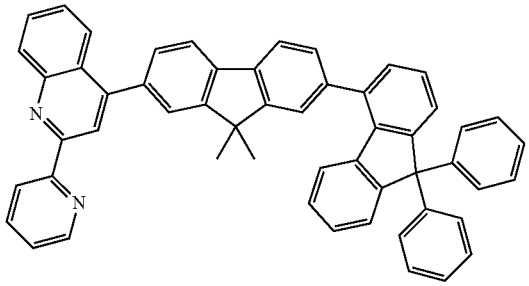

Compound 80

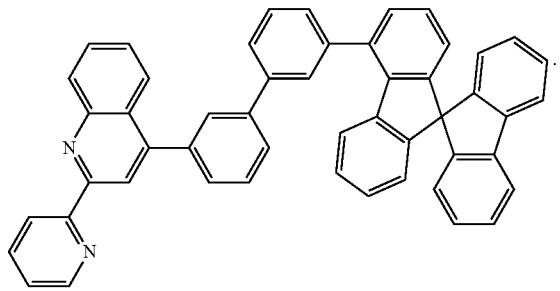

8. An organic electronic device comprising:
a first electrode;
a second electrode disposed to face the first electrode; and
an organic material layer having one or more layers disposed between the first electrode and the second electrode,
wherein the one or more layers of the organic material layer comprise the compound of claim 1.

9. The organic electronic device of claim 8, wherein the organic material layer comprises a light emitting layer, and the light emitting layer comprises the compound.

10. The organic electronic device of claim 8, wherein the organic material layer comprises a hole injection layer or a hole transporting layer, and the hole injection layer or the hole transporting layer comprises the compound.

11. The organic electronic device of claim 8, wherein the organic material layer comprises an electron injection layer, an electron transporting layer, or a layer which injects and transports electrons simultaneously, and the electron injection layer, the electron transporting layer, or the layer which injects and transports electrons simultaneously comprises the compound.

12. The organic electronic device of claim 8, wherein the organic material layer comprises an electron blocking layer or a hole blocking layer, and the electron blocking layer or the hole blocking layer comprises the compound.

13. The organic electronic device of claim 8, wherein the organic electronic device further comprises one or two or more layers selected from the group consisting of a light emitting layer, a hole injection layer, a hole transporting layer, an electron injection layer, an electron transporting layer, an electron blocking layer, and a hole blocking layer.

14. The organic electronic device of claim 8, wherein the organic electronic device is selected from the group consisting of an organic light emitting device, an organic phosphorescent device, an organic solar cell, an organic photoconductor (OPC), and an organic transistor.

15. The organic electronic device of claim 8, wherein the organic material layer comprises a light emitting layer, and the light emitting layer comprises a compound represented by the following Chemical Formula 1-A:

[Chemical Formula 1-A]

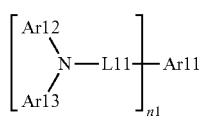

in Chemical Formula 1-A,
n1 is an integer of 1 or more,
Ar11 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L11 is a direct bond; a substituted or unsubstituted arylene group; or a substituted or unsubstituted heteroarylene group,
Ar12 and Ar13 are the same as or different from each other, and are each independently a substituted or unsubstituted aryl group; a substituted or unsubstituted silyl group; a substituted or unsubstituted alkyl group; a substituted or unsubstituted arylalkyl group; or a substituted or unsubstituted heteroaryl group, or are optionally bonded to each other to form a substituted or unsubstituted ring, and
when n1 is 2 or more, two or more structures in the parenthesis are the same as or different from each other.

16. The organic electronic device of claim 15, wherein L11 is a direct bond, Ar11 is a divalent pyrene group, Ar12 and Ar13 are the same as or different from each other, and are each independently an aryl group which is unsubstituted or substituted with a silyl group substituted with an alkyl group, and n1 is 2.

17. The organic electronic device of claim 8, wherein the organic material layer comprises a light emitting layer, and the light emitting layer comprises a compound represented by the following Chemical Formula 2-A:

[Chemical Formula 2-A]

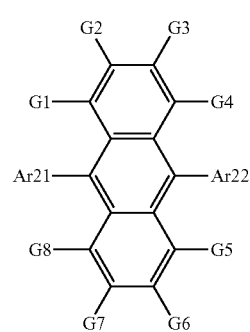

in Chemical Formula 2-A,
Ar21 and Ar22 are the same as or different from each other, and are each independently a substituted or unsubstituted monocyclic aryl group; or a substituted or unsubstituted polycyclic aryl group, and
G1 to G8 are the same as or different from each other, and are each independently hydrogen; a substituted or unsubstituted monocyclic aryl group; or a substituted or unsubstituted polycyclic aryl group.

18. The organic electronic device of claim 17, wherein Ar21 and Ar22 are a 1-naphthyl group, and G1 to G8 are hydrogen.

19. The organic electronic device of claim 15, wherein the light emitting layer comprises a compound represented by the following Chemical Formula 2-A:

[Chemical Formula 2-A]

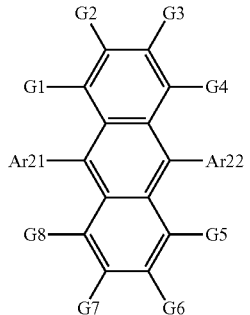

in Chemical Formula 2-A,
Ar21 and Ar22 are the same as or different from each other, and are each independently a substituted or unsubstituted monocyclic aryl group; or a substituted or unsubstituted polycyclic aryl group, and
G1 to G8 are the same as or different from each other, and are each independently hydrogen; a substituted or unsubstituted monocyclic aryl group; or a substituted or unsubstituted polycyclic aryl group.

* * * * *